US005635177A

United States Patent [19]
Bennett et al.

[11] Patent Number: 5,635,177
[45] Date of Patent: Jun. 3, 1997

[54] PROTEIN TYROSINE KINASE AGONIST ANTIBODIES

[75] Inventors: Brian D. Bennett, Pacifica; David Goeddel, Hillsborough; William Matthews, Woodside, all of Calif.

[73] Assignee: Genentech, Inc., South San Francisco, Calif.

[21] Appl. No.: 222,616

[22] Filed: Apr. 4, 1994

Related U.S. Application Data

[63] Continuation-in-part of PCT/US93/00586 Jan. 22, 1993 which is a continuation-in-part of Ser. No. 826,935, Jan. 22, 1992, abandoned.

[51] Int. Cl.[6] .................. C07K 16/00; A61K 39/395; C12N 5/12
[52] U.S. Cl. .................. 424/143.1; 530/387.7; 530/388.26; 424/146.1; 424/138.1; 424/155.1; 435/334; 435/338; 435/330
[58] Field of Search .................. 530/388.26, 387.7; 435/240.27; 424/146.1, 138.1, 155.1

[56] References Cited

FOREIGN PATENT DOCUMENTS

| WO92/14748 | 9/1992 | WIPO . |
| WO93/10136 | 5/1993 | WIPO .......................... C07H 15/12 |
| WO93/15201 | 8/1993 | WIPO . |
| 9315201 | 8/1993 | WIPO . |
| WO95/14776 | 6/1995 | WIPO .......................... C12N 15/12 |

OTHER PUBLICATIONS

Aprelikova et al., "FLT4, a Novel Class III Receptor Tyrosine Kinase in Chromosome 5q33-gter[1]" *Cancer Research* 52:746–748 (1992).
Ashman et al., "Epitope Mapping and Functional Studies with Three Monoclonal Antibodies to the C-KIT Receptor Tyrosine Kinase, YB5.B8, 17F11, and SR-1" *Journal of Cellular Physiology* 158:545–554 (1994).
Bennett et al., "Cloning and Characterization of HTK, a Novel Transmembrane Tyrosine Kinase of the EPH Subfamily" *Journal of Biological Chemistry* 269(19):14211–14218 (1994).
Bennett et al., "Molecular Cloning of a Ligand for a Ligand for the EPH-Related Receptor Protein-Tyrosine Kinase Htk" *Proc. Natl. Acad. Sci. USA* 92:1866–1870 (1995).
Brauninger et al., "Isolation and Characterization of a Human Gene That Encodes a New Subclass of Protein Tyrosine Kinases" *Gene* 110(2):205–211 (1992).
Finnerty et al., "Molecular Cloning of Murine FLT and FLT4" *Oncogene* 8:2293–2298 (1993).
Galland et al., "Chromosomal Localization of FLT4, a Novel Receptor-Type Tyrosine Kinase Gene" *Genomics* 13:475–478 (1992).
Galland et al., "The FLT4 Gene Encodes a Transmembrane Tyrosine Kinase Related to the Vascular Endothelial Growth Factor Receptor" *Oncogene* 8:1233–1240 (1993).
Hao et al., "Isolation and Sequence Analysis of a Novel Human Tyrosine Kinase Gene" *Molecular & Cellular Biology* 9(4):1587–1593 (1988).

Holtrich et al., "Two Additional Protein-Tyrosine Kinases Expressed in Human Lung: Fourth Member of the Fibroblast Growth Factor Receptor Family and an Intracellular Protein-Tyrosine" *Proc. Natl. Acad. Sci.* 88:10411–10415 (1991).
Kaipainen et al., "The Related FLT4, FLT1, and KDR Receptor Tyrosine Kinases Show Distinct Expression Patterns in Human Fetal Endothelial Cells" *Journal of Experimental Medicine* 178:2077–2088 (1993).
Lai et al., "An Extended Family of Protein-Tyrosine Kinase Genes Differentially Expressed in the Vertebrate Nervous System" *Neuron* 6:691–704 (May 1991).
Mark et al., "Expression and Characterization of Hepatocyte Growth Factor Receptor-IgG Fusion Proteins" *Journal of Biological Chemistry* 267(36):26166–26171 (1992).
Pajusola et al., "FLT4 Receptor Tyrosine Kinase Contains Seven Immunoglubulin Like loops and is Expressed in Multiple Human Tissues and Cell Lines" *Cancer Research* 52:5738–5743 (1992).
Pajusola et al., "Two Human FLT4 Receptor Tyrosine Kinase Isoforms with Distinct Carboxy Terminal Tails are Produced by Alternative Processing of Primary Transcripts" *Oncogene* 8:2931–2937 (1993).
Sarup, "Characterization of an Anti-P185$^{her2}$ Monoclonal Antibody that Stimulates Receptor Function and Inhibits Tumor Cell Growth" *Growth Regulation* 1(2):73–82 (1991).
Ullrich et al., "Signal Transduction by Receptors with Tyrosine Kinase Activity" *Cell* 81:203–212 (1990).
Zeigler et al., "Cellular and Molecular Characterization of the Role of the FLK-2/FLT-3 Receptor Tyrosine Kinase in Hematopoietic Stem Cells" *Blood* 84(8):2422–2430 (1994).
Queen et al. PNAS vol. 86. 10029–10033 1989.
Carraway et al., "A Neu Acquaintance for ErbB3 and ErbB4: A Role for Receptor Heterodimerization in Growth Signaling" *Cell* 78:5–8 (Jul. 15, 1994).
Guy et al., "Insect Cell-expressed p180$^{crbB3}$ Possesses an Impaired Tyrosine Kinase Activity" *Proc. Natl. Acad. Sci. USA* 91:8132–8136 (Aug. 1994).
Brizzi et al., "Hematopoietic growth factor receptors" *International Journal of Cell Cloning* 9:274–300 (1991).
Gabrilove et al., "Augmentation of GM-CSF supported progenitor cell growth and partial abrogation of TGF-beta mediated suppression by basic bFGF" *Blood* Abstract No. 42:13a (1991).

(List continued on next page.)

*Primary Examiner*—Lila Feisee
*Attorney, Agent, or Firm*—Wendy M. Lee

[57] ABSTRACT

Agonist antibodies are disclosed which bind to the extracellular domain of receptor protein tyrosine kinases pTKs, and thereby cause dimerization and activation of the intracellular tyrosine kinase domain thereof. The antibodies are useful for activating their respective receptor and thereby enabling the role of the tyrosine kinase receptor in cell growth and/or differentiation to be studied. Chimeric proteins comprising the extracellular domain of the receptor pTKs and an immunoglobulin constant domain sequence are also disclosed.

7 Claims, 54 Drawing Sheets

OTHER PUBLICATIONS

Hanks et al., "The protein kinase family: conserved features and deduced phylogeny of the catalytic domains" *Science* 241:42–52 (1988).

Honma et al., "Induction by some protein kinase inhibitors of differentiation of a mouse megakaryoblastic cell line established by coinfection with Abelson murine leukemia virus and recombinant SV40 retrovirus" Cancer Research 51:4649–4655 (1991).

Kanakura et al., "Phorbol 12–myristate 13–acetate inhibits granulocyte–macrophage colony stimulating factor–induced protein tyrosine phosphorylation in a human factor–dependent hematopoietic cell line" Journal of Biological Chemistry 266:490–495 (1991).

Kanakura et al., "Signal transduction of the human granulocyte–macrophage colony–stimulating factor and interleukin–3 receptors involves tyrosine phosphorylation of a common set of cytoplasmic proteins" *Blood* 76:706–715 (1990).

Matthews et al., "A receptor tyrosine kinase specific to hematopoietic stem and progenitor cell–enriched population" *Cell* 65:1143–1152 (1991).

Miura et al., "Induction of tyrosine phosphorylation by the erythropoietin receptor correlates with mitogenesis" *Molecular & Cellular Biology* 11:4895–4902 (1991).

Rapraeger et al., "Requirement of heparan sulfate for bFGF–mediated fibroblast growth and myoblast differentiation" *Science* 252:1705–1708 (1991).

Rescigno et al., "A putative receptor tyrosine kinase with unique structural topology" *Oncogene* 6:1909–1913 (1991).

Rosnet et al., "Murine Flt3, a gene encoding a novel tyrosine kinase receptor of the PDGFR/CSF1R family" *Oncogene* 6:1641–1650 (1991).

Wilks, "Two putative protein–tyrosine kinases identified by application of the polymerase chain reaction" *Proc. Natl. Acad. Sci. USA* 86:1603–1607 (1989).

Wilks et al., "The application of the polymerase chain reaction to cloning members of the protein tyrosine kinase family" *Gene* 85:67–74 (1989).

Wilks et al., "Two novel protein–tyrosine kinases, each with a second phosphotransferase–related catalytic domain, define a new class of protein kinase" *Molecular & Cellular Biology* 11:2057–2065 (1991).

Yarden et al., "Experimental approaches to hypothetical hormones: detection of a candidate ligand the neu protooncogene" *Proc. Natl. Acad. Sci. USA* 86:3179–3183 (1989).

Bennett et al., "Extracellular Domain–IgG Fusion Proteins for Three Human Natriuretic Peptide Receptors", *Journal of Biological Chemistry* 266(34):23060–23067 (1991).

Böhme et al., "PCR mediated detection of a new human receptor–tyrosine–kinase, HEK 2", *Oncogene* 8:2857–2862 (1993).

Bräuninger et al., "Isolation and characterization of a human gene that encodes a new subclass of protein tyrosine kinases", *Gene* 110:205–211 (1992).

Gilardi–Hebenstreit et al. "An Eph–related receptor protein tyrosine kinase gene segmentally expressed in the developing mouse hindbrain", *Oncogene* 7:2499–2506 (1992).

Hirai et al., "A Novel Putative Tyrosine Kinase Receptor Encoded by the eph Gene", *Science* 238:1717–1720 (1987).

Holtrich et al., "Two additional protein–tyrosine kinases expressed in human lung: Fourth member of the fibroblast growth factor receptor family and an intracellular protein–tyrosine kinase", *Proc. Natl. Acad. Sci. U.S.A.* 88(23):10411–10415 (1991).

International Search Report for corresponding PCT/US93/00586.

Letwin et al., "Novel protein–tyrosine kinase cDNAs related to *fps/fes* and *eph* cloned using anti–phosphotyrosine antibody", *Oncogene* 3:621–627 (1988).

Lhotak et al., "Characterization of Elk, a Brain–Specific Receptor Tyrosine Kinase", *Mol. Cell. Biol.* 11(5):2496–2502 (1991).

Lhotak et al., "Biological and Biochemical Activities of a Chimeric Epidermal Growth Factor–Elk Receptor Tyrosine Kinase", *Mol. Cell. Biol.* 13(11):7071–7079 (1993).

Lindberg et al., "cDNA Cloning and Characterization of eck, an Epithelial Cell Receptor Protein–Tyrosine Kinase in the *eph/elk* Family of Protein Kinases", *Mol. Cell. Biol.* 10(12):6316–6324 (1990).

Maisonpierre et al., "Ehk–1 and Ehk–2: two novel members of the Eph receptor–like tyrosine kinase family with distinctive structures and neuronal expression", *Oncogene* 8:3277–3288 (1993).

Partanen et al., "Putative tyrosine kinases expressed in K–562 human leukemia cells", *Proc. Natl. Acad. Sci. USA* 87:8913–8917 (1990).

Pasquale et al., "Identification of Chicken embryo kinase 5, a developmentally regulated receptor–type tyrosine kinase of the Eph family", *Cell Regulation* 2:523–534 (1991).

Sajjadi et al., "Five novel avian Eph–related tyrosine kinases are differentially expressed", *Oncogene* 8:1807–1813 (1993).

Sajjadi et al., "Identification of a New *eph*–Related Receptor Tyrosine Kinase Gene From Mouse and Chicken That Is Developmentally Regulated and Encodes at Least Two Forms of the Receptor", *New Biol.* 3(8):769–778 (1991).

Ullrich et al., "Signal Transduction by Receptors with Tyrosine Kinase Activity", *Cell* 61:203–212 (1990).

Wicks et al., "Molecular cloning of *HEK*, the gene encoding a receptor tyrosine kinase expressed by human lymphoid tumor cell lines", *Proc. Natl. Acad. Sci. USA* 89:1611–1615 (1992).

Yarden, "Agonistic antibodies stimulated the kinase encoded by the *neu* protooncogene in living cells but the oncogenic mutant is constitutively active", *Proc. Natl. Acad. Sci. USA* 87:2569–2573 (1990).

FIG. 1A

```
GGATCCTGTG CATCAGTGAC TTAGGGCTAG GAACATTCTG CTGTCGGAAA GCGACGTGGT    60
GAAGATCTGT GACTTTGGCC TTGCCCGGGA CATCTACAAA GACCCCAGCT ACGTCCGCAA   120
GCATGCCCGG CTGCCCCCTGA AGTGGATGGC GCCAGAATTC                         160
```

FIG. 1B

```
Asp Pro Val His Gln Xaa Leu Arg Ala Arg Asn Ile Leu Leu Ser Glu
 1               5                  10                  15
Ser Asp Val Val Lys Ile Cys Asp Phe Gly Leu Ala Arg Asp Ile Tyr
             20                  25                  30
Lys Asp Pro Ser Tyr Val Arg Lys His Ala Arg Leu Pro Leu Lys Trp
             35                  40                  45
Met Ala Pro Glu Phe
         50
```

FIG. 2A

```
GGATCCATTC ACAGAGACCT AGCAGCACGC AACATCCTGG TCTCAGAGGA CCTGGTAACC      60
AAGGTCAGCG ACTTTGGCCT GGCCAAAGCC GAGCGGAAGG GGCTAGACTC AAGCCGGCTG     120
CCCGTCAAAT GGATGGCTCC CGAATTC                                        147
```

FIG. 2B

```
Gly Ser Ile His Arg Asp Leu Ala Ala Arg Asn Ile Leu Val Ser Glu
1               5                  10                  15
Asp Leu Val Thr Lys Val Ser Asp Phe Gly Leu Ala Lys Ala Glu Arg
            20                  25                  30
Lys Gly Leu Asp Ser Ser Arg Leu Pro Val Lys Trp Met Ala Pro Glu
        35                  40                  45
Phe
```

FIG. 3A

```
GTT GGA ATT CCT TCC GGC GCC ATC CAT TTC ACC GGC AGC TTT ATT TCG    48
Val Gly Ile Pro Ser Gly Ala Ile His Phe Thr Gly Ser Phe Ile Ser
 1               5                  10                  15

TGT CTA GAT TCA TAG ATG TCT TCA TTA TCT TCA AAA ACT CTG GCA        96
Cys Leu Asp Ser     Met Ser Ser Leu Ser Ser Lys Thr Leu Ala
            20                  25                  30

AGT CCA AAA TCT GCT ACT TTG TAG ATA TTA TGT TCA CCA ACG AGG ACA    144
Ser Pro Lys Ser Ala Thr Leu     Ile Leu Cys Ser Pro Thr Arg Thr
        35                          40                  45

TTCCT                                                              149
Phe
```

FIG. 3B

```
GTG CAC AGG GAT CTC GCG GCT CGG AAC ATC CTC GTC GGG GAA AAC ACC    48
Val His Arg Asp Leu Ala Ala Arg Asn Ile Leu Val Gly Glu Asn Thr
 1               5                  10                  15

CTC TCG AAA GTT GGG GAC TTC GAC TTA GCC AGG CTT ATC AAG GAG GAC    96
Leu Ser Lys Val Gly Asp Phe Asp Leu Ala Arg Leu Ile Lys Glu Asp
            20                  25                  30

GTC TAC CTC TCC CAT GAC CAC AAT ATC CCC TAC AAA TGG ATG GCC CCT    144
Val Tyr Leu Ser His Asp His Asn Ile Pro Tyr Lys Trp Met Ala Pro
        35                          40                  45

GAG GGA A                                                          151
Glu Gly
 50
```

FIG. 3C

```
GTT CAC CGA GAT CTC AAG TCC AAC AAT ATT TTG CTG CTG CAG CCC ATT    48
Val His Arg Asp Leu Lys Ser Asn Asn Ile Leu Leu Leu Gln Pro Ile
 1                   5                  10                  15

GAG AGT GAC GAC ATG GAG CAC AAG ACC CTG AAG ATC ACC GAC TTT GGC    96
Glu Ser Asp Asp Met Glu His Lys Thr Leu Lys Ile Thr Asp Phe Gly
             20                  25                  30

CTG GCC CGA GAG TGG CAC AAA ACC ACA CAA ATG AGT GCC GC            137
Leu Ala Arg Glu Trp His Lys Thr Thr Gln Met Ser Ala
             35                  40              45
```

FIG. 3D

```
GTC AAT CGT GAC CTC GCC CGA AAT GTG TTG CTA GTT ACC CAA CAT        48
Val Asn Arg Asp Leu Ala Arg Asn Val Leu Leu Val Thr Gln His
 1                   5                  10                  15

TAC GCC AAG ATC AGT GAT TTC GGA CTT TCC AAA GCA CTG CGT GCT GAT    96
Tyr Ala Lys Ile Ser Asp Phe Gly Leu Ser Lys Ala Leu Arg Ala Asp
             20                  25                  30

GAA AAC TAC AAG TAC CAG ACC CAT GGA AAG TGG CCT GTC AAG TGG       144
Glu Asn Tyr Lys Tyr Gln Thr His Gly Lys Trp Pro Val Lys Trp
             35                  40                  45

TAC GCT CCG GAA TGC ATC AAC TAC TAC AAG TTC TCC AGC AAA AGC GAT   192
Tyr Ala Pro Glu Cys Ile Asn Tyr Tyr Lys Phe Ser Ser Lys Ser Asp
             50                  55                  60

GTC TGG TCC TTT GGA ATT C                                         211
Val Trp Ser Phe Gly Ile
 65                  70
```

FIG. 4A

```
TTCGAGCTCG CCCGACATTG ATTATTGACT AGTTATTAAT AGTAATCAAT TACGGGGTCA    60
TTAGTTCATA GCCCATATAT GGAGTTCCGC GTTACATAAC TTACGGTAAA TGGCCCGCCT   120
GGCTGACCGC CCAACGACCC CCGCCCATTG ACGTCAATAA TGACGTATGT TCCCATAGTA   180
ACGCCAATAG GGACTTTCCA TTGACGTCAA TGGGTGGAGT ATTTACGGTA AACTGCCCAC   240
TTGGCAGTAC ATCAAGTGTA TCATATGCCA AGTACGCCCC CTATTGACGT CAATGACGGT   300
AAATGCCCCG CCTGGCATTA TGCCCAGTAC ATGACCTTAT GGGACTTTCC TACTTGGCAG   360
TACATCTACG TATTAGTCAT CGCTATTACC ATGGTGATGC GGTTTTGGCA GTACATCAAT   420
GGGCGTGGAT AGCGGTTTGA CTCACGGGGA TTTCCAAGTC TCCACCCCAT TGACGTCAAT   480
GGGAGTTTGT TTTGGCACCA AAATCAACGG GACTTTCCAA AATGTCGTAA CAACTCCGCC   540
CCATTGACGC AAATGGGCGG TAGGCGTGTA CGGTGGGAGG TCTATATAAG CAGAGCTCGT   600
TTAGTGAACC GTCAGATCGC CTGGAGACGC CATCCACGCT GTTTTGACCT CCATAGAAGA   660
CACCGGGACC GATCCAGCCT CCGCGGCCGG GAACGGTGCA TTGGAACGCG GATTCCCCGT   720
GCCAAGAGTG ACGTAAGTAC CGCCTATAGA GTCTATAGGC CCACTTGGCT TCGTTAGAAC   780
GCGGCTACAA TTAATACATA ACCTTATGTA TCATACACAT ACGATTTAGG TGACACTATA   840
GAATAACATC CACTTTGCCT TTCTCTCCAC AGTGTCCACC TCCCAGGTCC AACTGCACCT   900
CGGTTCTATC GATTGAATTC CCCGGGGATC CTCTAGAGAT CCCTCGACCT CGAGATCCAT   960
TGTGCTGGCG CGGATTCTTT ATCACTGATA AGTTGGTGGA CATATTATGT TTATCAGTGA  1020
```

FIG. 4B

```
TAAAGTGTCA AGCATGACAA AGTTGCAGCC GAATACAGTG ATCCGTGCCG CCCTAGACCT    1080
GTTGAACGAG GTCGGCGTAG ACGGTCTGAC ACACGCAAA  CTGGCGGAAC GGTTGGGGT    1140
TCAGCAGCCG GCGCTTTACT GGCACTTCAG GAACAAGCGG GCGCTGCTCG ACGCACTGGC    1200
CGAAGCCATG CTGGCGGAGA ATCATAGCAC TTCGGTGCCG AGAGCCGACG ACGACTGGCG    1260
CTCATTTCTG ACTGGGAATG CCCCGCAGCTT CAGGCAGGCG CTGCTCGCCT ACCGCCAGCA    1320
CAATGGATCT CGAGGATCT  TCCATACCTA CCAGTTCTGC GCCTGCAGGT CGCGGCCCGCA    1380
CTACTCTTTG ATGTATTACT CATATTACCA AGGAATAACT GGCGGGCACA GGTCAGGTG     1440
CTGAAGGGAC ATTGTGAGAA GTGACCTAGA AGGCAAGAGG TGAGCCCTCT GTCACGCTGG    1500
CATAAGGGCC GCTTGAGGGC TCTTTGGTCA AGCAGTAACG CCAGTGTCTG GGAAGGCACC    1560
TGTTACTCAG CAGACCATGA AAGGGCGTCT CCCTTTCCTT GGAGCAGTCA GGAACACTC    1620
TGCTCCACCA GCTTCTGTG  GGAGCCTGGA TATTATCCAG GCCTGCCCGC AGTCATCCGG    1680
AGGCCTAACC CCTCCCTGTG GTGCTTCAGT GGTCACACTC CTTGTCCACT TTCATGCTCC    1740
TCTTGGCCTC CTGGTTCCTC TTGGAAGTTT GTAGTAGATA GCAGAAGAAA TAGCGAAAGT    1800
CTTAAAGTCT TTGATCTTTC TTATAAGTGC AGAGAAGAAA TGCTGACGTA TGCTGCCTTC    1860
TCTCTCTCTG CTTCAGCTAC CTGAAGCCGC TTTCTTGTCT ATACCTGCTC TCTATCTGCT    1920
CACACTCCTC CGAGGCCAGC ACCATCCCAC TGTCTGTCTG GTTGTCCACA GAGCCTTTGT    1980
AGTCGTTGG GGTCATGGGG AATTCCTCAA ATGTCTTCAT CCTGGAGGAA CCACGGGTCT    2040
```

FIG. 4C

```
CAGCCCCTCT GGCCAGGCAC CCGGGAAAGG ACACCCAGTT GTAATACCTG GCGGCCAGGC   2100
TGTGGCGCTG CAGGCTTGGC GGCTGTCCT  CAGCGTCAGC CTGGGCGATG TGTAGGGCCA   2160
TGGTGGACAC CTGCGAGAAG CTGCCCTCTT CTGAGCTCTG AGAGCTGCGC GGGGCCATGC   2220
AGACCTCCTC TTCCTCTTGC AGGCCCCTGC CCTGGAGCAG GTCCCCCAGG ATCTCCACCA   2280
GCTCCGAGAA TGCAGGTCTC GCCTTGGGGT CTCCGGACCA GCAGTTCAGC ATGATGCGGC   2340
GTATGGCGGG AGTGGCCAGC TCCGGGGCCC TCATCCTTGT GCCGTCTCTC AGCCGCTGGC   2400
AGAACTCCTC ATTGATCTGC ACCCCAGGGT ACGGGGAGGC CCCCAGAGAG AAGATCTCCC   2460
AGAGAAGCAC CCCAAAGGAC CACACGTCAC TCTGCGTGGT GTACACCTTG TCGAAGATGC   2520
TTTCAGGGGC CATCCACTTC AGGGGCAGCC GGGCACTGCC CTTGCGGACG TAGTCGGGGT   2580
CTTTGTAGAT GTCCCGGGCA AGGCCAAAGT CACAGATCTT CACCACGTCG CTTTCCGACA   2640
GCAGAATGTT CCGAGCAGCC AGGTCTCTGT GGATGCACTT TCGGGAAGCC AGGAACTCCA   2700
TCCCTCTGGC CACCTGGAAG CTGTAGCAGA CAAGATCTTC CATGGTCAGC GGGCTCAGCC   2760
ACAGGTCCTC AGCTTCTTGG TCTGGAGAAG CCCGCCCTGC TCCGCCCTCG GTCTTCGAGA   2820
ACCGGCGAA  GAGGACCCTG TCGCTGCTCC CCGGCCCGCC CCGATCCAGC CTGGCGAGCT   2880
CCACCATGGC GCGGAAGCGT CCGGCTGCT  CGGGAGACTT CTCCTGCGGA TGCACGAAGC   2940
TGGCTCGAGG GCGCCCAGTC GTCCGCCCGA GAGGCGCCTC CATTCCCCCG CCGCCCCGG    3000
CGCCCCCGCAG GCCGCCCGCT CACCGNGCAG GGGCTGCGGC CGCGACTCTA GAGTCGACCT  3060
```

FIG. 4D

```
GCAGAAGCTT GGCCGCCATG GCCCAACTTG TTTAATTGCAG CTTATAATGG TTACAAATAA  3120
AGCAATAGCA TCACAAATTT CACAAATAAA GCATTTTTT CACTGCATTC TAGTTGTGGT  3180
TTGTCCAAAC TCATCAATGT ATCTTATCAT GTCTGGATCG ATCGGGAATT AATTCGGGCGC  3240
AGCACCATGG CCTGAAATAA CCTCTGAAAG AGGAACTTGG TTAGGTACCT TCTGAGGCGG  3300
AAAGAACCAG CTGTGGAATG TGTGTCAGTT AGGGTGTGGA AAGTCCCCAG GCTCCCCAGC  3360
AGGCAGAAGT ATGCAAAGCA TGCATCTCAA TTAGTCAGCA ACCAGGTGTG GAAAGTCCCC  3420
AGGCTCCCCA GCAGGCAGAA GTATGCAAAG CATGCATCTC AATTAGTCAG CAACCATAGT  3480
CCCGCCCCTA ACTCCGCCCA TCCCGCCCCT AACTCCGCCC AGTTCCGCCC ATTCTCCGCC  3540
CCATGGCTGA CTAATTTTT TTATTTATGC AGAGGCCGAG GCCGCCTCGG CCTCTGAGCT  3600
ATTCCAGAAG TAGTGAGGAG GCTTTTTTGG AGGCCTAGGC TTTTGCAAAA AGCTGTTAAC  3660
AGCTTGGCAC TGGCCGTCGT TTTACAACGT CGTGACTGGG AAAACCCTGG CGTTACCCAA  3720
CTTAATCGCC TTGCAGCACA TCCCCCCTTC GCCAGCTGGC GTAATAGCGA AGAGGCCCGC  3780
ACCGATCGCC CTTCCCAACA GTTGCGTAGC CTGAATGGCG AATGGCGCCT GATGCGGTAT  3840
TTTCTCCTTA CGCATCTGTG CGGTATTTCA CACCGCATAC GTCAAAGCAA CCATAGTACG  3900
CGCCCTGTAG CGGCGCATTA AGCGCGGCGG GTGTGGTGGT TACGCGCAGC GTGACCGCTA  3960
CACTTGCCAG CGCCCTAGCG CCCGCTCCTT TCGCTTTCTT CCCTTCCTTT CTCGCCACGT  4020
TCGCCGGCTT TCCCCGTCAA GCTCTAAATC GGGGGCTCCC TTTAGGGTTC CGATTTAGTG  4080
```

FIG. 4E

```
CTTTACGGCA CCTCGACCCC AAAAAACTTG ATTTGGGTGA TGGTTCACGT AGTGGGCCAT   4140
CGCCCTGATA GACGGTTTTT CGCCCTTTGA CGTTGGAGTC CACGTTCTTT AATAGTGGAC   4200
TCTTGTTCCA AACTGGAACA ACACTCAACC CTATCTCGGG CTATTCTTTT GATTATAAG    4260
GGATTTTGCC GATTTCGGCC TATTGGTTAA AAAATGAGCT GATTTAACAA AAATTTAACG   4320
CGAATTTTAA CAAAATATTA ACGTTTACAA TTTTATGGTG CACTCTCAGT ACAATCTGCT   4380
CTGATGCCGC ATAGTTAAGC CAACTCCGCT ATCGCTACGT GACTGGGTCA TGGCTGCGCC   4440
CCGACACCCG CCAACACCCG CTGACGCGCC CTGACGGGCT TGTCTGCTCC CGGCATCCGC   4500
TTACAGACAA GCTGTGACCG TCTCCGGGAG CTGCATGTGT CAGAGGTTTT CACCGTCATC   4560
ACCGAAACGC GCGAGGCAGT ATTCTTGAAG ACGAAAGGGC CTCGTGATAC GCCTATTTTT   4620
ATAGGTTAAT GTCATGATAA TAATGGTTTC TTAGACGTCA GGTGGCACTT TTCGGGGAAA   4680
TGTGCGCGGA ACCCCTATTT GTTTATTTTT CTAAATACAT TCAAATATGT ATCCGCTCAT   4740
GAGACAATAA CCCTGATAAA TCTTCAATA ATATTGAAAA AGGAAGAGTA TGAGTATTCAA    4800
ACATTCCGT GTCGCCCTTA TTCCCTTTTT GGCGGCATTT TGCCTTCCTG TTTTTGCTCA    4860
CCCAGAAACG CTGGTGAAAG TAAAAGATGC TGAAGATCAG TTGGGTGCAC GAGTGGGTTA   4920
CATCGAACTG GATCTCAACA GCGGTAAGAT CCTTGAGAGT TTTCGCCCCG AAGAACGTTT   4980
TCCAATGATG AGCACTTTTA AAGTTCTGCT ATGTGGCGCG GTATTATCCC GTATGACGC    5040
CGGGCAAGAG CAACTCGGTC GCCGCATACA CTATTCTCAG AATGACTTGG TTGAGTACTC   5100
```

FIG. 4F

```
ACCAGTCACA GAAAAGCATC TTACGGATGG CATGACAGTA AGAGAATTAT GCAGTGCTGC    5160
CATAACCATG AGTGATAACA CTGCGGCCAA CTTACTTCTG ACAACGATCG GAGGACCGAA    5220
GGAGCTAACC GCTTTTTTGC ACAACATGGG GGATCATGTA ACTCGCCTTG ATCGTTGGGA    5280
ACCGGAGCTG AATGAAGCCA TACCAAACGA CGAGCGTGAC ACCACGATGC CAGCAGCAAT    5340
GGCAACAACG TTGCGCAAAC TATTAACTGG CGAACTACTT ACTCTAGCTT CCCGGCAACA    5400
ATTAATAGAC TGGATGGAGG CGGATAAAGT TGCAGGACCA CTTCTGCGCT CGGCCCTTCC    5460
GGCTGGCTGG TTTATTGCTG ATAAATCTGG AGCCGGTGAG CGTGGGTCTC GCGGTATCAT    5520
TGCAGCACTG GGGCCAGATG GTAAGCCCTC CCGTATCGTA GTTATCTACA CGACGGGGAG    5580
TCAGGCAACT ATGGATGAAC GAAATAGACA GATCGCTGAG ATAGGTGCCT CACTGATTAA    5640
GCATTGGTAA CTGTCAGACC AAGTTTACTC ATATATACTT TAGATTGATT TAAAACTTCA    5700
TTTTTAATTT AAAAGGATCT AGGTGAAGAT CCTTTTTGAT AATCTCATGA CCAAAATCCC    5760
TTAACGTGAG TTTTCGTTCC ACTGAGCGTC AGACCCCGTA GAAAAGATCA AAGGATCTTC    5820
TTGAGATCCT TTTTTTCTGC GCGTAATCTG CTGCTTGCAA ACAAAAAAAC CACCGCTACC    5880
AGCGGTGGTT TGTTTGCCGG ATCAAGAGCT ACCAACTCTT TTTCCGAAGG TAACTGGCTT    5940
CAGCAGAGCG CAGATACCAA ATACTGTCCT TCTAGTGTAG CCGTAGTTAG GCCACCACTT    6000
CAAGAACTCT GTAGCACCGC CTACATACCT CGCTCTGCTA ATCCTGTTAC CAGTGGCTGC    6060
TGCCAGTGGC GATAAGTCGT GTCTTACCGG GTTGGACTCA AGACGATAGT TACCGGATAA    6120
```

FIG. 4G

```
GGGCGAGCGG TCGGGCTGAA CCGGGGGTTC GTGCACACAG CCCAGCTTGG AGCGAACGAC  6180
CTACACCGAA CTGAGATACC TACAGCGTGA GCATTGAGAA AGCGCCACGC TTCCCGAAGG  6240
GAGAAAGGCG GACAGGTATC CGGTAAGCGG CAGGGTCGGA ACAGGAGAGC GCACGAGGGA  6300
GCTTCCAGGG GGAAACGCCT GGTATCTTTA TAGTCCTGTC GGGTTTCGCC ACCTCTGACT  6360
TGAGGGTCGA TTTTTGTGAT GCTCGTCAGG GGGGCGGAGC CTATGGAAAA ACGCCAGCAA  6420
CGCGGCCTTT TGGGGTTCC CTGGCCTTTT GCTCACATGT TCTTTCCTGC  6480
GTTATCCCCT GATTCTGTGG ATAACCGTAT TACCGCCTTT GAGTGAGCTG ATACCGCTCG  6540
CCGCAGCCGA ACGACCGAGC GCAGCGAGTC AGTGAGCGAG GAAGCGGAAG AGCGCCCAAT  6600
ACGCAAAACCG CCTCTCCCCG CGCGTTGGCC GATTCATTAA TCCAGCTGGC ACGACAGGTT  6660
TCCCGACTGG AAAGCGGGCA GTGAGCGCAA CGCAATTAAT GTGAGTTACC TCACTCATTA  6720
GGCACCCCAG GCTTTACACT TTATGCTTCC GGCTCGTATG TTGTGTGGAA TTGTGAGCGG  6780
ATAACAATTT CACACAGGAA ACAGCTATGA CCATGATTAC GAATTAA                 6827
```

FIG. 4H

```
Glu Lys Ser Pro Glu Gln Arg Gly Arg Phe Arg Ala Met Val Glu Leu
  1                   5                  10                  15
Ala Arg Leu Asp Arg Arg Arg Pro Gly Ser Ser Asp Arg Val Leu Phe
                 20                  25                  30
Ala Arg Phe Ser Lys Thr Glu Gly Gly Ala Arg Arg Ala Ser Pro Asp
                 35                  40                  45
Gln Glu Ala Glu Asp Leu Trp Leu Ser Pro Leu Thr Met Glu Asp Leu
                 50                  55                  60
Val Cys Tyr Ser Phe Gln Val Ala Arg Gly Met Glu Phe Leu Ala Ser
                 65                  70                  75                  80
Arg Lys Cys Ile His Arg Asp Leu Ala Ala Arg Asn Ile Leu Leu Ser
                 85                  90                  95
Glu Ser Asp Val Val Lys Ile Cys Asp Phe Gly Leu Ala Arg Asp Ile
                100                 105                 110
Tyr Lys Asp Pro Asp Tyr Val Arg Lys Gly Ser Ala Arg Leu Pro Leu
                115                 120                 125
Lys Trp Met Ala Pro Glu Ser Ile Phe Asp Lys Val Tyr Thr Thr Gln
                130                 135                 140
Ser Asp Val Trp Ser Phe Gly Val Leu Leu Trp Glu Ile Phe Ser Leu
                145                 150                 155                 160
Gly Ala Ser Pro Tyr Pro Gly Val Gln Ile Asn Glu Glu Phe Cys Gln
                165                 170                 175
Arg Leu Arg Asp Gly Thr Arg Met Arg Met Ala Pro Glu Leu Ala Thr Pro
                180                 185                 190
```

FIG. 4I

Ala Ile Arg Arg Ile Met Leu Asn Cys Trp Ser Gly Asp Pro Lys Ala
195                         200                         205

Arg Pro Ala Phe Ser Glu Leu Val Glu Ile Leu Gly Asp Leu Leu Gln
210                         215                         220

Gly Arg Gly Leu Gln Glu Glu Glu Val Cys Met Ala Pro Arg Ser
225                         230                         235         240

Ser Gln Ser Ser Glu Gly Ser Phe Ser Gln Val Ser Thr Met Ala
245                         250                         255

Leu His Ile Ala Gln Ala Asp Ala Glu Asp Ser Pro Pro Ser Leu Gln
260                         265                         270

Arg His Ser Leu Ala Ala Arg Tyr Tyr Asn Trp Val Ser Phe Pro Gly
275                         280                         285

Cys Leu Ala Arg Gly Ala Glu Thr Arg Gly Ser Ser Arg Met Lys Thr
290                         295                         300

Phe Glu Glu Phe Pro Thr Pro Met Thr Pro Thr Thr Tyr Lys Gly Ser Val Asp
305                         310                         315         320

Asn Gln Thr Asp Ser Gly Met Val Leu Ala Ser Glu Glu Cys Glu Gln
325                         330                         335

Ile Glu Ser Arg Tyr Arg Gln Glu Ser Gly Phe Arg *
340                         345

FIG. 5A

| | | | | |
|---|---|---|---|---|
| TTCGAGCTCG | CCCGACATTG | ATTATTGACT | AGTAATCAAT | TACGGGTCA | 60 |
| TTAGTTCATA | GCCCATATAT | GGAGTTCCGC | GTTACATAAC | TTACGGTAAA | 120 |
| GGCTGACCGC | CCAACGACCC | CCGCCCATTG | ACGTCAATAA | TGACGTATGT | 180 |
| ACGCCAATAG | GGACTTTCCA | TTGACGTCAA | TGGGTGGAGT | ATTTACGGTA | 240 |
| TTGGCAGTAC | ATCAAGTGTA | TCATATGCCA | AGTACGCCCC | CTATTGACGT | 300 |
| AAATGGCCCG | CCTGGCATTA | TGCCCAGTAC | ATGACCTTAT | GGGACTTTCC | 360 |
| TACATCTACG | TATTAGTCAT | CGCTATTACC | ATGGTGATGC | GGTTTTGGCA | 420 |
| GGGCGTGGAT | AGCGGTTTGA | CTCACGGGGA | TTTCCAAGTC | TCCACCCCAT | 480 |
| GGAGTTTGT | TTTGGCACCA | AAATCAACGG | GACTTTCCAA | AATGTCGTAA | 540 |
| CCATTGACGC | AAATGGGCGG | TAGGCGTGTA | CGGTGGGAGG | TCTATATAAG | 600 |
| TTAGTGAACC | GTCAGATCGC | CTGGAGACGC | CATCCACGCT | GTTTTGACCT | 660 |
| CACCGGGACC | GATCCAGCCT | CCGCGGCCGG | GAACGGTGCA | TTGGAACGCG | 720 |
| GCCAAGAGTG | ACGTAAGTAC | CGCCTATAGA | GTCTATAGGC | CCACTTGGCT | 780 |
| GCGGCTACAA | TTAATACATA | ACCTTATGTA | TCATACACAT | ACGATTAAGG | 840 |
| GAATAACATC | CACTTTGCCT | TTCTCTCCAC | AGGTGTCCAC | TCCCAGTTCC | 900 |
| CGGTTCTATC | GATTGAATTC | CCCGGGGATC | CTCTAGAGAT | CCCTCGACCT | 960 |
| TTTTTTTTT | TTTTTGTAGG | CCAAAGGGTA | CTTCTTTTTC | TTTATTAATT | 1020 |

| |
|---|
| TACGGGTCA |
| TGGCCCGCCT |
| TCCCATAGTA |
| AACTGCCCAC |
| CAATGACGGT |
| TACTTGGCAG |
| GTACATCAAT |
| TGACGTCAAT |
| CAACTCCGCC |
| CAGAGCTCGT |
| CCATAGAAGA |
| GATTCCCCGT |
| TCGTTAGAAC |
| TGACACTATA |
| AACTGCACCT |
| CGAGTCGACT |
| ACTCAGAAGT |

FIG. 5B

```
CTAGGCCACA GCAATCTACT GTTCTCCTCT CATTTTCCTA AACTATTTTG ATACCTATTT    1080
CTCAGACTTT ATGGGCTATT AGACATTTCT CACATTTCCA TAGATAATAA CTCATCCGTT    1140
TTGCAACCTG ATTCTCAATA TTAAGAGATT AAAACTAATG TATATGACTC TCAGTTGACA    1200
CATACTGAAG TACAGAAAAA TTCCATCATT TCCTTCTGCA AAATGAAAAA GACTTCGTTT    1260
TCTCAACAGC TGCATCATTT TTTTATGCAT AGAAAAAAAT GTGCAATTAC TCCAAGTACA    1320
ATCAAGTCAT TTAACATGGC TTTACCATCA TTGTAGTTAC AGGATATTTT AAAAGAGAAA    1380
AAAAAATCTC AAAGCACAGG TCCTGCTGTG CAGCAAAGCA ATCAAATTCC TTCATAATAA    1440
CAGCCTGATG GGATTCAGCA ATCTGAGGAA TAATGAATAA CCACTCTAAT CAGTAAACAG    1500
GAAAATGCTA CAACAGTCAC TGAGTAAAAA TTGGACTATC ATCTGTTGAT TCTCTTGATC    1560
GACATTTCAA ACAATAAATG GAAATGTAAG TATCTCTTAA AAAGAAAAAT AACTTGGTTT    1620
AGTGTGCTTA ATTTTACCAG GCAGTGAGGA AATTATATAT CACCTTGACT GTCCTGCAGT    1680
GTTGCCCAGT CAATAAAATG CACAAATAAT CTTTTTTCATA ATACATGGCC AACTTTATCC    1740
TATCACTTGA ATATGTCAGG ATAAACTGAT TGTGCAGTTG GTTGATAACA TTGTATTTTG    1800
GAATGGATTA TTTGAATTTG TTTTGCTACT TTATTATTTG ATATTCTTCT CCAGTGTTCA    1860
TCTTATGAAG TTATTTGCAT CTGAATATGA AGAGTCTGTT TCAAAATAGT CTTCAAGTTT    1920
CCAACGCAGT GTCTCAAATG TAGGTCGTTC CTTAGGCTCT GCATTCCAGC ACTCCAACAT    1980
GATGTTGTAA AATTGCTGTG GACAGTTGGA TGGTTGCCGGA AGTCTATAGT TTTGAGCCAA    2040
```

FIG. 5C

```
CATCTGGATT ACCTGGGCAC CTGTCATACC ACTGTAAGGC ATTTTGCCAT AAGTAATGAT   2100
TTCATAAAGA AGGATTCCAA ATGACCATAC ATCGGACTTA ATGCTGAATT TATTACTACG   2160
AATGGCTTCG GGCGCAGTCC ACTTCACCGG CAGCTTTATT TCGTGTCTAG ATTCATAGAT   2220
GTCTTCATTA TCTACCTTAA AAACTCTGGC AAGTCCAAAA TCTGCTACTT TGTAGATATT   2280
ATGTTCACCA ACGAGGACAT TTCTGGCAGC CAGATCTCTG TGAATGTAGT TCCGAGACTC   2340
CAGATAGGCC ATTCCAGAGG CAACCTGTGC CGCCATGTCT ACCTGTTGAG TCAGATGGAT   2400
TTTTGATCCA GTGTCATTTT GGAGATATTC TTGCAGACTT CCATGTCTCA TCAACTCTGT   2460
AATAATATAA ATTGGATCTT CTAAAGTGCA AACAGCATAA AGCTGGATAA GCTTTGGATG   2520
TCTTAGGTTC TTCATTATCT GTGCCTCCCT CAGGAAGTCA TTTGGATCCA TTGAACCTGG   2580
TTTTAATGTT TTCACTGCTA CTGGAGTGGT ATTGTTCCAC AGACCTTCCC ATACTTCGCC   2640
AAACTGACCA GATCCCAATC GCTTCAGAAG CTGTATGGAG TTGCGGTCTA TCTCCCATTG   2700
GTCCACGGTT TTATACGACA AGCTGGGACC TGGATCTTTA AGCATGGTTT   2760
CCCCAGCTTG ACACACAGGC CGTCACTTGT CTTGGTGTAG TGGCTCACAA ATTCGTTCAG   2820
TGTTGAAAAG ATTCTTCTTC GCGTGAGAAA AAATCCCCCT TCATCCAGTC TTTTAATTCT   2880
GTAGTGTTTT ACAACTGCTC CATCTAAAAC TGAAAGAGAG AATTCTCCTT TTTGGCTTTC   2940
ACTTTCTCTG ATTAGAAAGG AACCGGTCTT GTTTTCTGAA TATAATAGTT GTTTCTCTGC   3000
ATCTGATCTT CCGATTGCTC CAAAGAACCA CGGCTCTGCC TGTAGGCTTC TGTCCTCAGC   3060
```

FIG. 5D

```
CACGTAGTTA GAAGGAATAT AGCCTTGTAG TTGCTGACTG GAGCCATCTC GTCTTTTCTC    3120
CAAGTGTCTG GCAAACCACC AGCCCTCATG CAAAGTGTCC AGAACTTGAA GTTTGTCACC    3180
TGCTCGGAAG CTCAAGTCCT CAGCAGTCCG AGCCTGGTAA TCAAACAAAG CCACAAAGTA    3240
GTGGCCATGC CTCTGTGACT GGGGAGAGCA AAGGGCCCCT GGATTTTCAA TCACGGTTGA    3300
CTTGTCTGCC TCCGTGGACA ACAGGGGAG ATAGGGTTCT AGTACTCCCC AGAGCCTCTG    3360
ACAGATGTTG CTCATTGTGC CTTGGTGGGG AGAAGAGGAG CAGGGCTTCT CCCTCTCCCC    3420
TTAGTCTCTG CGATCCACCT TATCTTCCTT CACCAGGCAA CTTTGAAGTC AGCACCAACT    3480
CACCATACTT CGGAGAGTAT GCAAAGTCCC GTTTCAGATC AGTCCAGCAG CTGGGTTGCA    3540
GCAAGTCCTA CCTGGAGAGA CTTACCGGCT TGCTTTCTGT GGCTGGAGGT GCTACCCCGA    3600
GGCAAAACTG AGCAGGAGCT GGGCAGCTGC TCACTAGGAA GGTGTCTTTT CTTCTTATCT    3660
GCTTAAGAAT CCCACACAA AAATAAAATA AAATTAAAAG GGCTTTATTT AGACAAATAT    3720
CTGAGAACAG AATGGTGCCA TCTTGCCTTT TGTCCCAATA AAAAGTTAGC AAGAGGAAGC    3780
TACTAACCCC TGGTAAAACC TCCACGTCTT GCTTTCGCCA GGGTCGACTC GAGGGATCTT    3840
CCATACCTAC CAGTTCTGCG CCTGCAGGTC GCGGCCGCGA CTCTAGAGTC GACCTGCAGA    3900
AGCTTGGCCG CCATGCCCA ACTTGTTTAT TGCAGCTTAT AATGGTTACA AATAAAGCAA    3960
TAGCATCACA AATTTCACAA ATAAAGCATT TTTTTCACTG CATTCTAGTT GTGGTTTGTC    4020
CAAACTCATC AATGTATCTT ATCATGTCTG GATCGGGAAT TAATTCGGCG CAGCACCATG    4080
```

FIG. 5E

```
GCCTGAAATA ACCTCTGAAA GAGGAACTTG GTTAGGTACC TTCTGAGGCG GAAAGAACCA 4140
GCTGTGGAAT GTGTGTCAGT TAGGGTGTGG AAAGTCCCCA GGCTCCCCAG CAGGCAGAAG 4200
TATGCAAAGC ATGCATCTCA ATTAGTCAGC AACCAGGTGT GGAAAGTCCC CAGGCTCCCC 4260
AGCAGGCAGA AGTATGCAAA GCATGCATCT CAATTAGTCA GCAACCATAG TCCCGCCCCT 4320
AACTCCGCCC ATCCCGCCCC TAACTCCGCC CAGTTCCGCC CATTCTCCGC CCCATGGCTG 4380
ACTAATTTTT TTTATTTATG CAGAGGCCGA GGCCGCCTCG GCCTCTGAGC TATTCCAGAA 4440
GTAGTGAGGA GGCTTTTTG GAGGCCTAGG CTTTTGCAAA AAGCTGTTAA CAGCTTGGCA 4500
CTGGCCGTCG TTTTACAACG TCGTGACTGG GAAAACCCTG GCGTTACCCA ACTTAATGC 4560
CTTGCAGCAC ATCCCCCTTT CGCCAGCTGG CGTAATAGCG AAGAGGCCCG CACCGATCGC 4620
CCTTCCCAAC AGTTGCGCAG CCTGAATGGC GAATGGCGCC TGATGCGGTA TTTTCTCCTT 4680
ACGCATCTGT GCGGTATTTC ACACCGCATA CGTCAAAGCA ACCATAGTAC GCGCCCTGTA 4740
GCGGCGCATT AAGCGCGGCG GGTGTGGTGG TTACGCGCAG CGTGACCGCT ACACTTGCCA 4800
GCGCCCTAGC GCCCGCTCCT TTCGCTTTCT TCCCTTCCTT TCTCGCCACG TTCGCCGGCT 4860
TTCCCCGTCA AGCTCTAAAT CGGGGGCTCC CTTTAGGGTT CCGATTTAGT GCTTTACGGC 4920
ACCTCGACCC CAAAAAACTT GATTTGGGTG ATGGTTCACG TAGTGGGCCA TCGCCCTGAT 4980
AGACGGTTTT TCGCCCTTTG ACGTTGGAGT CCACGTTCTT TAATAGTGGA CTCTTGTTCC 5040
AAACTGGAAC AACACTCAAC CCTATCTCGG GCTATTCTTT TGATTTATAA GGGATTTTGC 5100
```

FIG. 5F

```
CGATTTCGGC CTATTGGTTA AAAAATGAGC TGATTAACA AAAATTAAC GCGAATTTTA    5160
ACAAAATATT AACGTTTACA ATTTATGGT GCACTCTCAG TACAATCTGC TCTGATGCCG   5220
CATAGTTAAG CCAGCCCCGA CACCCGCCAA CACCCGCTGA CGGGCCCTGA CGGGCTTGTC  5280
TGCTCCCGGC ATCCGCTTAC AGACAAGCTG TGACCGTCTC CGGGAGCTGC ATGTGTCAGA  5340
GGTTTTCACC GTCATCACCG AAACGCGCGA GACGAAAGGG CCTCGTGATA CGCCTATTTT  5400
TATAGTTAA TGTCATGATA ATAATGGTTT CTTAGACGTC AGGTGGCACT TTTCGGGGAA   5460
ATGTGCGCGG AACCCCTATT TGTTTATTTT TCTAAATACA TTCAAATATG TATCCGCTCA  5520
TGAGACAATA ACCCTGATAA ATGCTTCAAT AATATTGAAA AAGGAAGAGT ATGAGTATTC  5580
AACATTTCCG TGTCGCCCTT ATTCCCTTTT TTGCGGCATT TTGCCTTCCT GTTTTTGCTC  5640
ACCCAGAAAC GCTGGTGAAA GTAAAAGATG CTGAAGATCA GTTGGGTGCA CGAGTGGGTT  5700
ACATCGAACT GGATCTCAAC AGCGGTAAGA TCCTTGAGAG TTTTCGCCCC GAAGAACGTT  5760
TTCCAATGAT GAGCACTTTT AAAGTTCTGC TATGTGGCGC GGTATTATCC CGTATTGACG  5820
CCGGGCAAGA GCAACTCGGT CGCCGCATAC ACTATTCTCA GAATGACTTG GTTGAGTACT  5880
CACCAGTCAC AGAAAAGCAT CTTACGGATG GCATGACAGT AAGAGAATTA TGCAGTGCTG  5940
CCATAACCAT GAGTGATAAC ACTGCGGCCA ACTTACTTCT GACAACGATC GGAGGACCGA  6000
AGGAGCTAAC CGCTTTTTTG CACAACATGG GGGATCATGT AACTCGCCTT GATCGTTGGG  6060
AACCGGAGCT GAATGAAGCC ATACCAAACG ACGAGCGTGA CACCACGATG CCTGTAGCAA  6120
```

FIG. 5G

```
TGGCAACAAC GTTGCGCAAA CTATTAACTG GCGAACTACT TACTCTAGCT TCCCGGCAAC    6180
AATTAATAGA CTGGATGGAG GCGGATAAAG TTGCAGGACC ACTTCTGCGC TCGGCCCTTC    6240
CGGCTGGCTG GTTTATTGCT GATAAATCTG GAGCCGGTGA GCGTGGGTCT CGCGGTATCA    6300
TTGCAGCACT GGGGCCAGAT GGTAAGCCCT CCCGTATCGT AGTTATCTAC ACGACGGGGA    6360
GTCAGGCAAC TATGGATGAA CGAAATAGAC AGATCGCTGA GATAGGTGCC TCACTGATTA    6420
AGCATTGGTA ACTGTCAGAC CAAGTTTACT CATATATACT TTAGATTGAT TTAAAACTTC    6480
ATTTTTAATT TAAAAGGATC TAGGTGAAGA TCCTTTTTGA TAATCTCATG ACCAAAATCC    6540
CTTAACGTGA GTTTTCGTTC CACTGAGCGT CAGACCCCGT AGAAAAGATC AAAGGATCTT    6600
CTTGAGATCC TTTTTTTCTG CGCGTAATCT GCTGCTTGCA AACAAAAAAA CCACCGCTAC    6660
CAGCGGTGGT TTGTTTGCCG GATCAAGAGC TACCAACTCT TTTTCCGAAG GTAACTGGCT    6720
TCAGCAGAGC GCAGATACCA AATACTGTTC TTCTAGTGTA GCCGTAGTTA GGCCACCACT    6780
TCAAGAACTC TGTAGCACCG CCTACATACC TCGCTCTGCT AATCCTGTTA CCAGTGGCTG    6840
CTGCCAGTGG CGATAAGTCG TGTCTTACCG GGTTGGACTC AAGACGATAG TTACCGGATA    6900
AGGCGCAGCG GTCGGGCTGA ACGGGGGGTT CGTGCACACA GCCCAGCTTG GAGCGAACGA    6960
CCTACACCGA ACTGAGATAC CTACAGCGTG AGCTATGAGA AAGCGCCACG CTTCCCGAAG    7020
GGAGAAAGGC GGACAGGTAT CCGGTAAGCG GCAGGGTCGG AACAGGAGAG CGCACGAGGG    7080
AGCTTCCAGG GGGAAACGCC TGGTATCTTT ATAGTCCTGT CGGGTTTCGC CACCTCTGAC    7140
```

FIG. 5H

```
TTGAGCGTCG ATTTTTGTGA TGCTCGTCAG GGGGGCGGAG CCTATGGAAA AACGCCAGCA   7200
ACGCGGCCTT TTTACGGTTC CTGGCCTTTT GCTGGCCTTT TGCTCACATG TTCTTTCCTG   7260
CGTTATCCCC TGATTCTGTG GATAACCGTA TTACCGCCTT TGAGTGAGCT GATACCGCTC   7320
GCCGCAGCCG AACGACCGAG CGCAGCGAGT CAGTGAGCGA GGAAGCGGAA GAGCGCCCAA   7380
TACGCAAACC GCCTCTCCCC GCGCGTTGGC CGATTCATTA ATGCAGCTGG CACGACAGGT   7440
TTCCCGACTG GAAAGCGGGC AGTGAGCGCA ACGCAATTAA TGTGAGTTAG CTCACTCATT   7500
AGGCACCCCA GGCTTTACAC TTTATGCTTC CGGCTCGTAT GTTGTGTGGA ATTGTGAGCG   7560
GATAACAATT TCACACAGGA AACAGCTATG ACATGATTAC GAATTAA                 7607
```

FIG. 5I

```
Met Ser Asn Ile Cys Gln Arg Leu Trp Glu Tyr Leu Glu Pro Tyr Leu
 1                   5                  10                  15
Pro Cys Leu Ser Thr Glu Ala Asp Lys Ser Thr Val Ile Glu Asn Pro
                    20                  25                  30
Gly Ala Leu Cys Ser Pro Gln Ser Gln Arg His Gly His Tyr Phe Val
                35                  40                  45
Ala Leu Phe Asp Tyr Gln Ala Arg Thr Ala Glu Asp Leu Ser Phe Arg
            50                  55                  60
Ala Gly Asp Lys Leu Gln Val Leu Asp Thr Leu His Glu Gly Trp Trp
        65                  70                  75              80
Phe Ala Arg His Leu Glu Lys Arg Arg Asp Gly Ser Ser Gln Gln Leu
                    85                  90                  95
Gln Gly Tyr Ile Pro Ser Asn Tyr Val Ala Glu Asp Arg Ser Leu Gln
                100                 105                 110
Ala Glu Pro Trp Phe Phe Gly Ala Ile Gly Arg Ser Asp Ala Glu Lys
            115                 120                 125
Gln Leu Leu Tyr Ser Glu Asn Lys Thr Gly Ser Phe Leu Ile Arg Glu
        130                 135                 140
Ser Glu Ser Gln Lys Gly Glu Phe Ser Leu Ser Val Leu Asp Gly Ala
    145                 150                 155             160
Val Val Lys His Tyr Arg Ile Lys Arg Leu Asp Glu Gly Gly Phe Phe
                165                 170                 175
Leu Thr Arg Arg Ile Phe Ser Thr Leu Asn Glu Phe Val Ser His
                180                 185                 190
```

FIG. 5J

Tyr Thr Lys Thr Ser Asp Gly Leu Cys Val Lys Leu Gly Lys Pro Cys
            195                 200                 205

Leu Lys Ile Gln Val Pro Ala Pro Phe Asp Leu Ser Tyr Lys Thr Val
            210                 215                 220

Asp Gln Trp Glu Ile Asp Arg Asn Ser Ile Gln Leu Leu Lys Arg Leu
225                 230                 235                 240

Gly Ser Gly Gln Phe Gly Glu Val Trp Glu Gly Leu Trp Asn Asn Thr
            245                 250                 255

Thr Pro Val Ala Val Lys Thr Leu Lys Pro Gly Ser Met Asp Pro Asn
            260                 265                 270

Asp Phe Leu Arg Glu Ala Gln Ile Met Lys Asn Leu Arg His Pro Lys
            275                 280                 285

Leu Ile Gln Leu Tyr Ala Val Cys Thr Leu Glu Asp Pro Ile Tyr Ile
            290                 295                 300

Ile Thr Glu Leu Met Arg His Gly Ser Leu Gln Tyr Leu Gln Asn
305                 310                 315                 320

Asp Thr Gly Ser Lys Ile His Leu Thr Gln Val Asp Met Ala Ala
            325                 330                 335

Gln Val Ala Ser Gly Met Ala Tyr Leu Glu Ser Arg Asn Tyr Ile His
            340                 345                 350

Arg Asp Leu Ala Ala Arg Asn Val Leu Val Gly Glu His Asn Ile Tyr
            355                 360                 365

Lys Val Ala Asp Phe Gly Leu Ala Arg Val Phe Lys Val Asp Asn Glu
370                 375                 380

FIG. 5K

Asp Ile Tyr Glu Ser Arg His Glu Ile Lys Leu Pro Val Lys Trp Thr
385                 390                 395                 400

Ala Pro Glu Ala Ile Arg Ser Asn Lys Phe Ser Ile Lys Ser Asp Val
            405                 410                 415

Trp Ser Phe Gly Ile Leu Leu Tyr Glu Ile Ile Thr Tyr Gly Lys Met
            420                 425                 430

Pro Tyr Ser Gly Met Thr Gly Ala Gln Val Ile Gln Met Leu Ala Gln
            435                 440                 445

Asn Tyr Arg Leu Pro Gln Pro Ser Asn Cys Pro Gln Gln Phe Tyr Asn
450                 455                 460

Ile Met Leu Glu Cys Trp Asn Ala Glu Pro Lys Glu Arg Pro Thr Phe
465                 470                 475                 480

Glu Thr Leu Arg Trp Lys Leu Glu Asp Tyr Phe Glu Thr Asp Ser Ser
            485                 490                 495

Tyr Ser Asp Ala Asn Asn Phe Ile Arg *
500                 505

FIG. 6

```
GCGGCCGCAG AGAAAGCAGA GGATGGGGCT TAGCAGCTGG CAGAGCCAGG AGCGGGGAGG    60
TAGCAGAAAG ACCACAAGTA CAAAGAAGTC CTGAAACTTT GGTTTTGCTG CTGCAGCCCA   120
TTGAGAGTGA CGACATGGAG CACAAGACCC TGAAGATCAC CGACTTTGGC CTGGCCCGAG   180
AGTGGCACAA AACCACACAA ATGAGTGCCG CNGGCACCTA CNCCTGGATG GCTCCTGAGG   240
TTATCAAGGC CTCCACCTTC TCTAAGGGCA GTGACGTCTG GAGTTTTGGG GTGCTGCTGT   300
GGGAACTGCT GACCGGGGAG NTGCCATACC GTGGCATTGA CTGCCTTGCT GTGGCCTATG   360
GCGTAGCTGT TAACAAGCTC ACACTGCCAT CCATCCACCT GGCC                    404
```

FIG. 7A

```
ATGAGAGCGT TGGCGCGCGA CGGCGGCCAG CTGCCGCTGC TCGTTGTTTT TTCTGCAATG    60
ATATTTGGGA CTATTACAAA TCAAGATCTG CCTGTGATCA AGTGTGTTTT AATCAATCAT   120
AAGAACAATG ATTCATCAGT GGGGAAGTCA TCATCATATC CCATGGTATC AGAATCCCCG   180
GAAGACCTCG GGTGTGCGTT GAGACCCCAG AGCTCAGGA CAGTGTACGA AGCTGCCGCT    240
GTGGAAGTGG ATGTATCTGC TTCCATCACA CTGCAAGTGC TGGTCGATGC CCCAGGAAC    300
ATTTCCTGTC TCTGGGTCTT TAAGCACAGC TCCCTGAATT GCCAGCCACA TTTTGATTTA   360
CAAAACAGAG GAGTTGTTTC CATGGTCATT TTGAAAATGA CAGAAACCCA AGCTGGAGAA   420
TACCTACTTT TTATTCAGAG TGAAGCTACC AATTACACAA TATTGTTTAC AGTGAGTATA   480
AGAAATACCC TGCTTTACAC ATTAAGAAGA CCTTACTTTA GAAAAATGAA AAACCAGGAC   540
GCCCTGGTCT GCATATCTGA GAGCGTTCCA GAGCGGATCC TGGAATGGGT GCTTTGCGAT   600
TCACAGGGGG AAAGCTGTAA AGAAGAAAGT CCAGCTGTTG TTAAAAAGGA GGAAAAAGTG   660
CTTCATGAAT TATTTGGGAC GGACATAAGG TGCTGTGCCA GAAATGAACT GGGCAGGGAA   720
TGCACCAGGC TGTTCACAAT AGATCTAAAT CAAACTCCTC AGACCACATT GCCACAATTA   780
TTTCTTAAAG TAGGGAACC CTTATGGATA AGGTGCAAAG CTGTTCATGT GAACCATGA    840
TTCGGGCTCA CCTGGGAATT AGAAAACAAA GCACTCGAGG AGGGCAACTA CTTTGAGATG   900
AGTACCTATT CAACAAACAG AACTATGATA CGGATTCTGT TTGCTTTTGT ATCATCAGTG   960
GCAAGAAACG ACACCGGATA CTACACTTGT TCCTCTTCAA AGCATCCCAG TCAATCAGCT  1020
TTGGTTACCA TCGTAGAAAA GGGATTTATA AATGCTACCA ATTCAAGTGA AGATTATGAA  1080
```

FIG. 7B

```
ATTGACCAAT ATGAAGAGTT TTGTTTTTCT GTCAGGTTTA AAGCCTACCC ACAAATCAGA    1140
TGTACGTGGA CCTTCTCTCG AAAATCATTT CCTTGTGAGC AAAAGGGTCT TGATAACGGA    1200
TACAGCATAT CCAAGTTTTG CAATCATAAG CACCAGCCAG GAGAATATAT ATTCCATGCA    1260
GAAAATGATG ATGCCCAATT TACCAAAATG TTCACGCTGT ATATAAGAAG GAAACCTCAA    1320
GTCCTCGCAG AAGCTTCGGC AAGTCAGGCG TCCTGTTTCT CGGATGGATA CCCATTACCA    1380
TCTTGGACCT GGAAGAAGTG TTCAGACAAG TCTCCCAACT GCACAGAAGA GATCACAGAA    1440
GGAGTCTGGA ATAGAAAGGC TAACAGAAAA GTGTTTGGAC AGTGGGTGTC GAGCAGTACT    1500
CTAAACATGA GTGAAGCCAT AAAAGGGTTC CTGGTCAAGT GCTGTGCATA CAATTCCCTT    1560
GGCACATCTT GTGAGACGAT CCTTTTAAAC TCTCCAGGCC CCTTCCCTTT CATCCAAGAC    1620
AACATCTCAT TCTATGCAAC AATTGGTGTT TGTCTCCCTCT TCATTGTCGT TTTAACCCTG    1680
CTAATTTGTC ACAAGTACAA AAAGCAATTT AGTATGAAA GCCAGCTACA GATGGTACAG    1740
GTGACCGGAT CCTCAGATTA TGAGTACTTC TACGTTGATT TCAGAGAATA TGAATATGAT    1800
GTCAAATGGG AGTTTCCAAG AGAAAATTTA GAGTTGGGA AGTACTAGG ATCAGGTGCT    1860
TTTGGAAAAG TGATGAACGC AACAGCTTAT GGAATTAGCA AAACAGAGT CTCAATCCAG    1920
GTTACCGTCA AAATGCTGAA AGAAAAAGCA GACAGCTCTG AAAGAGAGGC ACTCATGTCA    1980
GAACTCAAGA TGATGACCCA GCTGGGAAGC CACGAGAATA TTGTGAACCT GCTGGGGCG    2040
TGCACACTGT CAGGACCAAT TTACTTGATT TTTGAATACT GTTGCTATGG TGATCTTCTC    2100
AACTATCTAA GAAGTAAAAG AGAAAAATTT CACAGACTT GGACAGAGAT TTTCAAGGAA    2160
```

FIG. 7C

```
CACAATTTCA GTTTTTACCC CACTTTCCAA TCACATCCAA ATTCCAGCAT GCCTGGTTCA   2220
AGAGAAGTTC AGATACACCC GGACTCGGAT CAAATCTCAG GGCTTCATGG GAATTCATTT   2280
CACTCTGAAG ATGAAATTGA ATATGAAAAC CAAAAAAGGC TGGAAGAAGA GGAGGACTTG   2340
AATGTGCTTA CATTTGAAGA TCTTCTTTGC TTTGCATATC AAGTTGCCAA AGGAATGGAA   2400
TTTCTGGAAT TTAAGTCGTG TGTTCACAGA GACCTGGCCG CCAGAACGT GCTTGTCACC    2460
CACGGGAAAG TGGTGAAGAT ATGTGACTTT GGATTGGCTC GAGATATCAT GAGTGATTCC   2520
AACTATGTTG TCAGGGGCAA TGCCCGTCTG CCTGTAAAAT GGATGGCCCC CGAAAGCCTG   2580
TTTGAAGGCA TCTACACCAT TAAGAGTGAT GTCTGGTCAT ATGGAATATT ACTGTGGGAA   2640
ATCTTCTCAC TTGGTGTGAA TCCTTACCCT GGCATTCCGG TTGATGCTAA CTTCTACAAA   2700
CTGATTCAAA ATGGATTTAA AATGGATCAG CCATTTTATG CTACAGAAGA AATATACATT   2760
ATAATGCAAT CCTGCTGGGC TTTTGACTCA AGGAAACGGC CATCCTTCCC TAATTTGACT   2820
TCGTTTTTAG GATGTCAGCT GGCAGATGCA GAAGAAGCGA TGTATCAGAA TGTGGATGGC   2880
CGTGTTTCGG AATGTCCTCA CACCTACCAA AACAGGCGAC CTTTCAGCAG AGAGATGGAT   2940
TTGGGGCTAC TCTCTCCGCA GGCTCAGTC GAAGATTCGT AGAGGAACAA TTTAGTTTTA    3000
AGGACTTCAT CCCTCCACCT ATCCCTAACA GGCTGTAGAT TACCAAAACA AGGTAATTT    3060
CATCACTAAA AGAAAATCTA TTATCAACTG CTGCTTCACC AGACTTTTCT CTAGAGAGCG   3120
```

FIG. 8A

```
TCGGCGTCCA CCCGCCCAGG GAGAGTCAGA CCTGGGGGGG CGAGGGCCCC CCAAACTCAG         60

TTCGGATCCT ACCCGAGTGA GGCGGCGCC ATG GAG CTC CGG GTG CTG CTC TGC         113
                                Met Glu Leu Arg Val Leu Leu Cys
                                 1               5

TGG GCT TCG TTG GCC GCA GCT TTG GAA GAG CTG GAA GAG ACC CTG AAC ACA AAA  161
Trp Ala Ser Leu Ala Ala Ala Leu Glu Glu Leu Glu Glu Thr Leu Asn Thr Lys
            10                  15                  20

TTG GAA ACT GCT GAT CTG AAG TGG ACA TTC CCT CAG GTG GAC GGG              209
Leu Glu Thr Ala Asp Leu Lys Trp Thr Phe Pro Gln Val Asp Gly
25                  30                  35                  40

CAG TGG GAG GAA CTG GGC AGC GAT GAG CAG CAG CAC AGC GTG CGC              257
Gln Trp Glu Glu Leu Gly Ser Asp Glu Gln Gln His Ser Val Arg
                45                  50                  55

ACC TAC GAA GTG TGT GAC GTG CAG CGT GCC CCG GGC CAG GCC CAC TGG          305
Thr Tyr Glu Val Cys Asp Val Gln Arg Ala Pro Gly Gln Ala His Trp
                    60                  65                  70

CTT CGC ACA GGT TGG GTC CCA CGG GGC CGG GCC GTC CAC GTG TAC GCC          353
Leu Arg Thr Gly Trp Val Pro Arg Gly Arg Ala Val His Val Tyr Ala
                    75                  80                  85

ACG CTG CGC TTC ACC ATG CTC GAG TGC CTG TCC CTG CCT CGG GCT GGG          401
Thr Leu Arg Phe Thr Met Leu Glu Cys Leu Ser Leu Pro Arg Ala Gly
                    90                  95                 100

CGC TCC TGC AAG GAG ACC TTC ACC GTC TTC TAC TAT GAG TAC GAT GCG          449
Arg Ser Cys Lys Glu Thr Phe Thr Val Phe Tyr Tyr Glu Tyr Asp Ala
105                 110                 115                 120

GAC ACG GCC ACG CTC ACG GCC CCA GCC TGG ATG GAG AAC CCC TAC ATC          497
Asp Thr Ala Thr Leu Thr Ala Pro Ala Trp Met Glu Asn Pro Tyr Ile
            125                 130                 135
```

FIG. 8B

```
AAG GTG GAC ACG GTG GCC GCG GAG CAT CTC ACC CGG AAG CGC CCT GGG    545
Lys Val Asp Thr Val Ala Ala Glu His Leu Thr Arg Lys Arg Pro Gly
        140                     145                     150

GCC GAG GCC ACC GGG AAG GTG AAT GTC AAG ACG CTG CGT CTG GGA CCG    593
Ala Glu Ala Thr Gly Lys Val Asn Val Lys Thr Leu Arg Leu Gly Pro
        155                     160                     165

CTC AGC AAG GCT GGC TTC TAC GCC TTC CAG GAC CAG GGT GCC TGC        641
Leu Ser Lys Ala Gly Phe Tyr Ala Phe Gln Asp Gln Gly Ala Cys
        170                     175                     180

ATG GCC CTG CTA TCC CTG CAC CTC TTC TAC AAA AAG TGC GCC CAG CTG    689
Met Ala Leu Leu Ser Leu His Leu Phe Tyr Lys Lys Cys Ala Gln Leu
        185                     190                     195        200

ACT GTG AAC CTG ACT CGA TTC CCG GAG ACT GTG GTG CCT CGG CTG GTT    737
Thr Val Asn Leu Thr Arg Phe Pro Glu Thr Val Val Pro Arg Leu Val
        205                     210                     215

GTG CCC GTG GCC AGC TGC GGT GAT GCC GTC GAG GAG CCC GCC CCT GGC    785
Val Pro Val Ala Ser Cys Gly Asp Ala Val Pro Ala Pro Gly
        220                     225                     230

CCC AGC CCC AGC CTC TAC TGC CGT GAG GAT GGC CAG TGG GCA GAA CAG    833
Pro Ser Pro Ser Leu Tyr Cys Arg Glu Asp Gly Gln Trp Ala Glu Gln
        235                     240                     245

CCG GTC ACG GGC TGC AGC TGT GCT CCG GGG TTC GAG GCA GCT GAG GGG    881
Pro Val Thr Gly Cys Ser Cys Ala Pro Gly Phe Glu Ala Ala Glu Gly
        250                     255                     260

AAC ACC AAG TGC CGA GCC CAG GGC CAG GGC ACC TTC AAG CCC CTG TCA    929
Asn Thr Lys Cys Arg Ala Gln Gly Thr Phe Lys Pro Leu Ser
        265                     270                     275        280
```

FIG. 8C

```
GGA GAA GGG TCC TGC CAG CCA TGC AAT AGC CAC TCT AAC ACC    977
Gly Glu Gly Ser Cys Gln Pro Cys Asn Ser His Ser Asn Thr
                285             290             295

ATT GGA TCA GCC GTC TGC CAG TGC GTC GGG TAC TTC CGG GCA CGC   1025
Ile Gly Ser Ala Val Cys Gln Cys Val Gly Tyr Phe Arg Ala Arg
            300             305             310

ACA GAC CCC CGG GGT GCA CCC TGC CYS ACC CCT CCT TCG GCT CCG CGG   1073
Thr Asp Pro Arg Gly Ala Pro Cys Thr Thr Pro Pro Ser Ala Pro Arg
            315             320             325

AGC GTG GTT TCC CGC CTG AAC GGC CTG TCC TCC CTG CAC CTG GAA TGG AGT   1121
Ser Val Val Ser Arg Leu Asn Gly Leu Ser Ser Leu His Leu Glu Trp Ser
            330             335             340

GCC CCC CTG GAG TCT GGT GGC CGA GAG GAC CTC ACC CTC TAC GCC CTC CGC   1169
Ala Pro Leu Glu Ser Gly Gly Arg Glu Asp Leu Thr Leu Tyr Ala Leu Arg
345             350             355             360

TGC CGG GAG TGC CGA CCC GGA GGC TCC TGT GCG CCC TGC GGG GGA GAC   1217
Cys Arg Glu Cys Arg Pro Gly Gly Ser Cys Ala Pro Cys Gly Gly Asp
            365             370             375

CTG ACT TTT GAC CCC CGG GGC CCC CGG GAC CTG GTG GAG CCC TGG GTG   1265
Leu Thr Phe Asp Pro Arg Gly Pro Arg Asp Leu Val Glu Pro Trp Val Val
            380             385             390

GTT CGA GGG CTA CGT CCT GAC TTC ACC TAT ACC TTT GAG GTC ACT GCA   1313
Val Arg Gly Leu Arg Pro Asp Phe Thr Tyr Thr Phe Glu Val Thr Ala
            395             400             405

TTG AAC GGG GTA TCC TCC TTA GCC ACG GGG CCC CCA TTT GAG CCT   1361
Leu Asn Gly Val Ser Ser Leu Ala Thr Gly Pro Val Pro Phe Glu Pro
410             415             420
```

FIG. 8D

```
GTC AAT GTC ACC ACT GAC CGA GAG GTA CCT CCT GCA GTG TCT GAC ATC   1409
Val Asn Val Thr Thr Asp Arg Glu Val Pro Pro Ala Val Ser Asp Ile
425                 430                 435                 440

CGG GTG ACG CGG TCC TCA CCC AGC AGC TTG AGC CTG GCC TGG GCT GTT   1457
Arg Val Thr Arg Ser Ser Pro Ser Ser Leu Ser Leu Ala Trp Ala Val
            445                 450                 455

CCC CGG GCA CCC AGT GGG GCT GTG CTG GAC TAC GAG GTC AAA TAC CAT   1505
Pro Arg Ala Pro Ser Gly Ala Val Leu Asp Tyr Glu Val Lys Tyr His
        460                 465                 470

GAG AAG GGC GCC GAG GGT CCC AGC AGC GTG CGG TTC CTG AAG ACG TCA   1553
Glu Lys Gly Ala Glu Gly Pro Ser Ser Val Arg Phe Leu Lys Thr Ser
    475                 480                 485

GAA AAC CGG GCA GAG CTG CGG GGG CTG AAG CGG GGA AGC TAC CTG       1601
Glu Asn Arg Ala Glu Leu Arg Gly Leu Lys Arg Gly Ala Ser Tyr Leu
490                 495                 500

GTG CAG GTA CGG GCG CGC TCT GAG GCC TAC GGG TAC GGG CCC TTC CAG   1649
Val Gln Val Arg Ala Arg Ser Glu Ala Gly Tyr Gly Pro Phe Gly Gln
505                 510                 515                 520

GAA CAT CAC AGC CAG ACC CAA CTG GAT GAG AGC GAG GGC TGG CGG GAG   1697
Glu His His Ser Gln Thr Gln Leu Asp Glu Ser Glu Gly Trp Arg Glu
            525                 530                 535

CAG CTG GCC CTG ATT GCG GCG ACG GCA GTC GTC GGT GTG GTC CTG GTC   1745
Gln Leu Ala Leu Ile Ala Gly Thr Ala Val Val Gly Val Val Leu Val
        540                 545                 550

CTG GTG GTC ATT GTC GCA GTT CTC TGC CTC AGG AAG CAG AGC AAT       1793
Leu Val Val Ile Val Ala Val Leu Cys Leu Arg Lys Gln Ser Asn
    555                 560                 565
```

FIG. 8E

```
GGG AGA GAA GCA GAA TAT TCG GAC AAA CAC GGA CAG TAT CTC ATC GGA   1841
Gly Arg Glu Ala Glu Tyr Ser Asp Lys His Gly Gln Tyr Leu Ile Gly
570                 575                 580

CAT GGT ACT AAG GTC TAC ATC GAC CCC TTC ACT GAA TAT GAC CCT AAT   1889
His Gly Thr Lys Val Tyr Ile Asp Pro Phe Thr Glu Tyr Asp Pro Asn
585                 590                 595                 600

GAG GCT GTG AGG GAA TTT GCA AAA GAG ATC GAT GTC TCC TAC GTC AAG   1937
Glu Ala Val Arg Glu Phe Ala Lys Glu Ile Asp Val Ser Tyr Val Lys
        605                 610                 615

ATT GAA GAG GTG ATT GGT GTG AGG GGT GCA GGT GAG TTT GGC GAG GTG   1985
Ile Glu Glu Val Ile Gly Val Arg Gly Ala Gly Glu Phe Gly Glu Val
    620                 625                 630

CGG CTC AAG GCC CCA GGG AAG AAG TGT GTG AGC TGT GTG GCA ATC AAG ACC   2033
Arg Leu Lys Ala Pro Gly Lys Lys Cys Val Ser Cys Val Ala Ile Lys Thr
635                 640                 645

CTG AAG GGT GGC TAC ACG GAG TTC TTT CTG AGC GAG   2081
Leu Lys Gly Gly Tyr Thr Glu Phe Phe Leu Ser Glu
650                 655                 660

GCC TCC ATC ATG GGC CAG TTC GAG CAC CCC AAT ATC ATC CGC CTG GAG   2129
Ala Ser Ile Met Gly Gln Phe Glu His Pro Asn Ile Ile Arg Leu Glu
665                 670                 675                 680

GGC GTG GTC ACC AAC AGC ATG CCC GTC ATG ATT CTC ACA GAG TTC ATG   2177
Gly Val Val Thr Asn Ser Met Pro Val Met Ile Leu Thr Glu Phe Met
        685                 690                 695

GAG AAC GGC GCC CTG GAC TCC TTC CTG CGG CTA AAC GAC GGA CAG TTC   2225
Glu Asn Gly Ala Leu Asp Ser Phe Leu Arg Leu Asn Asp Gly Gln Phe
    700                 705                 710
```

FIG. 8F

```
ACA GTC ATC CAG CTC GTG GGC ATG CTG CGG GGC ATC GCC TCG GGC ATG   2273
Thr Val Ile Gln Leu Val Gly Met Leu Arg Gly Ile Ala Ser Gly Met
         715                 720                 725

CGG TAC CTT GCC GAG ATG AGC TAC GTC CAC CGA GAC GAG CTG GCT CGC   2321
Arg Tyr Leu Ala Glu Met Ser Tyr Val His Arg Asp Glu Leu Ala Arg
         730                 735                 740

AAC ATC CTA GTC AAC AGC AAC CTC GTC TGC AAA GTG TCT GAC TTT GGC   2369
Asn Ile Leu Val Asn Ser Asn Leu Val Cys Lys Val Ser Asp Phe Gly
         745                 750                 755                 760

CTT TCC CGA TTC CTG GAG AAC TCT CCC GAT CCC ACC TAC ACG AGC       2417
Leu Ser Arg Phe Leu Glu Asn Ser Ser Asp Pro Thr Tyr Thr Ser
         765                 770                 775

TCC CTG GGA AAG ATT CCC ATC CGA TGG ACT GCC CCG GAG GCC ATT       2465
Ser Leu Gly Lys Ile Pro Ile Arg Trp Thr Ala Pro Glu Ala Ile
         780                 785                 790

GCC TTC CGG AAG TTC ACT TCC GCC AGT GAT GCC TGG AGT TAC GGG ATT   2513
Ala Phe Arg Lys Phe Thr Ser Ala Ser Asp Ala Trp Ser Tyr Gly Ile
         795                 800                 805

GTG ATG TGG GAG GTG ATG TCA TTT GGG GAG AGG CCG TAC TGG GAC ATG   2561
Val Met Trp Glu Val Met Ser Phe Gly Glu Arg Pro Tyr Trp Asp Met
         810                 815                 820

AGC AAT CAG GAC GTG ATC AAT GCC ATT GAA CAG GAC TAC CGG CTG CCC   2609
Ser Asn Gln Asp Val Ile Asn Ala Ile Glu Gln Asp Tyr Arg Leu Pro
         825                 830                 835                 840

CCG CCC CCA GAC TGT CCC ACC TCC CTC CAC CAG CTC ATG CTG GAC TGT   2657
Pro Pro Pro Asp Cys Pro Thr Ser Leu His Gln Leu Met Leu Asp Cys
         845                 850                 855
```

FIG. 8G

```
TGG CAG AAA GAC CGG AAT GCC CGG CCC TTC CCC CAG GTG GTC AGC       2705
Trp Gln Lys Asp Arg Asn Ala Arg Pro Phe Pro Gln Val Val Ser
            860                 865                 870

GCC CTG GAC AAG ATG ATC CGG AAC CCC GCC AGC CTC AAA ATC GTG GCC   2753
Ala Leu Asp Lys Met Ile Arg Asn Pro Ala Ser Leu Lys Ile Val Ala
        875                 880                 885

CGG GAG AAT GGC GGG GCC TCA CAC CCT CTC GAC CAG CGG CAG CCT       2801
Arg Glu Asn Gly Gly Ala Ser His Pro Leu Asp Gln Arg Gln Pro
            890                 895                 900

CAC TAC TCA GCT TTT GGC GTG TCT GGC GAG TGG CTT CGG GCC ATC AAA   2849
His Tyr Ser Ala Phe Gly Val Ser Gly Glu Trp Leu Arg Ala Ile Lys
        905                 910                 915                 920

ATG GGA AGA TAC GAA GAA AGT TTC GCA GCT GGC TTT GGC TCC TTC       2897
Met Gly Arg Tyr Glu Glu Ser Phe Ala Ala Gly Phe Gly Ser Phe
            925                 930                 935

GAG CTG GTC AGC CAG ATC TCT GCT GAG GAC CTG CGA ATC GGA GTC       2945
Glu Leu Val Ser Gln Ile Ser Ala Glu Asp Leu Arg Ile Gly Val
        940                 945                 950

ACT CTG GCG GGA CAC CAG AAG AAA ATC TTG GCC AGT GTC CAG CAC ATG   2993
Thr Leu Ala Gly His Gln Lys Lys Ile Leu Ala Ser Val Gln His Met
        955                 960                 965

AAG TCC CAG GCC AAG CCG GGT GGG ACA GGA GGA CCG GCC               3041
Lys Ser Gln Ala Lys Pro Gly Gly Thr Gly Gly Pro Ala
            970                 975                 980

CCG CAG TAC TGA CCT GCA GGA ACT CCC CAC CCC AGG GAC ACC GCC TCC   3089
Pro Gln Tyr *   Pro Ala Gly Thr Pro His Pro Arg Asp Thr Ala Ser
        985                 990                 995                 1000
```

FIG. 8H

```
CCA TTT TCC GGG GCA GAG TGG GGA CTC ACA GAG GCC CCC AGC CCT GTG      3137
Pro Phe Ser Gly Ala Glu Trp Gly Leu Thr Glu Ala Pro Ser Pro Val
                1005                                  1015

CCC CGC TGG ATT GCA CTT TGA GCC CGT GGG GTG AGG AGT TGG CAA TTT      3185
Pro Arg Trp Ile Ala Leu  *  Ala Arg Gly Val Arg Ser Trp Gln Phe
                1020                          1025             1030

GGA GAG ACA GGA TTT GGG GGT TCT GCC ATA ATA GGA GGG GAA AAT CAC      3233
Gly Glu Thr Gly Phe Gly Gly Ser Ala Ile Ile Gly Gly Glu Asn His
                1035                          1040             1045

CCC CCA GCC ACC TCG GGG AAC TCC AGA CCA AGG GTG CCC AAC ATC TCC      3281
Pro Pro Ala Thr Ser Gly Asn Ser Arg Pro Arg Val Pro Asn Ile Ser
                1050                          1055             1060

CCT CAG GAC TGG GTG TGA CCA GAG GAA AAG GAA GTG CCC AAC ATC TCC      3329
Pro Gln Asp Trp Val  *  Pro Glu Glu Lys Glu Val Pro Asn Ile Ser
1065                           1070                         1075             1080

CAG CCT CCC CAG GTG TGA CTC CCT TGA TGG GTG CGT TCC CGC AGA          3377
Gln Pro Pro Gln Val Pro Ser Pro  *  Trp Val Arg Ser Arg Arg
                1085                          1090             1095

CCA AAG AGA GTG TGA CTC CCT TGC CAG CTC CAG AGT GGG GGT GTC          3425
Pro Lys Arg Val  *  Leu Pro Cys Gln Leu Gln Ser Gly Ala Val
1100                                  1105                    1110

CCA GGG GGC AAG AAG GGG TGT CAG GGC CCA GTG ACA AAA TCA TTG GGG      3473
Pro Gly Gly Lys Lys Gly Cys Gln Gly Pro Val Thr Lys Ser Leu Gly
                1115                          1120             1125

TTT GTA GTC CCA ACT TGC TGC TGT CAC CAC CAA ACT CAA TTT TTT          3521
Phe Val Val Pro Thr Cys Cys Cys His His Gln Thr Gln Ser Phe Phe
                1130                          1135             1140
```

FIG. 8I

```
TCC CTT GTA AAT GCC CCT CCC CCA GCT GCT GCC TTC ATA TTG AAG GTT    3569
Ser Leu Val Asn Ala Pro Pro Pro Ala Ala Phe Ile Leu Lys Val
1145                              1150                    1155                      1160

TTT GAG TTT TGT TTT TGG TCT TAA TTT TTC TCC CCG TTC CCT TTT TGT    3617
Phe Glu Phe Cys Phe Trp Ser  *  Phe Phe Ser Pro Phe Pro Phe Cys
            1165                              1170                          1175

TTC TTC GTT TTG TTT TTC TAC CGT CCT TGT CAT AAC TTT GTG TTG GAG    3665
Phe Phe Val Leu Phe Phe Tyr Arg Pro Cys His Asn Phe Val Leu Glu
      1180                          1185                              1190

GGA ACC TGT TTC ACT ATG GCC TCC TTT GCC CAA GTT GAA ACA GGG GCC    3713
Gly Thr Cys Phe Thr Met Ala Ser Phe Ala Gln Val Glu Thr Gly Ala
1195                              1200                          1205

CAT CAT GTC TGT TTC CAG AAC AGT GCC TTG GTC ATC CCA CAT CCC        3761
His His Val Cys Phe Gln Asn Ser Ala Leu Val Ile Pro His Pro
      1210                              1215                        1220

CGG ACC CCG CCT GGG ACC CCC AAG CTG TGT CCT ATG AAG GGG TGT GGG    3809
Arg Thr Pro Pro Gly Thr Pro Lys Leu Cys Pro Met Lys Gly Cys Gly
1225                              1230                          1235                      1240

GTG AGG TAG TGA AAA GGG CGG TAG TTG GTG GTG GAA CCC AGA AAC GGA    3857
Val Arg  *   *  Lys Gly Arg  *  Leu Val Val Glu Pro Arg Asn Gly
            1245                              1250                          1255

CGC CGG TGC TTG GAG GGG TTC TTA AAT TAT ATT TAA AAA AGT AAC TTT    3905
Arg Arg Cys Leu Glu Gly Phe Leu Asn Tyr Ile  *  Lys Ser Asn Phe
            1260                              1265                          1270

TTG TAT AAA TAA AAG AAA ATG GGA CGT GTC CCA GCT CCA GGG GTA        3950
Leu Tyr Lys  *  Lys Met Gly Arg Val Pro Ala Pro Gly Val
      1275                              1280                          1285

AAAAAAAAA AAAAAAAA                                                  3969
```

FIG. 9

Ala Arg Asn Ile Leu Val Asn Ser Asn Leu Val Cys Lys Val Ser Asp
1               5                   10                  15

Phe Gly Leu Ser Arg Phe Leu Glu Asp Asp Thr Ser Asp Pro Thr Tyr
                20                  25                  30

Thr Ser Ala Leu Gly Gly Lys Ile Pro Met Arg Trp Thr Ala Pro Glu
                35                  40                  45

Ala Ile Gln Tyr Arg Lys Phe Ala Ser Ala Ser
50                  55

FIG. 10

Asn Val Leu Val Lys Ser Pro Asn His Val Lys Ile Thr Asp Phe Gly
1               5                   10                  15

Leu Ala Arg Leu Leu Glu Gly Asp Glu Lys Glu Tyr Asn Ala Asp Gly
                20                  25                  30

Gly Lys Met Pro Ile Lys Trp Met Ala Leu Glu Cys Ile His Tyr Arg
                35                  40                  45

Lys Phe Thr His Gln Ser
50

FIG. 11

Asn Cys Met Leu Ala Gly Asp Met Thr Val Cys Val Ala Asp Phe Gly
1               5                   10                  15
Leu Ser Trp Lys Ile Tyr Ser Gly Ala Thr Ile Val Arg Gly Cys Ala
            20                  25                  30
Ser Lys Leu Pro Val Lys Trp Leu Ala Leu Gly Ser Leu Ala Asp Asn
            35                  40                  45
Leu Tyr Thr Val His Ser
            50

FIG. 12

Asn Cys Leu Val Gly Lys Asn Tyr Thr Ile Lys Ile Ala Asp Phe Gly
1               5                   10                  15
Met Ser Arg Asn Leu Tyr Ser Gly Asp Tyr Tyr
            20                  25

FIG. 13

Thr Arg Asn Ile Leu Val Glu Asn Arg Val Lys Ile Gly Asp
1                    5                    10                   15

Phe Gly Leu Thr Lys Val Leu Pro Gln Asp Lys Glu Tyr Tyr Lys Val
            20                   25                   30

Lys Glu Pro Gly Glu Ser Pro Ile Phe Trp Tyr Ala Pro Glu Ser Leu
            35                   40                   45

Thr Glu Ser Leu Phe Ser Val Ala Ser Asp
            50                   55

FIG. 14

Ala Arg Asn Ile Leu Val Asn Ser Asn Leu Val Cys Lys Val Ser Asp
1                    5                    10                   15

Phe Gly Met Ser Arg Val Leu Glu Asp Asp Pro Glu Ala Ala Tyr Thr
            20                   25                   30

Thr Arg Gly Gly Lys Ile Pro Ile Arg Trp Thr Ala Pro Glu Ala Ile
            35                   40                   45

Ala Tyr Arg Lys Phe Thr Ser Ala Ser Asp
            50                   55

FIG. 15A

```
  1 TCGGGTCGGA CCCACGCGCA GCGGCCGGAG ATGCAGCGGG GCGCCGCGCT GTGCCTGCGA
    AGCCCAGCCT GGGTGCGCGT CGCCGGCCTC TACGTCGCCC CGCGGCGCGA CACGGACGCT
  1                                 M  Q  R  G   A  A  L   C  L  R

61 CTGTGGCTCT GCCTGGGACT CCTGGACGGC CTGGTGAGTG GCTACTCCAT GACCCCCCCG
    GACACCGAGA CGGACCCTGA GGACCTGCCG GACCACTCAC CGATGAGGTA CTGGGGGGGC
 11 L  W  L   C  L  G  L   L  D  G   L  V  S  G   Y  S  M   T  P  P

121 ACCTTGAACA TCACGGAGGA GTCACGTC ATCGACACCG GTGACAGCCT GTCCATCTCC
    TGGAACTTGT AGTGCCTCCT CAGTGTGCAG TAGCTGTGGC CACTGTCGGA CAGGTAGAGG
 31 T  L  N  I   T  E  E   S  H  V   I  D  T  G   D  S  L   S  I  S

181 TGCAGGGGAC AGCACCCCCT CGAGTGGGCT TGGCCAGGAG CTCAGGAGGC GCCAGCCACC
    ACGTCCCCTG TCGTGGGGGA GCTCACCCGA ACCGGTCCTC GAGTCCTCCG CGGTCGGTGG
 51 C  R  G  Q   H  P  L   E  W  A   W  P  G  A   Q  E  A   P  A  T

241 GGAGACAAGG ACAGCGAGGA CACGGGGGTG GTGCGAGACT GCGAGGGCAC AGACGCCAGG
    CCTCTGTTCC TGTCGCTCCT GTGCCCCCAC CACGCTCTGA CGCTCCCGTG TCTGCGGTCC
 71 G  D  K  D   S  E  D   T  G  V   V  R  D  C   E  G  T   D  A  R

301 CCCTACTGCA AGGTGTTGCT GCTGCACGAG GTACATGCCA ACGACACAGG CAGCTACGTC
    GGGATGACGT TCCACAACGA CGACGTGCTC CATGTACGGT TGCTGTGTCC GTCGATGCAG
 91 P  Y  C  K   V  L  L   L  H  E   V  H  A  N   D  T  G   S  Y  V

361 TGCTACTACA AGTACATCAA GGCACGCATC GAGGGCACCA CGGCCGCCAG CTCCTACGTG
    ACGATGATGT TCATGTAGTT CCGTGCGTAG CTCCCGTGGT GCCGGCGGTC GAGGATGCAC
111 C  Y  Y  K   Y  I  K   A  R  I   E  G  T  T   A  A  S   S  Y  V

421 TTCGTGAGAG ACTTTGAGCA GCCATTCATC AACAAGCCTG ACACGCTCTT GGTCAACAGG
    AAGCACTCTC TGAAACTCGT CGGTAAGTAG TTGTTCGGAC TGTGCGAGAA CCAGTTGTCC
131 F  V  R  D   F  E  Q   P  F  I   N  K  P  D   T  L  L   V  N  R

481 AAGGACGCCA TGTGGGTGCC CTGTCTGGTG TCCATCCCCG GCCTCAATGT CACGCTGCGC
    TTCCTGCGGT ACACCCACGG GACAGACCAC AGGTAGGGGC CGGAGTTACA GTGCGACGCG
151 K  D  A  M   W  V  P   C  L  V   S  I  P  G   L  N  V   T  L  R

541 TCGCAAAGCT CGGTGCTGTG GCCAGACGGG CAGGAGGTGG TGTGGGATGA CCGGCGGGGC
    AGCGTTTCGA GCCACGACAC CGGTCTGCCC GTCCTCCACC ACACCCTACT GGCCGCCCCG
171 S  Q  S  S   V  L  W   P  D  G   Q  E  V  V   W  D  D   R  R  G

601 ATGCTCGTGT CCACGCCACT GCTGCACGAT GCCCTGTACC TGCAGTGCGA GACCACCTGG
    TACGAGCACA GGTGCGGTGA CGACGTGCTA CGGGACATGG ACGTCACGCT CTGGTGGACC
191 M  L  V  S   T  P  L   L  H  D   A  L  Y  L   Q  C  E   T  T  W

661 GGAGACCAGG ACTTCCTTTC CAACCCCTTC CTGGTGCACA TCACAGGCAA CGAGCTCTAT
    CCTCTGGTCC TGAAGGAAAG GTTGGGGAAG GACCACGTGT AGTGTCCGTT GCTCGAGATA
211 G  D  Q  D   F  L  S   N  P  F   L  V  H  I   T  G  N   E  L  Y
```

FIG. 15B

```
 721 GACATCCAGC TGTTGCCCAG GAAGTCGCTG GAGCTGCTGG TAGGGGAGAA GCTGGTCCTG
     CTGTAGGTCG ACAACGGGTC CTTCAGCGAC CTCGACGACC ATCCCCTCTT CGACCAGGAC
 231 D I Q L   L P R   K S L   E L L V   G E K   L V L

781 AACTGCACCG TGTGGGCTGA GTTTAACTCA GGTGTCACCT TTGACTGGGA CTACCCAGGG
     TTGACGTGGC ACACCCGACT CAAATTGAGT CCACAGTGGA AACTGACCCT GATGGGTCCC
 251 N C T V   W A E   F N S   G V T F   D W D   Y P G

841 AAGCAGGCAG AGCGGGGTAA GTGGGTGCCC GAGCGACGCT CCCAGCAGAC CCACACAGAA
     TTCGTCCGTC TCGCCCCATT CACCCACGGG CTCGCTGCGA GGGTCGTCTG GGTGTGTCTT
 271 K Q A E   R G K   W V P   E R R S   Q Q T   H T E

901 CTCTCCAGCA TCCTGACCAT CCACAACGTC AGCCAGCACG ACCTGGGCTC GTATGTGTGC
     GAGAGGTCGT AGGACTGGTA GGTGTTGCAG TCGGTCGTGC TGGACCCGAG CATACACACG
 291 L S S I   L T I   H N V   S Q H D   L G S   Y V C

961 AAGGCCAACA ACGGCATCCA GCGATTTCGG GAGAGCACCG AGGTCATTGT GCATGAAAAT
     TTCCGGTTGT TGCCGTAGGT CGCTAAAGCC CTCTCGTGGC TCCAGTAACA CGTACTTTTA
 311 K A N N   G I Q   R F R   E S T E   V I V   H E N

1021 CCCTTCATCA GCGTCGAGTG GCTCAAAGGA CCCATCCTGG AGGCCACGGC AGGAGACGAG
     GGGAAGTAGT CGCAGCTCAC CGAGTTTCCT GGGTAGGACC TCCGGTGCCG TCCTCTGCTC
 331 P F I S   V E W   L K G   P I L E   A T A   G D E

1081 CTGGTGAAGC TGCCCGTGAA GCTGGCAGCG TACCCCCCGC CCGAGTTCCA GTGGTACAAG
     GACCACTTCG ACGGGCACTT CGACCGTCGC ATGGGGGGCG GGCTCAAGGT CACCATGTTC
 351 L V K L   P V K   L A A   Y P P P   E F Q   W Y K

1141 GATGGAAAGG CACTGTCCGG GCGCCACAGT CCACATGCCC TGGTGCTCAA GGAGGTGACA
     CTACCTTTCC GTGACAGGCC CGCGGTGTCA GGTGTACGGG ACCACGAGTT CCTCCACTGT
 371 D G K A   L S G   R H S   P H A L   V L K   E V T

1201 GAGGCCAGCA CAGGCACCTA CACCCTCGCC CTGTGGAACT CCGCTGCTGG CCTGAGGCGC
     CTCCGGTCGT GTCCGTGGAT GTGGGAGCGG GACACCTTGA GGCGACGACC GGACTCCGCG
 391 E A S T   G T Y   T L A   L W N S   A A G   L R R

1261 AACATCAGCC TGGAGCTGGT GGTGAATGTG CCCCCCCAGA TACATGAGAA GGAGGCCTCC
     TTGTAGTCGG ACCTCGACCA CCACTTACAC GGGGGGGTCT ATGTACTCTT CCTCCGGAGG
 411 N I S L   E L V   V N V   P P Q I   H E K   E A S

1321 TCCCCCAGCA TCTACTCGCG TCACAGCCGC CAGGCCCTCA CCTGCACGGC CTACGGGGTG
     AGGGGGTCGT AGATGAGCGC AGTGTCGGCG GTCCGGGAGT GGACGTGCCG GATGCCCCAC
 431 S P S I   Y S R   H S R   Q A L T   C T A   Y G V

1381 CCCCTGCCTC TCAGCATCCA GTGGCACTGG CGGCCCTGGA CACCCTGCAA GATGTTTGCC
     GGGGACGGAG AGTCGTAGGT CACCGTGACC GCCGGGACCT GTGGGACGTT CTACAAACGG
 451 P L P L   S I Q   W H W   R P W T   P C K   M F A

1441 CAGCGTAGTC TCCGGCGGCG GCAGCAGCAA GACCTCATGC CACAGTGCCG TGACTGGAGG
     GTCGCATCAG AGGCCGCCGC CGTCGTCGTT CTGGAGTACG GTGTCACGGC ACTGACCTCC
 471 Q R S L   R R R   Q Q Q   D L M P   Q C R   D W R
```

FIG. 15C

```
1501 GCGGTGACCA CGCAGGATGC CGTGAACCCC ATCGAGAGCC TGGACACCTG GACCGAGTTT
     CGCCACTGGT GCGTCCTACG GCACTTGGGG TAGCTCTCGG ACCTGTGGAC CTGGCTCAAA
 491 A   V  T  T   Q  D  A   V  N  P   I  E  S   L  D  T   W  T  E  F

1561 GTGGAGGGAA AGAATAAGAC TGTGAGCAAG CTGGTGATCC AGAATGCCAA CGTGTCTGCC
     CACCTCCCTT TCTTATTCTG ACACTCGTTC GACCACTAGG TCTTACGGTT GCACAGACGG
 511 V   E  G  K   N  K  T   V  S  K   L  V  I   Q  N  A   N  V  S  A

1621 ATGTACAAGT GTGTGGTCTC CAACAAGGTG GGCCAGGATG AGCGGCTCAT CTACTTCTAT
     TACATGTTCA CACACCAGAG GTTGTTCCAC CCGGTCCTAC TCGCCGAGTA GATGAAGATA
 531 M   Y  K  C   V  V  S   N  K  V   G  Q  D   E  R  L   I  Y  F  Y

1681 GTGACCACCA TCCCCGACGG CTTCACCATC GAATCCAAGC CATCCGAGGA GCTACTAGAG
     CACTGGTGGT AGGGGCTGCC GAAGTGGTAG CTTAGGTTCG GTAGGCTCCT CGATGATCTC
 551 V   T  T  I   P  D  G   F  T  I   E  S  K   P  S  E   E  L  L  E

1741 GGCCAGCCGG TGCTCCTGAG CTGCCAAGCC GACAGCTACA AGTACGAGCA TCTGCGCTGG
     CCGGTCGGCC ACGAGGACTC GACGGTTCGG CTGTCGATGT TCATGCTCGT AGACGCGACC
 571 G   Q  P  V   L  L  S   C  Q  A   D  S  Y   K  Y  E   H  L  R  W

1801 TACCGCCTCA ACCTGTCCAC GCTGCACGAT GCGCACGGGA ACCCGCTTCT GCTCGACTGC
     ATGGCGGAGT TGGACAGGTG CGACGTGCTA CGCGTGCCCT TGGGCGAAGA CGAGCTGACG
 591 Y   R  L  N   L  S  T   L  H  D   A  H  G   N  P  L   L  L  D  C

1861 AAGAACGTGC ATCTGTTCGC CACCCCTCTG GCCGCCAGCC TGGAGGAGGT GGCACCTGGG
     TTCTTGCACG TAGACAAGCG GTGGGGAGAC CGGCGGTCGG ACCTCCTCCA CCGTGGACCC
 611 K   N  V  H   L  F  A   T  P  L   A  A  S   L  E  E   V  A  P  G

1921 GCGCGCCACG CCACGCTCAG CCTGAGTATC CCCCGCGTCG CGCCCGAGCA CGAGGGCCAC
     CGCGCGGTGC GGTGCGAGTC GGACTCATAG GGGGCGCAGC GCGGGCTCGT GCTCCCGGTG
 631 A   R  H  A   T  L  S   L  S  I   P  R  V   A  P  E   H  E  G  H

1981 TATGTGTGCG AAGTGCAAGA CCGGCGCAGC CATGACAAGC ACTGCCACAA GAAGTACCTG
     ATACACACGC TTCACGTTCT GGCCGCGTCG GTACTGTTCG TGACGGTGTT CTTCATGGAC
 651 Y   V  C  E   V  Q  D   R  R  S   H  D  K   H  C  H   K  K  Y  L

2041 TCGGTGCAGG CCCTGGAAGC CCCTCGGCTC ACGCAGAACT TGACCGACCT CCTGGTGAAC
     AGCCACGTCC GGGACCTTCG GGGAGCCGAG TGCGTCTTGA ACTGGCTGGA GGACCACTTG
 671 S   V  Q  A   L  E  A   P  R  L   T  Q  N   L  T  D   L  L  V  N

2101 GTGAGCGACT CGCTGGAGAT GCAGTGCTTG GTGGCCGGAG CGCACGCGCC CAGCATCGTG
     CACTCGCTGA GCGACCTCTA CGTCACGAAC CACCGGCCTC GCGTGCGCGG GTCGTAGCAC
 691 V   S  D  S   L  E  M   Q  C  L   V  A  G   A  H  A   P  S  I  V

2161 TGGTACAAAG ACGAGAGGCT GCTGGAGGAA AAGTCTGGAG TCGACTTGGC GGACTCCAAC
     ACCATGTTTC TGCTCTCCGA CGACCTCCTT TTCAGACCTC AGCTGAACCG CCTGAGGTTG
 711 W   Y  K  D   E  R  L   L  E  E   K  S  G   V  D  L   A  D  S  N

2221 CAGAAGCTGA GCATCCAGCG CGTGCGCGAG GAGGATGCGG GACGCTATCT GTGCAGCGTG
     GTCTTCGACT CGTAGGTCGC GCACGCGCTC CTCCTACGCC CTGCGATAGA CACGTCGCAC
 731 Q   K  L  S   I  Q  R   V  R  E   E  D  A   G  R  Y  L   C  S  V
```

FIG. 15D

```
2281 TGCAACGCCA AGGGCTGCGT CAACTCCTCC GCCAGCGTGG CCGTGGAAGG CTCCGAGGAT
     ACGTTGCGGT TCCCGACGCA GTTGAGGAGG CGGTCGCACC GGCACCTTCC GAGGCTCCTA
 751 C  N  A  K    G  C  V    N  S  S    A  S  V  A    V  E  G    S  E  D

2341 AAGGGCAGCA TGGAGATCGT GATCCTTGTC GGTACCGGCG TCATCGCTGT CTTCTTCTGG
     TTCCCGTCGT ACCTCTAGCA CTAGGAACAG CCATGGCCGC AGTAGCGACA GAAGAAGACC
 771 K  G  S  M    E  I  V    I  L  V    G  T  G  V    I  A  V    F  F  W

2401 GTCCTCCTCC TCCTCATCTT CTGTAACATG AGGAGGCCGG CCCACGCAGA CATCAAGACG
     CAGGAGGAGG AGGAGTAGAA GACATTGTAC TCCTCCGGCC GGGTGCGTCT GTAGTTCTGC
 791 V  L  L    L  I  F    C  N  M    R  R  P  A    H  A  D    I  K  T

2461 GGCTACCTGT CCATCATCAT GGACCCCGGG GAGGTGCCTC TGGAGGAGCA ATGCGAATAC
     CCGATGGACA GGTAGTAGTA CCTGGGGCCC CTCCACGGAG ACCTCCTCGT TACGCTTATG
 811 G  Y  L  S    I  I  M    D  P  G    E  V  P  L    E  E  Q    C  E  Y

2521 CTGTCCTACG ATGCCAGCCA GTGGGAATTC CCCCGAGAGC GGCTGCACCT GGGGAGAGTG
     GACAGGATGC TACGGTCGGT CACCCTTAAG GGGGCTCTCG CCGACGTGGA CCCCTCTCAC
 831 L  S  Y  D    A  S  Q    W  E  F    P  R  E  R    L  H  L    G  R  V

2581 CTCGGCTACG GCGCCTTCGG GAAGGTGGTG GAAGCCTCCG CTTTCGGCAT CCACAAGGGC
     GAGCCGATGC CGCGGAAGCC CTTCCACCAC CTTCGGAGGC GAAAGCCGTA GGTGTTCCCG
 851 L  G  Y  G    A  F  G    K  V  V    E  A  S  A    F  G  I    H  K  G

2641 AGCAGCTGTG ACACCGTGGC CGTGAAAATG CTGAAAGAGG GCGCCACGGC CAGCGAGCAC
     TCGTCGACAC TGTGGCACCG GCACTTTTAC GACTTTCTCC CGCGGTGCCG GTCGCTCGTG
 871 S  S  C  D    T  V  A    V  K  M    L  K  E  G    A  T  A    S  E  H

2701 CGCGCGCTGA TGTCGGAGCT CAAGATCCTC ATTCACATCG GCAACCACCT CAACGTGGTC
     GCGCGCGACT ACAGCCTCGA GTTCTAGGAG TAAGTGTAGC CGTTGGTGGA GTTGCACCAG
 891 R  A  L  M    S  E  L    K  I  L    I  H  I  G    N  H  L    N  V  V

2761 AACCTCCTCG GGGCGTGCAC CAAGCCGCAG GGCCCCCTCA TGGTGATCGT GGAGTTCTGC
     TTGGAGGAGC CCCGCACGTG GTTCGGCGTC CCGGGGGAGT ACCACTAGCA CCTCAAGACG
 911 N  L  L  G    A  C  T    K  P  Q    G  P  L  M    V  I  V    E  F  C

2821 AAGTACGGCA ACCTCTCCAA CTTCCTGCGC GCCAAGCGGG ACGCCTTCAG CCCCTGCGCG
     TTCATGCCGT TGGAGAGGTT GAAGGACGCG CGGTTCGCCC TGCGGAAGTC GGGGACGCGC
 931 K  Y  G  N    L  S  N    F  L  R    A  K  R  D    A  F  S    P  C  A

2881 GAGAAGTCTC CCGAGCAGCG CGGACGCTTC CGCGCCATGG TGGAGCTCGC CAGGCTGGAT
     CTCTTCAGAG GGCTCGTCGC GCCTGCGAAG GCGCGGTACC ACCTCGAGCG GTCCGACCTA
 951 E  K  S    P  E  Q  R    G  R  F    R  A  M  V    E  L  A    R  L  D

2941 CGGAGGCGGC CGGGGAGCAG CGACAGGGTC CTCTTCGCGC GGTTCTCGAA GACCGAGGGC
     GCCTCCGCCG GCCCCTCGTC GCTGTCCCAG GAGAAGCGCG CCAAGAGCTT CTGGCTCCCG
 971 R  R  R    P  G  S  S    D  R  V    L  F  A  R    F  S  K    T  E  G

3001 GGAGCGAGGC GGGCTTCTCC AGACCAAGAA GCTGAGGACC TGTGGCTGAG CCCGCTGACC
     CCTCGCTCCG CCCGAAGAGG TCTGGTTCTT CGACTCCTGG ACACCGACTC GGGCGACTGG
 991 G  A  R  R    A  S  P    D  Q  E    A  E  D  L    W  L  S    P  L  T
```

FIG. 15E

```
3061 ATGGAAGATC TTGTCTGCTA CAGCTTCCAG GTGGCCAGAG GGATGGAGTT CCTGGCTTCC
     TACCTTCTAG AACAGACGAT GTCGAAGGTC CACCGGTCTC CCTACCTCAA GGACCGAAGG
1011  M  E  D  L    V  C  Y     S  F  Q     V  A  R  G    M  E  F     L  A  S

3121 CGAAAGTGCA TCCACAGAGA CCTGGCTGCT CGGAACATTC TGCTGTCGGA AAGCGACGTG
     GCTTTCACGT AGGTGTCTCT GGACCGACGA GCCTTGTAAG ACGACAGCCT TTCGCTGCAC
1031  R  K  C     I  H  R  D    L  A  A     R  N  I  L    L  S     E  S  D  V

3181 GTGAAGATCT GTGACTTTGG CCTTGCCCGG GACATCTACA AAGACCCTGA CTACGTCCGC
     CACTTCTAGA CACTGAAACC GGAACGGGCC CTGTAGATGT TTCTGGGACT GATGCAGGCG
1051  V  K  I     C  D  F  G    L  A  R     D  I  Y     K  D  P  D    Y  V  R

3241 AAGGGCAGTG CCCGGCTGCC CCTGAAGTGG ATGGCCCCTG AAAGCATCTT CGACAAGGTG
     TTCCCGTCAC GGGCCGACGG GGACTTCACC TACCGGGGAC TTTCGTAGAA GCTGTTCCAC
1071  K  G  S     A  R  L     P  L  K  W    M  A  P  E    S  I  F     D  K  V

3301 TACACCACGC AGAGTGACGT GTGGTCCTTT GGGGTGCTTC TCTGGGAGAT CTTCTCTCTG
     ATGTGGTGCG TCTCACTGCA CACCAGGAAA CCCCACGAAG AGACCCTCTA GAAGAGAGAC
1091  Y  T  T     Q  S  D  V    W  S  F     G  V  L  L    W  E  I     F  S  L

3361 GGGGCCTCCC CGTACCCTGG GGTGCAGATC AATGAGGAGT TCTGCCAGCG GCTGAGAGAC
     CCCCGGAGGG GCATGGGACC CCACGTCTAG TTACTCCTCA AGACGGTCGC CGACTCTCTG
1111  G  A  S  P    Y  P  G     V  Q  I     N  E  E  F    C  Q  R     L  R  D

3421 GGCACAAGGA TGAGGGCCCC GGAGCTGGCC ACTCCCGCCA TACGCCGCAT CATGCTGAAC
     CCGTGTTCCT ACTCCCGGGG CCTCGACCGG TGAGGGCGGT ATGCGGCGTA GTACGACTTG
1131  G  T  R  M    R  A  P     E  L  A     T  P  A  I    R  R  I     M  L  N

3481 TGCTGGTCCG GAGACCCCAA GGCGAGACCT GCATTCTCGG AGCTGGTGGA GATCCTGGGG
     ACGACCAGGC CTCTGGGGTT CCGCTCTGGA CGTAAGAGCC TCGACCACCT CTAGGACCCC
1151  C  W  S     G  D  P  K    A  R  P     A  F  S  E    L  V  E     I  L  G

3541 GACCTGCTCC AGGGCAGGGG CCTGCAAGAG GAAGAGGAGG TCTGCATGGC CCCGCGCAGC
     CTGGACGAGG TCCCGTCCCC GGACGTTCTC CTTCTCCTCC AGACGTACCG GGGCGCGTCG
1171  D  L  L     Q  G  R  G    L  Q  E     E  E  E  V    C  M  A     P  R  S

3601 TCTCAGAGCT CAGAAGAGGG CAGCTTCTCG CAGGTGTCCA CCATGGCCCT ACACATCGCC
     AGAGTCTCGA GTCTTCTCCC GTCGAAGAGC GTCCACAGGT GGTACCGGGA TGTGTAGCGG
1191  S  Q  S  S    E  E  G     S  F  S     Q  V  S  T    M  A  L     H  I  A

3661 CAGGCTGACG CTGAGGACAG CCCGCCAAGC CTGCAGCGCC ACAGCCTGGC CGCCAGGTAT
     GTCCGACTGC GACTCCTGTC GGGCGGTTCG GACGTCGCGG TGTCGGACCG GCGGTCCATA
1211  Q  A  D     A  E  D  S    P  P  S     L  Q  R  H    S  L  A     A  R  Y

3721 TACAACTGGG TGTCCTTTCC CGGGTGCCTG GCCAGAGGGG CTGAGACCCG TGGTTCCTCC
     ATGTTGACCC ACAGGAAAGG GCCCACGGAC CGGTCTCCCC GACTCTGGGC ACCAAGGAGG
1231  Y  N  W     V  S  F  P    G  C  L     A  R  G  A    E  T  R     G  S  S

3781 AGGATGAAGA CATTTGAGGA ATTCCCCATG ACCCCAACGA CCTACAAAGG CTCTGTGGAC
     TCCTACTTCT GTAAACTCCT TAAGGGGTAC TGGGGTTGCT GGATGTTTCC GAGACACCTG
1251  R  M  K  T    F  E  E     F  P  M     T  P  T  T    Y  K  G     S  V  D
```

FIG. 15F

```
3841 AACCAGACAG ACAGTGGGAT GGTGCTGGCC TCGGAGGAGT TTGAGCAGAT AGAGAGCAGG
     TTGGTCTGTC TGTCACCCTA CCACGACCGG AGCCTCCTCA AACTCGTCTA TCTCTCGTCC
1271 N  Q  T  D     S  G  M     V  L  A     S  E  E  F     E  Q  I     E  S  R

3901 CATAGACAAG AAAGCGGCTT CAGGTAGCTG AAGCAGAGAG AGAGAAGGCA GCATACGTCA
     GTATCTGTTC TTTCGCCGAA GTCCATCGAC TTCGTCTCTC TCTCTTCCGT CGTATGCAGT
1291 H  R  Q  E     S  G  F     R  O

3961 GCATTTTCTT CTCTGCACTT ATAAGAAAGA TCAAAGACTT TAAGACTTTC GCTATTTCTT
     CGTAAAAGAA GAGACGTGAA TATTCTTTCT AGTTTCTGAA ATTCTGAAAG CGATAAAGAA

4021 CTGCTATCTA CTACAAACTT CAAAGAGGAA CCAGGAGGCC AAGAGGAGCA TGAAAGTGGA
     GACGATAGAT GATGTTTGAA GTTTCTCCTT GGTCCTCCGG TTCTCCTCGT ACTTTCACCT

4081 CAAGGAGTGT GACCACTGAA GCACCACAGG GAGGGGTTAG GCCTCCGGAT GACTGCGGGC
     GTTCCTCACA CTGGTGACTT CGTGGTGTCC CTCCCCAATC CGGAGGCCTA CTGACGCCCG

4141 AGGCCTGGAT AATATCCAGC CTCCCACAAG AAGCTGGTGG AGCAGAGTGT TCCCTGACTC
     TCCGGACCTA TTATAGGTCG GAGGGTGTTC TTCGACCACC TCGTCTCACA AGGGACTGAG

4201 CTCCAAGGAA AGGGAGACGC CCTTTCATGG TCTGCTGAGT AACAGGTGCC TTCCCAGACA
     GAGGTTCCTT TCCCTCTGCG GGAAAGTACC AGACGACTCA TTGTCCACGG AAGGGTCTGT

4261 CTGGCGTTAC TGCTTGACCA AAGAGCCCTC AAGCGGCCCT TATGCCAGCG TGACAGAGGG
     GACCGCAATG ACGAACTGGT TTCTCGGGAG TTCGCCGGGA ATACGGTCGC ACTGTCTCCC

4321 CTCACCTCTT GCCTTCTAGG TCACTTCTCA CAATGTCCCT TCAGCACCTG ACCCTGTGCC
     GAGTGGAGAA CGGAAGATCC AGTGAAGAGT GTTACAGGGA AGTCGTGGAC TGGGACACGG

4381 CGCCAGTTAT TCCTTGGTAA TATGAGTAAT ACATCAAAGA GTAGT
     GCGGTCAATA AGGAACCATT ATACTCATTA TGTAGTTTCT CATCA
```

FIG. 16A

```
  1 ATGGCTGGGA TTTTCTATTT CGCCCTATTT TCGTGTCTCT TCGGGATTTG
    TACCGACCCT AAAAGATAAA GCGGGATAAA AGCACAGAGA AGCCCTAAAC
  1 MetAlaGlyI lePheTyrPh eAlaLeuPhe SerCysLeuP heGlyIleCy
    CGACGCTGTC ACAGGTTCCA GGGTATACCC CGCGAATGAA GTTACCTTAT
    GCTGCGACAG TGTCCAAGGT CCCATATGGG GCGCTTACTT CAATGGAATA
    sAspAlaVal ThrGlySerA rgValTyrPr oAlaAsnGlu ValThrLeuLeu

101 TGGATTCCAG ATCTGTTCAG GGAGAACTTG GGTGGATAGC AAGCCCTCTG
    ACCTAAGGTC TAGACAAGTC CCTCTTGAAC CCACCTATCG TTCGGGAGAC
 35    AspSerAr gSerValGln GlyGluLeuG lyTrpIleAl aSerProLeu
    GAAGGAGGGT GGGAGGAAGT GAGTATCATG GATGAAAAAA ATACACCAAT
    CTTCCTCCCA CCCTCCTTCA CTCATAGTAC CTACTTTTTT TATGTGGTTA
    GluGlyGlyT rpGluGluVa lSerIleMet AspGluLysA snThrProIle

201 CCGAACCTAC CAAGTGTGCA ATGTGATGGA ACCCAGCCAG AATAACTGGC
    GGCTTGGATG GTTCACACGT TACACTACCT TGGGTCGGTC TTATTGACCG
 68   ArgThrTyr GlnValCysA snValMetGl uProSerGln AsnAsnTrpL
    TACGAACTGA TTGGATCACC CGAGAAGGGG CTCAGAGGGT GTATATTGAG
    ATGCTTGACT AACCTAGTGG GCTCTTCCCC GAGTCTCCCA CATATAACTC
    euArgThrAs pTrpIleThr ArgGluGlyA laGlnArgVa lTyrIleGlu

301 ATTAAATTCA CCTTGAGGGA CTGCAATAGT CTTCCGGGCG TCATGGGGAC
    TAATTTAAGT GGAACTCCCT GACGTTATCA GAAGGCCCGC AGTACCCCTG
101 IleLysPheT hrLeuArgAs pCysAsnSer LeuProGlyV alMetGlyTh
    TTGCAAGGAG ACGTTTAACC TGTACTACTA TGAATCAGAC AACGACAAAG
    AACGTTCCTC TGCAAATTGG ACATGATGAT ACTTAGTCTG TTGCTGTTTC
    rCysLysGlu ThrPheAsnL euTyrTyrTy rGluSerAsp AsnAspLysGlu
```

FIG. 16B

```
401 AGCGTTTCAT CAGAGAGAAC CAGTTTGTCA AAATTGACAC CATTGCTGCT
    TCGCAAAGTA GTCTCTCTTG GTCAAACAGT TTTAACTGTG GTAACGACGA
135    ArgPheIl eArgGluAsn GlnPheValL ysIleAspTh rIleAlaAla
    GATGAGAGCT TCACCCAAGT GGACATTGGT GACAGAATCA TGAAGCTGAA
    CTACTCTCGA AGTGGGTTCA CCTGTAACCA CTGTCTTAGT ACTTCGACTT
    AspGluSerP heThrGlnVa lAspIleGly AspArgIleM etLysLeuAsn
501 CACCGAGATC CGGGATGTAG GGCCATTAAG CAAAAAGGGG TTTTACCTGG
    GTGGCTCTAG GCCCTACATC CCGGTAATTC GTTTTTCCCC AAAATGGACC
168  ThrGluIle ArgAspValG lyProLeuSe rLysLysGly PheTyrLeuA
    CTTTTCAGGA TGTGGGGGCC TGCATCGCCC TGGTATCAGT CCGTGTGTTC
    GAAAAGTCCT ACACCCCCGG ACGTAGCGGG ACCATAGTCA GGCACACAAG
    laPheGlnAs pValGlyAla CysIleAlaL euValSerVa lArgValPhe
601 TATAAAAAGT GTCCACTCAC AGTCCGCAAT CTGGCCCAGT TTCCTGACAC
    ATATTTTTCA CAGGTGAGTG TCAGGCGTTA GACCGGGTCA AAGGACTGTG
201 TyrLysLysC ysProLeuTh rValArgAsn LeuAlaGlnP heProAspTh
    CATCACAGGG GCTGATACGT CTTCCCTGGT GGAAGTTCGA GGCTCCTGTG
    GTAGTGTCCC CGACTATGCA GAAGGGACCA CCTTCAAGCT CCGAGGACAC
    rIleThrGly AlaAspThrS erSerLeuVa lGluValArg GlySerCysVal
701 TCAACAACTC AGAAGAGAAA GATGTGCCAA AAATGTACTG TGGGGCAGAT
    AGTTGTTGAG TCTTCTCTTT CTACACGGTT TTTACATGAC ACCCCGTCTA
235    AsnAsnSe rGluGluLys AspValProL ysMetTyrCy sGlyAlaAsp
    GGTGAATGGC TGGTACCCAT TGGCAACTGC CTATGCAACG CTGGGCATGA
    CCACTTACCG ACCATGGGTA ACCGTTGACG GATACGTTGC GACCCGTACT
    GlyGluTrpL euValProIl eGlyAsnCys LeuCysAsnA laGlyHisGlu
801 GGAGCGGAGC GGAGAATGCC AAGCTTGCAA AATTGGATAT TACAAGGCTC
    CCTCGCCTCG CCTCTTACGG TTCGAACGTT TTAACCTATA ATGTTCCGAG
268  GluArgSer GlyGluCysG lnAlaCysLy sIleGlyTyr TyrLysAlaL
    TCTCCACGGA TGCCACCTGT GCCAAGTGCC CACCCCACAG CTACTCTGTC
    AGAGGTGCCT ACGGTGGACA CGGTTCACGG GTGGGGTGTC GATGAGACAG
    euSerThrAs pAlaThrCys AlaLysCysP roProHisSe rTyrSerVal
```

FIG. 16C

```
 901 TGGGAAGGAG CCACCTCGTG CACCTGTGAC CGAGGCTTTT TCAGAGCTGA
     ACCCTTCCTC GGTGGAGCAC GTGGACACTG GCTCCGAAAA AGTCTCGACT
 301 TrpGluGlyA laThrSerCy sThrCysAsp ArgGlyPheP heArgAlaAs
     CAACGATGCT GCCTCTATGC CCTGCACCCG TCCACCATCT GCTCCCCTGA
     GTTGCTACGA CGGAGATACG GGACGTGGGC AGGTGGTAGA CGAGGGGACT
     pAsnAspAla AlaSerMetP roCysThrAr gProProSer AlaProLeuAsn
1001 ACTTGATTTC AAATGTCAAC GAGACATCTG TGAACTTGGA ATGGAGTAGC
     TGAACTAAAG TTTACAGTTG CTCTGTAGAC ACTTGAACCT TACCTCATCG
 335    LeuIleSe rAsnValAsn GluThrSerV alAsnLeuGl uTrpSerSer
     CCTCAGAATA CAGGTGGCCG CCAGGACATT TCCTATAATG TGGTATGCAA
     GGAGTCTTAT GTCCACCGGC GGTCCTGTAA AGGATATTAC ACCATACGTT
     ProGlnAsnT hrGlyGlyAr gGlnAspIle SerTyrAsnV alValCysLys
1101 GAAATGTGGA GCTGGTGACC CCAGCAAGTG CCGACCCTGT GGAAGTGGGG
     CTTTACACCT CGACCACTGG GGTCGTTCAC GGCTGGGACA CCTTCACCCC
 368    LysCysGly AlaGlyAspP roSerLysCy sArgProCys GlySerGlyV
     TCCACTACAC CCCACAGCAG AATGGCTTGA AGACCACCAA AGGCTCCATC
     AGGTGATGTG GGGTGTCGTC TTACCGAACT TCTGGTGGTT TCCGAGGTAG
     alHisTyrTh rProGlnGln AsnGlyLeuL ysThrThrLy sGlySerIle
1201 ACTGACCTCC TAGCTCATAC CAATTACACC TTTGAAATCT GGGCTGTGAA
     TGACTGGAGG ATCGAGTATG GTTAATGTGG AAACTTTAGA CCCGACACTT
 401 ThrAspLeuL euAlaHisTh rAsnTyrThr PheGluIleT rpAlaValAs
     TGGAGTGTCC AAATATAACC CTAACCCAGA CCAATCAGTT TCTGTCACTG
     ACCTCACAGG TTTATATTGG GATTGGGTCT GGTTAGTCAA AGACAGTGAC
     nGlyValSer LysTyrAsnP roAsnProAs pGlnSerVal SerValThrVal
1301 TGACCACCAA CCAAGCAGCA CCATCATCCA TTGCTTTGGT CCAGGCTAAA
     ACTGGTGGTT GGTTCGTCGT GGTAGTAGGT AACGAAACCA GGTCCGATTT
 435     ThrThrAs nGlnAlaAla ProSerSerI leAlaLeuVa lGlnAlaLys
     GAAGTCACAA GATACAGTGT GGCACTGGCT TGGCTGGAAC CAGATCGGCC
     CTTCAGTGTT CTATGTCACA CCGTGACCGA ACCGACCTTG GTCTAGCCGG
     GluValThrA rgTyrSerVa lAlaLeuAla TrpLeuGluP roAspArgPro
```

FIG. 16D

```
1401 CAATGGGGTA ATCCTGGAAT ATGAAGTCAA GTATTATGAG AAGGATCAGA
     GTTACCCCAT TAGGACCTTA TACTTCAGTT CATAATACTC TTCCTAGTCT
 468  AsnGlyVal  IleLeuGluT  yrGluValLy  sTyrTyrGlu  LysAspGlnA
     ATGAGCGAAG CTATCGTATA GTTCGGACAG CTGCCAGGAA CACAGATATC
     TACTCGCTTC GATAGCATAT CAAGCCTGTC GACGGTCCTT GTGTCTATAG
     snGluArgSe rTyrArgIle ValArgThrA laAlaArgAs nThrAspIle
1501 AAAGGCCTGA ACCCTCTCAC TTCCTATGTT TTCCACGTGC GAGCCAGGAC
     TTTCCGGACT TGGGAGAGTG AAGGATACAA AAGGTGCACG CTCGGTCCTG
 501 LysGlyLeuA snProLeuTh rSerTyrVal PheHisValA rgAlaArgTh
     AGCAGCTGGC TATGGAGACT TCAGTGAGCC CTTGGAGGTT ACAACCAACA
     TCGTCGACCG ATACCTCTGA AGTCACTCGG GAACCTCCAA TGTTGGTTGT
     rAlaAlaGly TyrGlyAspP heSerGluPr oLeuGluVal ThrThrAsnThr
1601 CAGTGCCTTC CCGGATCATT GGAGATGGGG CTAACTCCAC AGTCCTTCTG
     GTCACGGAAG GGCCTAGTAA CCTCTACCCC GATTGAGGTG TCAGGAAGAC
 535   ValProSe  rArgIleIle GlyAspGlyA laAsnSerTh rValLeuLeu
     GTCTCTGTCT CGGGCAGTGT GGTGCTGGTG GTAATTCTCA TTGCAGCTTT
     CAGAGACAGA GCCCGTCACA CCACGACCAC CATTAAGAGT AACGTCGAAA
     ValSerValS erGlySerVa lValLeuVal ValIleLeuI leAlaAlaPhe
1701 TGTCATCAGC CGGAGACGGA GTAAATACAG TAAAGCCAAA CAAGAAGCGG
     ACAGTAGTCG GCCTCTGCCT CATTTATGTC ATTTCGGTTT GTTCTTCGCC
 568   ValIleSer ArgArgArgS erLysTyrSe rLysAlaLys GlnGluAlaA
     ATGAAGAGAA ACATTTGAAT CAAGGTGTAA GAACATATGT GGACCCCTTT
     TACTTCTCTT TGTAAACTTA GTTCCACATT CTTGTATACA CCTGGGGAAA
     spGluGluLy sHisLeuAsn GlnGlyValA rgThrTyrVa lAspProPhe
```

FIG. 16E

```
1801 ACGTACGAAG ATCCCAACCA AGCAGTGCGA GAGTTTGCCA AAGAAATTGA
     TGCATGCTTC TAGGGTTGGT TCGTCACGCT CTCAAACGGT TTCTTTAACT
 601 ThrTyrGluA spProAsnGl nAlaValArg GluPheAlaL ysGluIleAs
     CGCATCCTGC ATTAAGATTG AAAAAGTTAT AGGAGTTGGT GAATTTGGTG
     GCGTAGGACG TAATTCTAAC TTTTTCAATA TCCTCAACCA CTTAAACCAC
     pAlaSerCys IleLysIleG luLysValIl eGlyValGly GluPheGlyGlu
1901 AGGTATGCAG TGGGCGTCTC AAAGTGCCTG GCAAGAGAGA GATCTGTGTG
     TCCATACGTC ACCCGCAGAG TTTCACGGAC CGTTCTCTCT CTAGACACAC
 635    ValCysSe rGlyArgLeu LysValProG lyLysArgGl uIleCysVal
     GCTATCAAGA CTCTGAAAGC TGGTTATACA GACAAACAGA GGAGAGACTT
     CGATAGTTCT GAGACTTTCG ACCAATATGT CTGTTTGTCT CCTCTCTGAA
     AlaIleLysT hrLeuLysAl aGlyTyrThr AspLysGlnA rgArgAspPhe
2001 CCTGAGTGAG GCCAGCATCA TGGGACAGTT TGACCATCCG AACATCATTC
     GGACTCACTC CGGTCGTAGT ACCCTGTCAA ACTGGTAGGC TTGTAGTAAG
 668    LeuSerGlu AlaSerIleM etGlyGlnPh eAspHisPro AsnIleIleH
     ACTTGGAAGG CGTGGTCACT AAATGTAAAC CAGTAATGAT CATAACAGAG
     TGAACCTTCC GCACCAGTGA TTTACATTTG GTCATTACTA GTATTGTCTC
     isLeuGluGl yValValThr LysCysLysP roValMetIl eIleThrGlu
2101 TACATGGAGA ATGGCTCCTT GGATGCATTC CTCAGGAAAA ATGATGGCAG
     ATGTACCTCT TACCGAGGAA CCTACGTAAG GAGTCCTTTT TACTACCGTC
 701    TyrMetGluA snGlySerLe uAspAlaPhe LeuArgLysA snAspGlyAr
     ATTTACAGTC ATTCAGCTGG TGGGCATGCT TCGTGGCATT GGGTCTGGGA
     TAAATGTCAG TAAGTCGACC ACCCGTACGA AGCACCGTAA CCCAGACCCT
     gPheThrVal IleGlnLeuV alGlyMetLe uArgGlyIle GlySerGlyMet
2201 TGAAGTATTT ATCTGATATG AGCTATGTGC ATCGTGATCT GGCCGCACGG
     ACTTCATAAA TAGACTATAC TCGATACACG TAGCACTAGA CCGGCGTGCC
 735     LysTyrLe uSerAspMet SerTyrValH isArgAspLe uAlaAlaArg
     AACATCCTGG TGAACAGCAA CTTGGTCTGC AAAGTGTCTG ATTTTGGCAT
     TTGTAGGACC ACTTGTCGTT GAACCAGACG TTTCACAGAC TAAAACCGTA
     AsnIleLeuV alAsnSerAs nLeuValCys LysValSerA spPheGlyMet
```

FIG. 16F

```
2301 GTCCCGAGTG CTTGAGGATG ATCCGGAAGC AGCTTACACC ACCAGGGGTG
     CAGGGCTCAC GAACTCCTAC TAGGCCTTCG TCGAATGTGG TGGTCCCCAC
 768  SerArgVal LeuGluAspA spProGluAl aAlaTyrThr ThrArgGlyG
     GCAAGATTCC TATCCGGTGG ACTGCGCCAG AAGCAATTGC CTATCGTAAA
     CGTTCTAAGG ATAGGCCACC TGACGCGGTC TTCGTTAACG GATAGCATTT
     lyLysIlePr oIleArgTrp ThrAlaProG luAlaIleAl aTyrArgLys
2401 TTCACATCAG CAAGTGATGT ATGGAGCTAT GGAATCGTTA TGTGGGAAGT
     AAGTGTAGTC GTTCACTACA TACCTCGATA CCTTAGCAAT ACACCCTTCA
 801  PheThrSerA laSerAspVa lTrpSerTyr GlyIleValM etTrpGluVa
     GATGTCGTAC GGGGAGAGGC CCTATTGGGA TATGTCCAAT CAAGATGTGA
     CTACAGCATG CCCCTCTCCG GGATAACCCT ATACAGGTTA GTTCTACACT
     lMetSerTyr GlyGluArgP roTyrTrpAs pMetSerAsn GlnAspValIle
2501 TTAAAGCCAT TGAGGAAGGC TATCGGTTAC CCCCTCCAAT GGACTGCCCC
     AATTTCGGTA ACTCCTTCCG ATAGCCAATG GGGGAGGTTA CCTGACGGGG
 835    LysAlaIl eGluGluGly TyrArgLeuP roProProMe tAspCysPro
     ATTGCGCTCC ACCAGCTGAT GCTAGACTGC TGGCAGAAGG AGAGGAGCGA
     TAACGCGAGG TGGTCGACTA CGATCTGACG ACCGTCTTCC TCTCCTCGCT
     IleAlaLeuH isGlnLeuMe tLeuAspCys TrpGlnLysG luArgSerAsp
2601 CAGGCCTAAA TTTGGGCAGA TTGTCAACAT GTTGGACAAA CTCATCCGCA
     GTCCGGATTT AAACCCGTCT AACAGTTGTA CAACCTGTTT GAGTAGGCGT
 868  ArgProLys PheGlyGlnI leValAsnMe tLeuAspLys LeuIleArgA
     ACCCCAACAG CTTGAAGAGG ACAGGGACGG AGAGCTCCAG ACCTAACACT
     TGGGGTTGTC GAACTTCTCC TGTCCCTGCC TCTCGAGGTC TGGATTGTGA
     snProAsnSe rLeuLysArg ThrGlyThrG luSerSerAr gProAsnThr
```

FIG. 16G

```
2701 GCCTTGTTGG ATCCAAGCTC CCCTGAATTC TCTGCTGTGG TATCAGTGGG
     CGGAACAACC TAGGTTCGAG GGGACTTAAG AGACGACACC ATAGTCACCC
 901 AlaLeuLeuA spProSerSe rProGluPhe SerAlaValV alSerValGl
     CGATTGGCTC CAGGCCATTA AAATGGACCG GTATAAGGAT AACTTCACAG
     GCTAACCGAG GTCCGGTAAT TTTACCTGGC CATATTCCTA TTGAAGTGTC
     yAspTrpLeu GlnAlaIleL ysMetAspAr gTyrLysAsp AsnPheThrAla
2801 CTGCTGGTTA TACCACACTA GAGGCTGTGG TGCACGTGAA CCAGGAGGAC
     GACGACCAAT ATGGTGTGAT CTCCGACACC ACGTGCACTT GGTCCTCCTG
 935   AlaGlyTy rThrThrLeu GluAlaValV alHisValAs nGlnGluAsp
     CTGGCAAGAA TTGGTATCAC AGCCATCACA CACCAGAATA AGATTTTGAG
     GACCGTTCTT AACCATAGTG TCGGTAGTGT GTGGTCTTAT TCTAAAACTC
     LeuAlaArgI leGlyIleTh rAlaIleThr HisGlnAsnL ysIleLeuSer
2901 CAGTGTCCAG GCAATGCGAA CCCAAATGCA GCAGATGCAC GGCAGAATGG
     GTCACAGGTC CGTTACGCTT GGGTTTACGT CGTCTACGTG CCGTCTTACC
 968   SerValGln AlaMetArgT hrGlnMetGl nGlnMetHis GlyArgMetV
     TTCCCGTCTG AGCCAGTACT GAATAAACTC AAAACTCTTG AAATTAGTTT
     AAGGGCAGAC TCGGTCATGA CTTATTTGAG TTTTGAGAAC TTTAATCAAA
     alProValOp *AlaSerThr GluOc*ThrG lnAsnSerOp *AsnAm*Phe
3001 ACCTCATCCA TGCACTTTAA TTGAAGAACT GCACTTTTTT TACTTCGTCT
     TGGAGTAGGT ACGTGAAATT AACTTCTTGA CGTGAAAAAA ATGAAGCAGA
1001 ThrSerSerM etHisPheAs nOp*ArgThr AlaLeuPheL euLeuArgLe
     TCGCCCTCTG AAATTAAAGA AATGAAAAAA AAAAAACAAT ATCTGCAGCG
     AGCGGGAGAC TTTAATTTCT TTACTTTTTT TTTTTTGTTA TAGACGTCGC
     uArgProLeu LysLeuLysL ysOp*LysLy sLysAsnAsn IleCysSerVal
```

FIG. 16H

```
3101 TTGCTTGGTG CACAGATTGC TGAAACTGTG GGGCTTACAG AAATGACTGC
     AACGAACCAC GTGTCTAACG ACTTTGACAC CCCGAATGTC TTTACTGACG
1035    AlaTrpCy sThrAspCys Op*AsnCysG lvAlaTyrAr gAsnAspCys
     CGGTCATTTG AATGAGACCT GGAACAAATC GTTTCTAGA AGTACTTTTC
     GCCAGTAAAC TTACTCTGGA CCTTGTTTAG CAAAGAGTCT TCATGAAAAG
     ArgSerPheG luOp*AspLe uGluGlnIle ValSerGlnL ysTyrPheSer
3201 TGTTCATCAC CAGTCTGTAA AATACATGTA CCTATAGAAA TAGAACACTG
     ACAAGTAGTG GTCAGACATT TTATGTACAT GGATATCTTT ATCTTGTGAC
1068    ValHisHis GlnSerValL ysTyrMetTy rLeuAm*Lys Am*AsnThrA
     CCTCTGAGTT TTGATGCTGT ATTTGCTGCC AGACACTGAG CTTCTGAGAC
     GGAGACTCAA AACTACGACA TAAACGACGG TCTGTGACTC GAAGACTCTG
     laSerGluPh eOp*CysCys IleCysCysG lnThrLeuSe rPheOp*Asp
3301 ATCCCTGATT CTCTCTCCAT TTGGAATTAC AACGGTCGAC GAGCTCGA
     TAGGGACTAA GAGAGAGGTA AACCTTAATG TTGCCAGCTG CTCGAGCT
1101    IleProAspS erLeuSerIl eTrpAsnTyr AsnGlyArgA rgAlaArg
```

PROTEIN TYROSINE KINASE AGONIST ANTIBODIES

This application is a continuation-in-part of PCT/US93/00586, filed Jan. 22, 1993, which is a continuation-in-part of U.S. Ser. No. 07/826,935, filed Jan. 22, 1992 (now abandoned), the contents of which are expressly incorporated by reference herein.

BACKGROUND OF THE INVENTION

1. Field of the Invention

The present invention relates to novel protein tyrosine kinase (pTK) genes, the proteins encoded by these genes, RNA nucleic acid sequences which hybridize to the genes, antibodies specific for the encoded proteins, chimeras of the proteins and methods of use therefor.

In particular, this application relates to agonist antibodies which are able to activate the tyrosine kinase domain of the receptor pTKs disclosed herein and pTK-immunoglobulin chimeras.

2. Description of Related Art

Transduction of signals that regulate cell growth and differentiation is regulated in part by phosphorylation of various cellular proteins. Protein tyrosine kinases are enzymes that catalyze this process. Moreover, many act as growth factor receptors. The c-kit subgroup of receptor tyrosine kinases catalyze the phosphorylation of exogenous substrates, as well as tyrosine residues within their own polypeptide chains (Ullrich et al., Cell 61:203 [1990]). Members of the c-kit subgroup include FLT/FLK (Fetal Liver Kinase), FGF (Fibroblast Growth Factor Receptor) and NGF (Nerve Growth Factor Receptor).

The EPH tyrosine kinase subfamily, Eph, Elk, Eck, Eek, Hek, Hek2, Sek, Ehk-1, Ehk-2, Cek-4 to -10, Tyro 1, 4, 5 and 6, appears to be the largest subfamily of transmembrane tyrosine kinases (Hirai et al., Science 238:1717–1720 [1987]; Letwin et al., Oncogene 3:621–627 [1988]; Lhotak et al., Mol. Cell. Biol. 13:7071–7079 [1993]; Lindberg et al., Mol. Cell. Biol. 10:6316–6324 [1990]; Bohme et al., Oncogene 8:2857–2862 [1993]; Pasquale et al. Cell Regulation 2:523–534 [1991]; Sajjadi et al., New Biol. 3:769–778 [1991]; Wicks et al., Proc. Natl. Acad. Sci. USA. 89:1611–1615 [1992]; Lhotak et al., Mol. Cell. Bio. 11:2496–2502 [1991]; Gilardi-Hebenstreit et al., Oncogene 7:2499–2506 [1992]; Lai et al., Neuron 6:691–704 [1991]; Sajjadi et al., Oncogene 8:1807–1813 [1993]; and Maisonpierre et al., Oncogene 8:3277–3288 [1993]).

Additional pTKs and agohist antibodies thereto are needed in order to further study growth and differentiation of cells, for use as therapeutic agents and for diagnostic purposes. Accordingly, it is an object of the present invention to provide novel pTK genes, the proteins encoded thereby, antibodies specific for the encoded proteins, chimeras of the proteins and methods of use thereof.

SUMMARY OF THE INVENTION

The genes isolated as described herein are referred to, collectively, as "protein tyrosine kinase genes" or "pTK genes". The nucleic acid sequences of some of these genes, isolated as discussed herein, show significant homology with previously identified protein tyrosine kinases containing extracellular domains, which function as growth factor receptors (e.g., pTKs of the c-kit subgroup). Some of the pTK genes have been shown to be present in both megakaryocytic and lymphocytic cells.

In particular, fourteen pTK genes have been identified. Two pTK genes, referred to as SAL-S1 and SAL-D4 were identified in megakaryocytic cells. SAL-D4 is related to the CSK family of intracellular pTKs and SAL-S1 is related to the FGF receptor family of pTKs. Five pTK genes, referred to as LpTKs, were identified in lymphocytic cells and have been shown to be present in megakaryocytes as well. One pTK gene, referred to as HpTK5, was identified in human hepatoma cells. Six pTK genes, referred to as bpTK genes, were found in human brain tissue.

The pTK genes, which are the subject of the present invention, were generally identified using two sets of degenerative oligonucleotide primers: a first set which amplifies all pTK DNA segments (SEQ ID NOS: 1–2), and a second set which amplifies highly conserved sequences present in the catalytic domain of the c-kit subgroup of pTKs (SEQ ID NOS: 3–4). The pTK genes identified in this manner are described below.

SAL-S1 is expressed in several megakaryocytic cell lines, but not in erythroid cell lines. The nucleotide sequence of part of SAL-S1 was obtained, revealing a sequence containing 160 base pairs (SEQ ID NO: 5). This isolated DNA fragment encoded an amino acid sequence (SEQ ID NO: 6) which exhibited significant sequence homology with known protein tyrosine kinases of the FLT/FLK family. The deduced amino acid sequence of SAL-S1 (SEQ ID NO: 33) contains 1298 residues.

SAL-D4, also expressed in megakaryocytic cells, is a DNA fragment containing the nucleotide sequence of 147 base pairs. (SEQ ID NO: 7). This isolated DNA fragment encoded an amino acid sequence (SEQ ID NO: 8) which exhibited significant sequence homology with known protein tyrosine kinases of the CSK intracellular pTK family.

The LpTKs, including LpTK 2, LpTK 3, LpTK 4, LpTK 13 and LpTK 25, are expressed in lymphocytic cells, as well as megakaryocytic cells. The nucleotide sequence (151 base pairs) of the LpTK 3 gene was obtained (SEQ ID NO: 11). The nucleotide sequences of the LpTK 2, LpTK 4, and LpTK 13 genes contained 149 base pairs (SEQ ID NO: 9), 137 base pairs (SEQ ID NO: 13), and 211 base pairs (SEQ ID NO: 15) respectively. LpTK 25 has a nucleotide sequence of 3120 b.p. (SEQ ID NO: 22). A full length gene sequence has been obtained for LpTK 2 (SEQ ID NO: 19) which contains 7607 b.p. Additional sequencing of LpTK 4 revealed a sequence of 404 b.p. (SEQ ID NO: 21).

The HpTK5 gene, expressed in human hepatoma cells, has a nucleotide sequence of 3969 b.p. (SEQ ID NO: 23).

Nucleotide sequences of the bpTKs, including bpTK 1, bpTK 2, bpTK 3, bpTK 4, bpTK 5 and bpTK 7, are expressed in human brain tissue and encode proteins having the amino acid sequences of SEQ ID NOS: 25–29 and 34 respectively.

Thus, the present invention includes DNA isolated from a human megakaryocytic cell line, which hybridizes to DNA encoding an amino acid sequence which is highly conserved in the catalytic domain of protein tyrosine kinases of the c-kit subgroup.

The present invention also includes the proteins encoded by the pTK genes identified as described herein, which exhibit significant sequence homology with members of the c-kit subgroup of pTKs as well as the proteins encoded by HpTK5 and the bpTKs. The present invention also includes SAL-S1, SAL-D4, LpTK, HpTK5 and bpTK homologues or equivalents (i.e., proteins which have amino acid sequences substantially similar, but not identical, to that of SAL-S1, SAL-D4, the LpTKs, HpTK5 and the bpTKs, which exhibit tyrosine kinase activity). This invention further includes peptides (SAL-S1, SAL-D4, LpTK, HpTK5 and bpTK fragments) which retain tyrosine kinase activity, yet are less than the entire SAL-S1, SAL-D4, LpTK, HpTK5 and bpTK sequences; and uses for the SAL-S1, SAL-D4, the LpTK, HpTK and the bpTK nucleic acid sequences and SAL-S1, SAL-D4, LpTK, HpTK and bpTK equivalents.

The present invention further includes nucleic acid sequences which hybridize with DNA or RNA encoding the proteins described herein, which exhibit significant sequence homology with the FLT/FLK, FGF receptor or NGF receptor family of protein tyrosine kinases contained within the c-kit subgroup. Such nucleic acid sequences are useful as probes to identify pTK genes in other vertebrates, particularly mammals, and in other cell types. They can also be used as anti-sense oligonucleotides to inhibit protein tyrosine kinase activity, both in vitro and in vivo.

The SAL-S1, SAL-D4, LpTK, HpTK and bpTK tyrosine kinases of the present invention can be used as target proteins in conjunction with the development of drugs and therapeutics to modulate cell growth, differentiation and other metabolic functions. The SAL-S1, SAL-D4, LpTK, HpTK or bpTK proteins can be used as agonists or antagonists to other tyrosine kinases. The pTKs can also be instrumental in the modulation of megakaryocyte and/or platelet adhesion interactions.

In addition, the SAL-S1, SAL-D4, LpTK, HpTK and bpTK tyrosine kinases can be used in screening assays to detect cellular growth and/or differentiation factors. Using standard laboratory techniques, the ligands of the pTKs of the present invention can be identified. In particular, the invention provides chimeric pTK-immunoglobulin fusion proteins which are useful for isolating ligands to the pTKs disclosed herein. The chimeric proteins are also useful for diagnostic assays designed to detect these ligands present endogenously, within cells, as well as exogenously, in extracellular fluids. Assays, using the chimeric proteins, can also be designed as diagnostic aids to detect these ligands in body fluids such as blood and urine.

In another aspect, the invention provides antibodies specific for SAL-S1, SAL-D4, the LpTKs, HpTK5 and the bpTKs, which are optionally agonists for their respective pTK (where the pTK is a receptor). The invention also concerns a hybridoma cell line and an isolated nucleic acid encoding a monoclonal antibody as herein defined.

Also, the invention pertains to a method for activating a pTK as herein disclosed, comprising reacting the pTK with an agonist antibody thereto. In a different aspect, the invention concerns a method for enhancing cell growth and/or differentiation comprising administering to a human patient in need of such treatment a physiologically effective amount of an agonist antibody which activates a pTK as herein disclosed.

In a still further aspect, the invention concerns a method for detecting a pTK by contacting a source suspected of containing the pTK with a detectably labeled monoclonal antibody which reacts immunologically with the pTK, and determining whether the antibody binds to the source.

BRIEF DESCRIPTION OF THE DRAWINGS

FIGS. 1A and 1B depict the nucleotide sequence of SAL-S1 (SEQ ID NO: 5) and its deduced amino acid sequence (SEQ ID NO: 6).

FIGS. 2A and 2B depict the nucleotide sequence of SAL-D4 (SEQ ID NO: 7) and its deduced amino acid sequence (SEQ ID NO: 8).

FIG. 3A depicts the nucleotide sequence of LpTK 2 (SEQ ID NO: 9) and its deduced amino acid sequence (SEQ ID NO: 10).

FIG. 3B depicts the nucleotide sequence of LpTK 3 (SEQ ID NO: 11) and its deduced amino acid sequence (SEQ ID NO: 12).

FIG. 3C depicts the nucleotide sequence of LpTK 4 (SEQ ID NO: 13) and its deduced amino acid sequence (SEQ ID NO: 14).

FIG. 3D depicts the nucleotide sequence of LpTK 13 (SEQ ID NO: 15) and its deduced amino acid sequence (SEQ ID NO: 16).

FIGS. 4A–4I depict the nucleotide sequence (SEQ ID NO: 17) of SAL-S1 and its deduced amino acid sequence (SEQ ID NO: 18).

FIGS. 5A–5K depict the full length nucleotide sequence (SEQ ID NO: 19) of LpTK2 and its deduced amino acid sequence (SEQ ID NO: 20).

FIG. 6 depicts the partial nucleotide sequence (SEQ ID NO: 21) for LpTK4.

FIGS. 7A–7C depict the full length nucleotide sequence (SEQ ID NO: 23) for LpTK25.

FIGS. 8A–8I depict the full length nucleotide sequence (SEQ ID NO: 23) and the deduced amino acid sequence of HpTK5 (SEQ ID NO: 24).

FIG. 9 depicts the amino acid sequence (SEQ ID NO: 25) of bpTK1.

FIG. 10 depicts the amino acid sequence (SEQ ID NO: 26) of bpTK2.

FIG. 11 depicts the amino acid sequence (SEQ ID NO: 27) of bpTK3.

FIG. 12 depicts the amino acid sequence (SEQ ID NO: 28) of bpTK4.

FIG. 13 depicts the amino acid sequence (SEQ ID NO: 29) of bpTK5.

FIG. 14 depicts the amino acid sequence (SEQ ID NO: 30) of bpTK7.

FIGS. 15A–15F depict the full-length nucleotide sequence of SAL-S1 (SEQ ID NO: 31), its complement (SEQ ID NO: 32), and its deduced amino acid sequence (SEQ ID NO: 33).

FIGS. 16A–16H depict the full-length nucleotide sequence of bpTK7 (SEQ ID NO: 34), its complement (SEQ ID NO: 35), and its deduced amino acid sequence (SEQ ID NO: 36).

DETAILED DESCRIPTION OF THE PREFERRED EMBODIMENTS

Novel protein tyrosine kinase genes have been identified, their nucleic acid sequences determined, and the amino acid sequences of the encoded proteins deduced. The genes isolated as described herein are referred to, collectively, as "protein tyrosine kinase genes" or "pTK genes".

To facilitate the isolation and identification of these novel pTKs, two sets of DNA probes were used, as described in Example 1. The first set generally consisted of two degenerative oligonucleotide sequences, pTK 1 (SEQ ID NO: 1) and pTK 2 (SEQ ID NO: 2) (Matthews, Cell 65:1143 [1991]; and Wilks, Proc. Natl. Acad. Sci. USA 86:1603 [1989]). These sequences were used as primers in a polymerase chain reaction to amplify tyrosine kinase DNA segments (Mullis, et al., Cold Spring Harbor Symp. Advan. Biol. 51:263 [1986]).

The second set generally consisted of two oligonucleotide sequences, pTK 3 (SEQ ID NO: 3) and pTKKW (SEQ ID NO: 4) designed to amplify the nucleic acid sequence which encodes the highly conserved regions of the catalytic domains of the c-kit family of protein tyrosine kinases. These sequences were used as primers in the polymerase chain reaction (PCR) in a second round of DNA amplification. Using this two-step amplification procedure, DNA fragments which hybridized to these pTK primers were identified, isolated and subsequently sequenced.

In particular, fourteen pTK genes have been identified. Two pTK genes, referred to as SAL-S1 and SAL-D4, were identified in several megakaryocytic cell lines, including CMK 11–5, DAMI, UT-7 and UT-7 grown in erythropoietin, but not in the erythroid cell lines HEL, PMA stimulated HEL cells, or K562. Five pTK genes, referred to as LpTKs, were identified in lymphocytic, as well as in megakaryocytic cells. One pTK gene, referred to as HpTK5, was identified in human hepatoma cells, and six genes, referred to as bpTKs, were identified in human brain tissue.

SAL-S1 (SEQ ID NOS: 6, 18 and 33) encoded by the nucleic acid sequence of SEQ ID NOS: 5, 17 and 31 exhibits significant homology with the FLT/FLK family of pTKs. SAL-S1 has a signal peptide (i.e., amino acid residues 1 to 24 of FIG. 15); extracellular domain (i.e., amino acid residues 25 to 775 of FIG. 15); transmembrane domain (i.e., amino acid residues 776 to 800 of FIG. 15) and a cytoplasmic tyrosine kinase domain (i.e., amino acid residues 801 to 1298 of FIG. 15). SAL-D4 (SEQ ID NO: 8) encoded by SEQ ID NO: 7 is related to the CSK family of intracellular pTKs. The LpTKs, LpTK 2 (SEQ ID NOS: 10 and 20) encoded by SEQ ID NOS: 9 and 19; LpTK 3 (SEQ ID NO: 12) encoded by SEQ ID NO: 11; LpTK4 (SEQ ID NO: 14) encoded by SEQ ID NOS: 13 and 21; LpTK13 (SEQ ID NO: 16) encoded by SEQ ID NO: 15; and LpTK25 encoded by SEQ ID NO: 22, also exhibit sequence homology with known protein tyrosine kinases.

HpTK5 (SEQ ID NO: 24) encoded by SEQ ID NO: 23 and the bpTKs 1, 2, 3, 4, 5 and 7 (SEQ ID NOS: 25–29 and 36 respectively), similarly exhibit sequence homology with known protein tyrosine kinases. BpTK7 encodes a receptor pTK with a signal peptide (i.e., amino acid residues 1–19 of FIG. 16); extracellular domain (i.e., amino acid residues 20–547 of FIG. 16); and transmembrane domain (i.e., amino acid residues 548–570 of FIG. 16). The remaining sequence comprises the intracellular tyrosine kinase domain.

Thus, as described above, DNA molecules which hybridize with DNA encoding amino acid sequences present in the catalytic domain of a protein tyrosine kinase of the c-kit subgroup of protein kinases have been isolated and sequenced. These isolated DNA sequences, collectively referred to as "pTK genes", (and their deduced amino acid sequences) have been shown to exhibit significant sequence homology with known members of pTK families.

Once isolated, these DNA fragments can be amplified using known standard techniques such as PCR. These amplified fragments can then be cloned into appropriate cloning vectors and their DNA sequences determined.

These DNA sequences can be excised from the cloning vectors, labeled with a radiolabeled nucleotide such as $^{32}P$ and used to screen appropriate cDNA libraries to obtain the full-length cDNA clone.

The pTK genes as described above have been isolated from the source in which they occur naturally, e.g., megakaryocytic and lymphocytic cells. The present invention is intended to include pTK genes produced using genetic engineering techniques, such as recombinant technology, as well as pTK genes that are synthesized chemically.

The deduced amino acid sequences of the pTK genes include amino acid sequences which encode peptides exhibiting significant homology with the catalytic domain of protein tyrosine kinases of the c-kit subgroup of tyrosine kinases. These proteins, encoded by the pTK genes, can include sequences in which functionally equivalent amino acid residues are substituted for residues within the sequence, resulting in a silent change, that is a change not detected phenotypically. For example, one or more amino acid residues within the sequence can be substituted by another amino acid of a similar polarity which acts as a functional equivalent, resulting in a silent substitution.

In addition, the protein structure can be modified by deletions, additions, inversion, insertions or substitutions of one or more amino acid residues in the sequence which do not substantially detract from the desired functional tyrosine kinase properties of the peptide.

Modified pTKs of the present invention, with tyrosine kinase activity, can be made using recombinant DNA techniques, such as excising it from a vector containing a cDNA encoding such a protein, or by synthesizing DNA encoding the desired protein mechanically and/or chemically using known techniques.

An alternate approach to producing the pTKs of the present invention is to use peptide synthesis to make a peptide or polypeptide having the amino acid sequence of such a protein, depending on the length of the pTK desired. The peptides or modified equivalents thereof, can be synthesized directly by standard solid or liquid phase chemistries for peptide synthesis.

Preferably, the pTKs of the present invention will be produced by inserting DNA encoding the proteins into an appropriate vector/host system where it will be expressed. The DNA sequences can be obtained from sources in which they occur naturally, can be chemically synthesized or can be produced using standard recombinant technology.

This invention also pertains to an expression vector comprising a pTK gene of the present invention, encoding for a protein which exhibits receptor tyrosine kinase activity.

The pTK genes of the present invention can be used for a number of diagnostic and therapeutic purposes. For example, the nucleic acid sequences of the pTK genes can be used as probes to identify other protein tyrosine kinases present in other cell types, including eukaryotic and prokaryotic cell types.

The nucleic acid sequences can also be used to design drugs that directly inhibit the kinase activity of protein tyrosine kinases, or to design peptides that bind to the catalytic domain of tyrosine kinases, thus inhibiting their activity. These sequences can also be used to design anti-sense nucleotides that can also inhibit, or destroy, tyrosine kinase activity. Such inhibition of tyrosine kinase activity would be desirable in pathological states where decreased cellular proliferation would be beneficial, such as leukemias or other malignancies.

The nucleic acid sequences can also be used to design drugs, peptides or anti-sense nucleotides as above, but with enhancing, rather than inhibitory effects, on tyrosine kinases. Such enhanced tyrosine kinase activity would result in increasing the phosphorylation of substrates (exogenous, as well as endogenous tyrosine residues). Enhanced effects would be desirable in states where increased cellular proliferation would be beneficial, such as anemias, bleeding disorders and during surgical procedures.

The pTK genes of the present invention can also be used to obtain soluble fragments of receptor tyrosine kinases, capable of binding their respective ligands. pTK genes encoding soluble tyrosine kinase fragments can be produced using recombinant DNA techniques or synthetically. In either case, the DNA obtained encodes a soluble pTK fragment which lacks a substantial portion of the hydrophobic transmembrane region to permit solubilization of the fragment.

These soluble pTK protein fragments can be introduced exogenously to act as competitors with the endogenous, membrane bound pTK for their respective ligands, thus inhibiting tyrosine kinase activity. Alternately, a modified soluble pTK protein fragment can be introduced which binds the ligand but does not activate kinase activity.

These soluble pTK protein fragments can also be used in binding assays to detect ligands such as growth and differentiation factors. Once these ligands are identified, they may be altered or modified to inhibit or enhance kinase activity. For example, the ligands may be modified or attached to substances that are toxic to the cell, such a ricin, thus destroying the target cell. The substance may be a superactivating substance which, after binding to the pTK, may substantially increase the kinase activity, or activate other growth factors.

pTK genes of the present invention would also be useful to develop diagnostic tools for in vitro screening assays for ligands such as growth factors or differentiation factors that inhibit or enhance kinase activity. The proteins encoded by the pTK genes can also be used in such assays, or as immunogens to produce monoclonal or polyclonal antibodies to be used in such assays.

In one embodiment of the invention, a chimera comprising a fusion of the extracellular domain of the pTK (where the pTK is a receptor) and an immunoglobulin constant domain can be constructed which can be used to assay for ligands for the receptor and can be used for the production of antibodies against the extracellular domain of the receptor.

The expression "extracellular domain" or "ECD" when used herein refers to any polypeptide sequence that shares a ligand binding function of the extracellular domain of the naturally occurring receptor pTKs disclosed herein. Ligand binding function of the extracellular domain refers to the ability of the polypeptide to bind at least one pTK ligand. Accordingly, it is not necessary to include the entire extracellular domain since smaller segments are commonly found to be adequate for ligand binding. The truncated extracellular domain is generally soluble. The term ECD encompasses polypeptide sequences in which the hydrophobic transmembrane sequence (and, optionally, 1–20 amino acids C-terminal and/or N-terminal to the transmembrane domain) of the mature pTK has been deleted. Thus, the soluble extracellular domain-containing polypeptide can comprise the extracellular domain and the cytoplasmic domain of the pTK. Alternatively, in the preferred embodiment, the polypeptide comprises only the extracellular domain of the pTK. The extracellular and transmembrane domains of the pTK can be readily determined by the skilled practitioner by aligning the pTK of interest with known pTK amino acid sequences for which these domains have been delineated. Alternatively, the hydrophobic transmembrane domain can be readily delineated based on a hydrophobicity plot of the sequence. The extracellular domain is N-terminal to the transmembrane domain.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., *Nature* 298:286 [1982]; EP 120, 694; EP 125,023; Morrison, *J. Immun.* 123:793 [1979]; K öhler et al., *Proc. Nat'l. Acad. Sci. USA* 77:2197 [1980]; Raso et al., *Cancer Res.* 41:2073 [1981]; Morrison et al., *Ann. Rev. Immunol.* 2:239 [1984]; Morrison, *Science* 229:1202 [1985]; Morrison et al., *Proc. Nat'l. Acad. Sci. USA* 81:6851 [1984]; EP 255,694; EP 266,663; and WO 88/03559. Reassorted immunoglobulin chains also are known. See for example U.S. Pat. No. 4,444,878; WO 88/03565; and EP 68,763 and references cited therein. The immunoglobulin moiety in the chimera of the present invention may be obtained from $IgG_1$, $IgG_2$, $IgG_3$, or $IgG_4$ subtypes, IgA, IgE, IgD or IgM, but preferably $IgG_1$ or $IgG_3$. Most preferably, the immunoglobulin moiety is the Fc portion of IgGγ.

The terms "chimera comprising a fusion of an extracellular domain of a pTK with an immunoglobulin constant domain sequence" or "pTK-immunoglobulin chimera" refer to a polypeptide comprising an extracellular domain coding amino acid sequence of a pTK conjugated to an immunoglobulin constant domain sequence. This definition includes chimeras in monomeric, homo- or heteromultimeric, and particularly homo- or heterodimeric, or -tetrameric forms.

A preferred embodiment is the fusion of the C-terminus of the extracellular domain of a pTK, to the N-terminus of the C-terminal portion of an antibody (in particular the Fc domain), containing the effector functions of immunoglobulin $G_1$. In a preferred embodiment, the entire heavy chain constant region is fused to the extracellular domain. In another preferred embodiment, a sequence beginning in the hinge region just upstream of the papain cleavage site (which defines IgG Fc chemically; residue 216, taking the first residue of heavy chain constant region to be 114 (Kabat et al., *Sequences of Immunological Interest*, National Institutes of Health, Bethesda, Md., [1987]), or analogous sites of other immunoglobulins) is fused to the ECD of the pTK.

In a particularly preferred embodiment, the pTK extracellular domain is fused to the hinge region and $C_H2$ and $C_H3$ or $C_H1$, hinge, $C_H2$ and $C_H3$ domains of an $IgG_1$, $IgG_2$ or $IgG_3$ heavy chain. The precise site at which the fusion is made is not critical, and the optimal site can be determined by routine experimentation. A principal advantage of the chimeras is that they are secreted into the culture medium of recombinant hosts, although the degree of secretion might be different for various expression systems.

In general, the chimeras of the present invention are constructed in a fashion similar to chimeric antibodies in which a variable domain from an antibody of one species is substituted for the variable domain of another species. See, for example, EP 0 125 023; EP 173,494; Munro, *Nature* 312: [13 Dec. 1984]; Neuberger et al., *Nature* 312: [13 Dec. 1984]; Sharon et al., *Nature* 309: [24 May 1984]; Morrison et al., *Proc. Nat'l Acad. Sci. USA* 81:6851–6855 [1984]; Morrison et al. *Science* 229:1202–1207 [1985]; Boulianne et al., *Nature* 312:643–646 [13 Dec. 1984]; Capon et al., *Nature* 337, 525–531 [1989]; Traunecker et al., *Nature* 339, 68–70 [1989].

To prepare the pTK-Ig chimeric polypeptides, the DNA including a region encoding the desired pTK sequence is cleaved by a restriction enzyme at or proximal to the 3' end of the DNA encoding the immunoglobulin-like domain(s)

and at a point at or near the DNA encoding the N-terminal end of the mature pTK (where use of a different leader is contemplated) or at or proximal to the N-terminal coding region for the pTK (where the native signal is employed). This DNA fragment then is readily inserted proximal to DNA encoding an immunoglobulin light or heavy chain constant region and, if necessary, the resulting construct tailored by deletional mutagenesis. Preferably, the Ig is a human immunoglobulin when the variant is intended for in vivo therapy for humans. DNA encoding immunoglobulin light or heavy chain constant regions is known or readily available from cDNA libraries or is synthesized. See for example, Adams et al., *Biochemistry* 19:2711–2719 [1980]; Gough et al., *Biochemistry* 19:2702–2710 [1980]; Dolby et al., *P.N.A.S. USA*, 77:6027–6031 [1980]; Rice et al., *P.N.A.S. USA* 79:7862–7865 [1982]; Falkner et al., *Nature* 298:286–288 [1982]; and Morrison et al., *Ann. Rev. Immunol.* 2:239–256 [1984].

The chimeric proteins disclosed herein are useful as diagnostics for isolating or screening ligands for the pTK of interest using the techniques of Lyman et al., *Cell* 75:1157–1167 [1993], for example. Also, the chimeric proteins are useful for diagnostic purposes for studying the interaction of various ligands with the extracellular domain of the various pTKs (see, e.g., Bennett et al., *J. Biol. Chem.* 266(34):23060–23067 [1991]). The chimeric proteins are further useful for the production of antibodies against the extracellular domain of the pTK (see Examples 3 and 5 herein). The chimeric proteins also have an additional therapeutic utility insofar as they provide a soluble form of the extracellular domain of the pTK which generally has an enhanced plasma half life (compared to the extracellular domain only) and therefore can be formulated in a pharmaceutically acceptable carrier and administered to a patient. The chimeric proteins are believed to find use as therapeutic agents for removal of excess systemic or tissue-localized pTK ligand which has been administered to a patient. Removal of excess ligand is particularly desirably where the ligand may be toxic to the patient. The chimeric protein acts to bind the ligand in competition with the endogenous pTK in the patient. Similarly, it is contemplated that the chimeric protein can be administered to a patient simultaneously, or subsequent to, administration of the ligand in the form of a sustained release composition. The chimeric protein acts as a soluble binding protein for the ligand, thereby extending the half-life of the ligand.

The term "antibody" is used herein in the broadest sense and specifically covers polyclonal antibodies, monoclonal antibodies, immunoglobulin chains or fragments thereof, which react immunologically with a pTK.

In the preferred embodiment of the invention, the antibodies are monoclonal antibodies produced using techniques which are well known in the art. For example, the hybridoma technique described originally by Kohler and Milsrein, *Eur. J. Immunol.*, 6:511 [1976], and also described by Hammerling et al., In: *Monoclonal Antibodies and T-Cell Hybridomas*, Elsevier, N.Y., pp. 563–681 [1981] can be used. The techniques of Cote et al. and Boerner al. are also available for the preparation of human monoclonal antibodies [Cote et al., *Monoclonal Antibodies and Cancer Therapy*, Alan R. Liss, p. 77 [1985]and Boerner et al., *J. Immunol.*, 147(1):86–95 [1991]).

The term "monoclonal antibody" as used herein refers to an antibody (as hereinabove defined) obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they can be synthesized by a hybridoma culture, uncontaminated by other immunoglobulins.

"Humanized" forms of non-human (e.g., murine) antibodies are immunoglobulins, immunoglobulin chains or fragments thereof (such as Fv, Fab, Fab', F(ab')$_2$ or other antigen-binding subsequences of antibodies) which contain minimal amino acid residues derived from a non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, a humanized antibody may comprise residues which are found neither in the recipient antibody nor in the imported CDR or framework sequences. These modifications are made to further refine and optimize antibody performance.

The monoclonal antibodies herein include hybrid (chimeric) and recombinant antibodies produced by splicing a variable (including hypervariable) domain of an anti-pTK antibody with a constant domain (e.g., "humanized" antibodies), only one of which is directed against a pTK, or a light chain with a heavy chain, or a chain from one species with a chain from another species, or fusions with heterologous proteins, regardless of species of origin or immunoglobulin class or subclass designation, so long as they are able to bind to the pTK of interest [See, e.g., Cabilly, et al., U.S. Pat. No. 4,816,567; and Mage & Lamoyi, in *Monoclonal Antibody Production Techniques and Applications*, pp.79–97 (Marcel Dekker, Inc., New York [1987]).

For "chimetic" and "humanized" antibodies see, for example, U.S. Pat. No. 4,816,567; WO 91/09968; EP 452, 508; and WO 91/16927.

Thus, the modifier "monoclonal" indicates the character of the antibody as being obtained from a substantially homogeneous population of antibodies, and is not to be construed as requiring production of the antibody by any particular method.

In the most preferred embodiment of the invention, the antibodies are agohist antibodies. By "agonist antibody" is meant an antibody which is able to bind to, and activate, a particular pTK. For example, the agohist may bind to the extracellular domain of the pTK and thereby cause dimerization of the pTK, resulting in transphosphorylation and activation of the intracellular catalytic kinase domain. Consequently, this may result in stimulation of growth and/or differentiation of cells expressing the receptor in vitro and/or in vivo. The agohist antibodies herein are preferably against epitopes within the extracellular domain of the pTK, and preferably have the same biological characteristics as the monoclonal antibody produced by the hybridoma cell line deposited under American Type Culture Collection Accession No. ATCC HB 11,583. By "biological characteristics" is meant the in vitro and/or in vivo activities of the monoclonal antibody, e.g., ability to activate the kinase domain of a particular pTK, ability to stimulate cell growth and/or differentiation of cells expressing the pTK, and binding characteristics of the antibody, etc. Accordingly, the antibody preferably binds to substantially the same epitope as the anti-HpTK5 monoclonal antibody specifically disclosed herein. Most preferably, the antibody will also have substantially the same or greater antigen binding affinity of the anti-HpTK5 monoclonal antibody disclosed herein. To determine whether a monoclonal antibody has the same specificity as the anti-HpTK5 antibody specifically disclosed (i.e., the antibody having the ATCC deposit No. HB 11,583), one can, for example, use a competitive ELISA binding assay.

DNA encoding the monoclonal antibodies useful in the method of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells.

The agonist antibodies disclosed herein are useful for in vitro diagnostic assays for activating the pTK receptor of interest. This is useful in order to study the role of the receptor in cell growth and/or differentiation.

The pTK agonist antibodies have a further therapeutic utility in a method for enhancing cell growth and/or differentiation comprising administering to a human patient in need of such treatment a physiologically effective amount of an exogenous pTK agonist antibody. Agonist antibodies to the SAL-S1 pTK may find utility in treating bleeding disorders and anemias, since this pTK was found to be expressed in megakaryocytic cells. The bpTK agonist antibodies may similarly be used to enhance differentiation and/or proliferation of brain cells in neurodegenerative diseases (such as Alzheimers disease) based on the expression of these receptors in brain tissue. Finally, HpTK5 agonist antibodies may be used to enhance proliferation of primitive hematopoietic cells in patients having undergone chemo- or radiation therapy or bone marrow transplantation.

An "exogenous" therapeutic compound is defined herein to mean a therapeutic compound that is foreign to the mammalian patient, or homologous to a compound found in the mammalian patient but produced outside the mammalian patient.

The antibodies of the present invention are also suitable for detecting a pTK by contacting a source suspected to contain the pTK with a detectably labeled monoclonal antibody, and determining whether the antibody binds to the source. There are many different labels and methods of labeling known in the art. Suitable labels include, for example, enzymes, radioisotopes, fluorescent compounds, chemi- and bioluminescent compounds, paramagnetic isotopes. The pTK may be present in biological samples, such as biological fluids or tissues. For analytical or diagnostic purposes, the antibodies of the present invention are administered in an amount sufficient to enable the detection of a site on a pTK for which the monoclonal antibody is specific. The concentration of the detectably labeled monoclonal antibody should be sufficient to give a detectable signal above background, when bound to a pTK epitope.

The pTK agonist antibodies disclosed herein may be administered to a mammal, preferably a human, in a pharmaceutically acceptable dosage form, including those that may be administered to a human intravenously as a bolus or by continuous infusion over a period of time, by intramuscular, subcutaneous, intra-articular, intrasynovial, intrathecal, oral, topical, or inhalation routes.

Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of antibody include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms are suitably used. Such forms include, for example, microcapsules, nano-capsules, liposomes, plasters, inhalation forms, nose sprays, and sublingual tablets. The antibody will typically be formulated in such vehicles at a concentration of about 0.1 mg/ml to 100 mg/ml.

Pharmaceutical compositions may be prepared and formulated in dosage forms by methods known in the art; for example, see Remington's Pharmaceutical Sciences, Mack Publishing Company, Easton, Penn., 15th Edition 1975.

An effective amount of the pTK agonist antibody to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 1000 mg/kg or more, depending on the factors mentioned above. Typically, the clinician will administer the molecule until a dosage is reached that achieves the desired effect. The progress of this therapy is easily monitored by conventional assays.

Depending on the type and severity of the disease, from about 0.001 mg/kg to about 1000 mg/kg, more preferably about 0.01 mg to 100 mg/kg, more preferably about 0.010 to 20 mg/kg of the agohist antibody might be an initial candidate dosage for administration to the patient, whether, for example, by one or more separate administrations, or by continuous infusion. For repeated administrations over several days or longer, depending on the condition, the treatment is repeated until a desired suppression of disease symptoms occurs or the desired improvement in the patient's condition is achieved. However, other dosage regimens may also be useful.

The present invention will now be illustrated by the following Examples, which are not intended to be limiting in any way. The disclosures of all literature references cited in the specification are expressly incorporated herein by reference.

EXAMPLE 1

IDENTIFICATION AND ISOLATION OF pTK GENES

To facilitate the isolation and identification of these novel pTK genes, two sets of DNA probes were generally used (see Table 1).

The first set consisted of two degenerate oligonucleotide sequences, pTK 1 (SEQ ID NO: 1) and pTK 2 (SEQ ID NO: 2). These sequences were used as polymerase chain reaction (PCR) primers, using standard PCR techniques, to amplify tyrosine kinase DNA segments.

The second set consisted of two oligonucleotide sequences, pTK 3 (SEQ ID NO: 3) and pTKKW (SEQ ID NO: 4) selected from the highly conserved regions of the catalytic domains of the c-kit subgroup of protein tyrosine kinases. These sequences were also used as polymerase chain reaction primers in a second round of DNA amplification. Using this two-step amplification procedure, DNA fragments which hybridized to these pTK primers were identified, isolated and subsequently sequenced using known laboratory techniques.

The reaction product was electrophoretically separated on a 2% low-melting agarose gel, purified on an Elutip-D column (Schleicher & Schuell) digested with EcoR1 and BamH1, and subcloned into pUC19.

Recombinants were sequenced by the Sanger dideoxy method and evaluated by the FASTA nucleic acid sequence analysis program. One clone termed HpTK5 (214 bp) was radiolabelled by random priming and used to screen an oligo dT-primed lambda gt10 Hep3B cDNA library. DNA was isolated from 17 positive phage plaques and inserts were subcloned into the EcoR1 site of pBluescript (Stratagene La Jolla, Calif.). The largest insert, a 3969 bp cDNA, was sonicated to an average size of 800–2000 bp and cloned into the Sma1 site of M13. Overlapping clones were sequenced using the Taq Dye Primer Cycle Method (CABI) on the

TABLE 1

| Probe name | Sequence |
|---|---|
| | First Round of Amplification |
| pTK1 | 5'-CGGATCCACAGNGACCT-3' (SEQ ID NO: 1) |
| pTK2 | 5'-GGAATTCCAAAGGACCAGACGTC-3' (SEQ ID NO: 2) |
| | Second Round of Amplification |
| pTK3 (kit family specific) | 5'-CGGATCCATCCACAGAGATGT-3' (SEQ ID NO: 3) |
| pTKKW (kit family specific) | 5'-GGAATTCCTTCAGGAGCCATCCACTT-3' (SEQ ID NO: 4) |

EXAMPLE 2

ISOLATION AND CHARACTERIZATION OF HpTK5

A. DNA Amplification and Cloning of HpTK5

Light density human bone marrow mononuclear cells, obtained from normal volunteers using Deaconess Hospital Institutional Review Board approved protocols and with voluntary written informed consent, were separated by anti-CD34 antibody (AMAC, Westbrook, Me.) and immunomagnetic beads (Dynal, Oslo, Norway). Flow cytometric analysis using FITC-conjugated anti-CD34 antibody (AMAC) confirmed ~95% CD34 positivity of isolated cells. The hepatoma cell line, Hep3B, was cultured in alpha medium (Gibco, Grand Island, N.Y.) supplemented with penicillin (100 U/mL), streptomycin (100 µg/mL) and 10% fetal bovine serum (Gibco) at 37° C. in a 5% $CO_2$ incubator. Total RNA extracted from CD34+ bone marrow mononuclear or Hep3B cells was reverse transcribed with random primers and the Moloney murine leukemia virus reverse transcriptase (RT) following the conditions of the manufacturer (Gibco-BRL) in a 20 µl reaction. PCR was performed on the RT reaction product in a 100 µl reaction containing 50 mM KCl, 10 mM Tris-HCl (pH 8.4), 1.5 MgCl, 20 µg/ml gelatin, 0.2 mM dNTPs, 2.5 units Taq polymerase (Perkin-Elmer/Cetus) and 50 pmol each of pTK-specific degenerate primers [pTK1 5'TCGGATCCACA/CGNGAC/TC/TTGGC 3' (SEQ ID NO. 37), pTK1B 5'TCGGATCCAC/TC/AGNGAC/TC/TTNGCNGC 3' (SEQ ID NO. 38), pTK2 5'CTCGAATTCCA/GA/TAA/GC/GT/ACCAG/CACA/GTC 3' (SEQ ID NO. 39), pTK2B 5'CTCGAATTCCA/GA/TAT/CC/GT/ACCAT/AACA/GTC 3'(SEQ ID NO. 40)] derived from consensus regions among known pTKs as previously reported by others (Hanks et al., Science, 241:42–52 [1988]; Wilks, Proc. Nat. Acad. Sci., USA 86:1603–1607 [1989]; and Matthews et al., Cell 65:1143–1152 [1991]). The PCR cycle was 1.5 min at 95° C., 2 min at 37° C. and 3 min at 63° C. repeated 35 times.

Catalyst 800 Molecular Biology Lab Station (ABI). Sequencing reactions were then analyzed on the ABI 373A Automated DNA Sequenator.

A single full-length 3969 bp cDNA was isolated and sequenced. (FIGS. 8A–8F). The full length clone, named hepatoma transmembrane kinase (HTK) or HpTK5, included an open reading frame extending from nucleotide 90 to 3050 predicted to encode a 987 amino acid protein of 108,270 Dalton. The putative initiation codon is preceded by an in-frame stop codon beginning at base 78. Preceding the open reading frame is a 5' untranslated region which is GC-rich as is characteristic for many growth factors or growth factor receptors (Kozak, J. Cell Biol. 115:887–903 [1991]).

The predicted protein sequence includes a transmembrane region (aa 538–563) which divides HpTK5 into extracellular (ECD) and intracellular domains (ICD). The ECD of 538 amino acids includes a signal peptide of 15 amino acids and a cysteine-rich box containing 20 Cys residues. In addition, there are two fibronectin type III repeats spanning aa 321 to 425 and 435 to 526. Ash at positions 208, 340 and 431 are possible sites for N-glycosylation.

The putative intracellular domain (ICD) contains a kinase consensus region from position 613 through 881. This kinase region includes a putative ATP-binding consensus (Gly-X-Gly-X-X-Gly) in subdomain I at positions 622–627. A Lys at position 647 (subdomain II) corresponds to an invariant Lys among tyrosine kinases thought to be critical for the phosphotransfer reaction. Signature regions indicative of substrate specificity suggest that HpTK5 is a tyrosine rather than a serine/threonine kinase. These include the sequence at positions 740–745 in subdomain VI and the sequence at positions 783–790 in subdomain VIII. Tyrosine residues at positions 601, 619 and 741 are possible substrates for tyrosine kinase activity.

The predicted amino acid sequence of HpTK5 most closely resembles that of the subfamily originally defined by EPH. The pattern of expression of the EPH subfamily is suggestive of a role in differentiation and development. In particular, the emergence of neural elements corresponds with the expression of certain EPH-related genes. The EPH family receptors, Hek2 and Elk, are the most closely related pTKs to HpTK5. They share 79.3 and 76.5% identity within the ICD respectively and 45 and 42% identity within the ECD respectively.

B. Chromosome Mapping of HpTK5

Somatic cell hybrid DNAs from a panel of 25 human-hamster cell lines (Bios, New Haven, Conn.) were used for chromosome localization by PCR. Two sets of primers from the 3' untranslated region of HpTK5 were chosen. PCR was performed with 250 ng DNA and 50 pmol each of the 5' and 3' primers, 50 mM KCl, 1.5 mM MgCl$_2$, 20 μg/ml gelatin, 0.2 mM dNTPs and 2.5 units Taq polymerase in a final volume of 100 μl. Cycles of 94° C. for 30 sec, 60° C. for 30 sec and 72° C. for 30 sec were repeated 30 times. A portion of each sample (15 μl) was electrophoresed through a 1.5% agarose gel, transferred to a nylon membrane and hybridized to a $^{32}$P-labelled full length HpTK5 cDNA probe prior to 5 hour autoradiography. Positives were scored and compared to a matrix summary of human chromosomal material present in each of the somatic cell hybrid DNAs.

The 3'-untranslated region characteristically contains few, if any, intervening sequences and has a high degree of diversity among members of gene families making it preferred in this type of analysis. Both sets of primers gave results that were consistent with human chromosome 7 only. Human chromosome 7 also includes the genes for the EGF receptor, hepatocyte growth factor (HGF) receptor, HGF, platelet-derived growth factor (PDGF) and interleukin-6. Karyotypic abnormalities involving this chromosome are common among human leukemias, particularly in aggressive myeloid leukemias that occur following radiation, alkylating agent chemotherapy or a pre-existing myelodysplastic condition (Baer et al., Curr. Opin. Oncol. 4:24–32 [1992]).

C. Northern Blotting of HpTK5

Poly-A selected RNA was electrophoresed through a 1.2% agarose, 2.2M formaldehyde gel and transferred to a nylon filter. Prepared or commercially obtained filters were hybridized in 50% formamide at 42° C. to 32-P labeled HpTK5, glyceraldehyde-3-phosphate dehydrogenase (GAPDH) or actin cDNA inserts and washed under stringent conditions (final wash: 0.1×SSC, 0.2% SDS at 65° C.). SSC is 0.15M NaCl/0.015M Na$_3$-citrate, pH 7.6. Northern blots of human fetal or adult tissue RNA were obtained from Clontech (Palo Alto, Calif.) and contained 2 μg/lane of poly A selected RNA.

Northern blot analysis of human fetal tissues revealed a single transcript of ~4 Kb in heart, lung, liver and kidney, with a lesser signal detectable in brain. In adult human tissue, no signal was detectable in brain, while placenta had a particularly intense signal followed by kidney, liver, lung and pancreas. Skeletal muscle and heart were of lower signal intensity.

HpTK5 expression in human tumor cell lines was also analyzed by Northern blot analysis performed as discussed above. Cell lines derived from liver, breast (MCF 7), colon (Colo 205), lung (NCI 69), melanocyte (HM-1) or cervix (HeLa) had detectable signal of appropriate size. Message was present in select cell lines of hematopoietic origin. K562 (a primitive myeloid cell with multipotential), THP-1 (a monocytoid cell), U937 (a myelomonocytic cell line), Hep3B (a human hepatocarcinoma cell line), and CMK (of megakaryocytic origin) were all positive for HpTK5 message, but lymphoid (H9, Jurkat, JH-1, Raji, Ramos) or select other myeloid cells (KG-1 or KMT2) had no detectable transcript by Northern analysis.

Differential expression of the HpTK5 transcript in fetal versus adult brain suggests that HpTK5 may share, with other EPH subfamily members, a role in events related to neural development. However, unlike some members of the EPH subfamily which are exclusively expressed in neurons (Maisonpierre et al., supra), HpTK5 is widely expressed in other tissues. In particular, HpTK5 is expressed in hematopoietic cells including CD34+ hematopoietic progenitor cells. The presence of the HpTK5 message in early hematopoietic cells and cell lines of myeloid lineage, but not in cell lines derived from lymphoid cells, suggests that HpTK5 may have lineage restricted expression.

EXAMPLE 3

PRODUCTION OF POLYCLONAL ANTIBODIES

An HpTK5 extracellular domain (ECD)-human IgG$_1$ Fc fusion gene was constructed and fusion protein produced as previously described (Bennett et al., J. Biol. Chem. 266:23060–23067 [1991]). Polyclonal antibodies were generated in New Zealand White rabbits against the fusion protein; 4 μg in 100 μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sig et al., Methods Enzymol. 93:3–12 [1983]). For subsequent boosts, the protein was injected into subcutaneous and intramuscular sites. 1.3 μg protein/kg body weight was injected every 3 weeks with bleeds taken 1 and 2 weeks following each boost. HpTK5 specificity of the immunized rabbit serum was assessed by flow cytometric analysis of NIH3T3 cells transfected with full length HpTK5 or vector alone using a 1:200 dilution of pre-immune serum or anti-HpTK5-IgG Fc serum. Significant peak shifts were observed in several HpTK5 expressing clones as compared to either pre-immune serum or vector alone transfectant controls.

EXAMPLE 4

UTILITY AND AGONIST ACTIVITY OF POLYCLONAL ANTIBODIES

A. FLAG-HpTK5 Fusion Construct

Overlapping oligonucleotides encoding a 12 amino acid peptide having the sequence MDYKDDDDKKLAM (SEQ ID NO: 41) which includes the 4 amino acid antibody recognition site "FLAG" (IBI, New Haven, Conn.) a 5'-EcoRV restriction site and a 3'-NcoI restriction site (5'-CCGGATATCATGGACTACAAGGACGAC-GATGACAAGAAGCTTGCCATGGAGCTC; SEQ ID NO: 42), were ligated into the NcoI site (base 88) of HpTK5 in the EcoRV digested Bluescript (Stratagene, La Jolla, Calif.) vector.

B. In vitro Transcription and Translation

Transcription was performed on 2 pmol of linearized HpTK5 or FLAG-HpTK5 containing plasmid at 37° C. for 1 h in 50 μl volume. containing 10 mM dithiothreitol, 2.5 μg bovine serum albumin, 0.25 mM each dNTP, 0.5M m7GRNA cap (New England Biolabs, Beverly, Mass.), 2.5 units RNasin (Promega, Madison, Wis.), 3 units T3 RNA polymerase (Pharmacia, Piscataway, N.J.). 1 μg of DNAase (New England Biolabs, Beverly, Mass.) was added for 15 min at 37° C. prior to phenol/chloroform extraction and ethanol precipitation. Translation was performed using the Promega rabbit reticulocyte lysate kit according to the manufacturer's specifications with or without $^{35}$S- methionine (350 µCi) labeling. Sample buffer containing SDS and beta-mercaptoethanol (2-ME) was added before boiling and 10% SDS-PAGE.

C. HpTK5 Expression in NIH3T3 Cells

A 4038 bp Cla1-Xba1 cDNA fragment containing 32 bp of linker sequence, 37 bp of pBluescript (Stratagene La Jolla, Calif.) polylinker and the entire 3969 bp HpTK5 cDNA was subcloned into the expression vector pRIS (Genentech, Inc.) under the control of the Rous sarcoma virus LTR promoter. NIH3T3 cells maintained in high glucose Dulbecco's Modified Eagle's Medium (DMEM) supplemented with 10% FCS were co-transfected with pRIS-HpTK5 and pNeo (an SV40 based vector containing the neomycin resistance marker) by the calcium phosphate method as described by Gorman et al., in *DNA Prot. Engineer. Tech.* 2:3–10 [1990]. Neomycin resistant colonies were selected 48 hours after transfection with Geneticin (Gibco/BRL) at 400 µg/ml. Fourteen days later individual resistant colonies were isolated, expanded and analyzed by flow cytometry for HpTK5 expression using rabbit polyclonal antiserum.

D. Immunoprecipitation

Cells (Hep3B, control NIH3T3 or HpTK5 transfected NIH3T3) or in vitro translated protein (HpTK5 or FLAG-HpTK5) were used for immunoprecipitation with either serum (pre-immune or anti-HpTK5-IgG Fc) or monoclonal antibody (FLAG-specific, M2, or isotype control) (IBI, Rochester, N.Y.). Subconfluent cells were labeled with 200 µCi/ml $^{35}$S-methionine for 18 hours and lysed in lysis buffer (150 mM NaCl, 50 mM Tris-HCl pH8.0, 1 mM EDTA, 0.025 Na azide, 1% NP-40, 0.1% SDS, 10% Glycerol, 0.5% Na deoxycholate, 1 mM phenylmethylsulfonyl flouride (PMSF), 10 µg/ml aprotinin, 10 µg/ml leupeptin and 50 µM Na vanadate) for 30 min on ice. The cell lysate was centrifuged (12,000×g) for 10 min at 4° C. Cell lysate supernatant or in vitro translation mixture was precleared with 0.05 volume of normal rabbit serum and adsorbed with 0.05 volume of *Staphylococcus aureus* protein-A Sepharose CL4B. After centrifugation, preimmune or immune serum (1:100 dilution), or monoclonal antibody, was added and rocked overnight at 4° C. before 100 µl of protein-A Sepharose CL4B was added and the solution rocked 4° C. for additional 2 h. Immunoprecipitates were washed, suspended in SDS/PAGE loading buffer (10% glycerol, 5% 2-ME, 2.3% SDS and 62.5 mM Tris-HCl pH 6.8), heated to 95° C. for 5 min and analyzed by 7.5% SDS-PAGE.

E. Cell Fractionation

Cell fractionation of Hep3B cells was performed to confirm the membrane localization of HpTK5 predicted by its amino acid sequence. Hep-3B cells (1×10$^7$) were labeled with 200 µCi/ml $^{35}$S-methionine in alpha MEM medium containing 10% dialyzed FCS overnight. The cells were washed twice with cold PBS, scraped into 1 ml of cold buffer (20 mM Tris-HCl pH 7.5, 2 mM EDTA, 5 mM EGTA, 0.25M sucrose, 0.01% leupeptin, 4 mM PMSF, 10 mM 2-ME) and disrupted by sonication for 40 seconds. Whole homogenates were centrifuged at 12,000×g for 15 min, the nuclear pellets isolated and the decanted supernatant centrifuged at 140,000×g for 40 min at 4° C. to pellet membranes. The resultant supernatant served as the cytosolic (C) fraction. Nuclear (N) and membrane (M) fractions were washed and dissolved in buffer containing 0.5% NP-40 prior to immunoprecipitation. The C, N or M fractions were immunoprecipitated with an anti-HpTK5 or pre-immune (control) serum, subjected to 12% SDS-PAGE and autoradiographed. HpTK5 segregated predominantly with the membrane fraction, though immunoprecipitated material was evident to a lesser extent in cytosol.

F. Protein Kinase Assay

Immunoprecipitates were washed once with kinase buffer (25 mM Hepes pH7.4, 1 mM DTT, 10 mM MgCl 10 mM MnCl), and resuspended in 40 µl of kinase buffer containing either unlabeled ATP or 10 µCi of $^{32}$P-ATP (3000 Ci/mM). After a 10 min incubation at 30° C., the reaction was stopped by adding 40 µl of 2× sample buffer and boiling the samples for 3 min prior to electrophoresis on 8.0% SDS-PAGE gel. The dried gel was covered with 4 sheets of aluminum foil to block $^{35}$S-labelled protein autoradiography and the gel was placed under film for 5 hours to overnight.

G. Western Blotting and Phosphotyrosine Assay

Proteins were electrophoretically transferred to a 0.2 µm nitrocellulose (Bio-Rad) or a 0.45 µm polyvinylidene diflouride (Millipore) membrane in a buffer containing 25 mM Tris-HCl (pH 7.5), 192 mM glycine and 20% methanol at 100 mA for 2 h. Filters were washed in TBS (10 mM Tris-HCl pH 8.0, 150 mM NaCl) blocked by incubating in TBST (TBS with 0.05% Tween-20) plus 5% BSA overnight. Filters were washed four times for 5 min each in TBST and incubated for 2 h with 4G10 anti-phosphotyrosine antibody from UBI (1:1000 dilution in TBST). Filters were washed four times for 5 min each in TBST and incubated for 1 h with the alkaline phosphatase labelled anti-mouse secondary antibody (Promega) at a 1:7500 dilution in TBST. After washing four times, the blot was developed for 30–60 min in AP buffer (100 mM Tris-HCl, 100 mM NaCl, 5 mM MgCl$_2$) plus BCIP, NBT substrates.

H. Antibody Induced Phosphorylation Assay

Rabbit antisera to HpTK5-IgG Fc were tested for their ability to induce HpTK5 phosphorylation in HpTK5 transfected NIH3T3 cells. Cells were plated at a density of 5×10$^5$ cells/well in a 6-well plate and, after 24 hours, were serum starved for 1 hour prior to adding pre-immune or immune serum at a 1:50 dilution for 30 minutes. Cells were then washed in PBS and lysed in either 2× sample buffer or NP-40 lysis buffer as described above. Either crude lysates or immunoprecipitated cell lysates were then separated via 4–12% gradient SDS-PAGE and analyzed by anti-phosphotyrosine immunoblot as described above. HpTK5 expressing cells were exposed to antisera and separated by SDS-PAGE either with or without immunoprecipitation. The electrotransferred gel was immunoblotted with anti-phosphotyrosine antibody. Enhanced tyrosine phosphorylation of HpTK5 was observed following exposure to polyclonal antiserum showing an agohist-like effect of antibody binding. Interaction of HpTK5 with an antibody directed against its ECD induces phosphorylation. This provides further support that HpTK5 may serve as a receptor for a ligand that triggers kinase activation. Details of the signaling pathway of HpTK5 may be further explored using antisera as a surrogate ligand.

I. Conclusions

An HpTK5 ECD-IgG Fc fusion protein was expressed, purified and used to generate rabbit anti-serum which immunoprecipitated a 120 kD protein from Hep3B cells. The specificity of the antiserum was confirmed by immunoprecipitation of in vitro translated HpTK5 RNA and HpTK5 transfected NIH3T3 cells. To determine the functional capacity of HpTK5, in vitro translated HpTK5 was immunoprecipitated, exposed to kinase conditions and immunoblotted using a phosphotyrosine specific monoclonal antibody. The data obtained indicated that HpTK5 is phosphorylated on tyrosine. However, the presence of other bands consistently appearing in the $^{32}$P-labelled immunoprecipitation suggested that HpTK5 protein was only partially purified and therefore, it could not be concluded that HpTK5 was enzymatically active. To overcome this problem, a fusion construct was generated in which an 8 amino acid epitope (FLAG) was added to the N-terminus of HpTK5. The FLAG-HpTK5 fusion was in vitro translated and immunoprecipitated with a FLAG-specific monoclonal antibody resulting in a single protein of appropriate size (~120 kD). When subjected to kinase conditions in the presence of $^{32}$P-ATP, the HpTK5-FLAG fusion protein was labelled on tyrosine confirming tyrosine autophosphorylation and thereby, the kinase function of HpTK5.

EXAMPLE 5

PRODUCTION OF MONOCLONAL ANTIBODIES

Anti-HpTK5 monoclonal antibodies were produced by hyperimmunizing BALB/c mice intraperitoneally with the HpTK5 extracellular domain (ECD)-human $IgG_1$ Fc fusion protein (produced using the techniques disclosed above) in RIBI adjuvant (RIBI ImmunoChem Research, Hamilton, Mont.) and fusing splenocytes with the mouse myeloma cell line X63-Ag8.653 (Kearney et al., *J. Immunol.* 23:1548–1550 [1979]). The antibodies were purified fluid using protein A-Sepharose (Repligen Corp., Cambridge, Mass.) and established affinity chromatography methods (Goding, J. W., *J. Immunol. Methods* 20:241–253 [1978]).

Monoclonat antibodies were screened for their ability to bind the HpTK5 antigen. Starting on day 15 post fusion, culture supernatants were harvested from the fusion plates and assayed for their ability to specifically "capture" HpTK5-IgG. In this ELISA assay, goat anti-mouse IgG was coated onto 96 well microtiter plates. The culture supernatants (100 µl) were added to the wells and the mouse IgG present was bound by the goat anti-mouse IgG antibodies. The plates were washed and either HpTK5-IgG or CD4-IgG (100 µl at 6 nM) was added. The "captured" immunoadhesin was detected using a goat anti-hu (Fc specific) horseradish peroxidase conjugate and orthophenylene diamine substrate. Quantitation of substrate catalysis was determined by optical density at 490 nm.

Agonist antibodies were then screened for using the techniques. disclosed in Example 6 below. Two agohist monoclonal antibodies were identified, one of which has been deposited with the ATCC.

EXAMPLE 6

AGONIST ACTIVITY OF MONOCLONAL ANTIBODIES

The monoclonal antibodies produced using the techniques disclosed in Example 5 were tested for their ability to induce HpTK5 phosphorylation in HpTK5 transfected NIH3T3 cells. Cells were plated at a density of $5 \times 10^5$ cells/well in a 6-well plate and, after 24 hours, were serum starved for 1 hour prior to adding preimmune serum or anti-HpTK5 monoclonal antibody (undiluted conditioned hybridoma media was used) for 30 minutes. Cells were then washed in PBS and lysed in either 2× sample buffer or NP-40 lysis buffer as described above. Either crude lysates or immunoprecipitated cell lysates were then separated via 4–12% gradient SDS-PAGE and analyzed by anti-phosphotyrosine immunoblot as described above. HpTK5 expressing cells were exposed to the monoclonal antibody and separated by SDS-PAGE either with or without immunoprecipitation. The electrotransferred gel was immunoblotted with anti-phosphotyrosine antibody. Enhanced tyrosine phosphorylation of HpTK5 was observed following exposure to monoclonal antibodies showing an agonist-like effect of antibody binding. Accordingly, interaction of HpTK5 with a monoclonal antibody directed against its ECD is able to induce phosphorylation of the kinase domain thereof.

Deposit of Materials

The following culture has been deposited with the American Type Culture Collection, 12301 Parklawn Drive, Rockville, Md., 20852 U.S.A. (ATCC):

| Hybridoma | ATCC No. | Deposit Date |
| --- | --- | --- |
| Anti-HpTK5 | HB 11,583 | March 15, 1994 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the culture deposited, since the deposited embodiment is intended as a single illustration of one aspect of the invention and any culture that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An agonist monoclonal antibody which binds to an extracellular domain of HpTK 5 receptor protein tyrosine kinase and activates a tyrosine kinase domain of the HpTK 5 receptor.

2. The monoclonal antibody of claim 1 capable of binding to the same human HpTK5 epitope as that recognized by the antibody produced by the hybridoma cell line deposited under American Type Culture Collection Accession No. ATCC HB 11,583.

3. A hybridoma cell line which produces the antibody of claim 1.

4. The hybridoma cell line of claim 3 which is the hybridoma cell line deposited under American Type Culture Collection Accession No. ATCC HB 11,583, producing monoclonal antibody anti-HpTK5.

5. A composition comprising the antibody of claim 1 in an amount effective in activating the kinase domain of the HpTK 5 receptor and a pharmaceutically acceptable carrier.

6. The antibody of claim 1 which is humanized.

7. The antibody of claim 2 which is humanized.

* * * * *

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

CGGATCCACA GNGACCT 17

( 2 ) INFORMATION FOR SEQ ID NO:2:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGAATTCCAA AGGACCAGAC GTC 23

( 2 ) INFORMATION FOR SEQ ID NO:3:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGGATCCATC CACAGAGATG T 21

( 2 ) INFORMATION FOR SEQ ID NO:4:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGAATTCCTT CAGGAGCCAT CCACTT 26

( 2 ) INFORMATION FOR SEQ ID NO:5:

( i ) SEQUENCE CHARACTERISTICS:
        ( A ) LENGTH: 160 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGATCCTGTG CATCAGTGAC TTAGGGCTAG GAACATTCTG CTGTCGGAAA 50

GCGACGTGGT GAAGATCTGT GACTTTGGCC TTGCCCGGGA CATCTACAAA 100

GACCCCAGCT ACGTCCGCAA GCATGCCCGG CTGCCCCTGA AGTGGATGGC 150

GCCAGAATTC 160

( 2 ) INFORMATION FOR SEQ ID NO:6:

( i ) SEQUENCE CHARACTERISTICS:
 ( A ) LENGTH: 53 amino acids
 ( B ) TYPE: amino acid
 ( D ) TOPOLOGY: linear ( x i ) SEQUENCE DESCRIPTION: SEQ ID NO:6:

```
Asp Pro Val His Gln Xaa Leu Arg Ala Arg Asn Ile Leu Leu Ser
 1               5                   10                  15

Glu Ser Asp Val Val Lys Ile Cys Asp Phe Gly Leu Ala Arg Asp
                20                  25                  30

Ile Tyr Lys Asp Pro Ser Tyr Val Arg Lys His Ala Arg Leu Pro
                35                  40                  45

Leu Lys Trp Met Ala Pro Glu Phe
                50          53
```

( 2 ) INFORMATION FOR SEQ ID NO:7:

( i ) SEQUENCE CHARACTERISTICS:
  ( A ) LENGTH: 147 bases
  ( B ) TYPE: nucleic acid
  ( C ) STRANDEDNESS: single
  ( D ) TOPOLOGY: linear ( x i ) SEQUENCE DESCRIPTION: SEQ ID NO:7:

```
GGATCCATTC ACAGAGACCT AGCAGCACGC AACATCCTGG TCTCAGAGGA  50

CCTGGTAACC AAGGTCAGCG ACTTTGGCCT GGCCAAAGCC GAGCGGAAGG 100

GGCTAGACTC AAGCCGGCTG CCCGTCAAAT GGATGGCTCC CGAATTC    147
```

( 2 ) INFORMATION FOR SEQ ID NO:8:

( i ) SEQUENCE CHARACTERISTICS:
  ( A ) LENGTH: 49 amino acids
  ( B ) TYPE: amino acid
  ( D ) TOPOLOGY: linear ( x i ) SEQUENCE DESCRIPTION: SEQ ID NO:8:

```
Gly Ser Ile His Arg Asp Leu Ala Ala Arg Asn Ile Leu Val Ser
 1               5                   10                  15

Glu Asp Leu Val Thr Lys Val Ser Asp Phe Gly Leu Ala Lys Ala
                20                  25                  30

Glu Arg Lys Gly Leu Asp Ser Ser Arg Leu Pro Val Lys Trp Met
                35                  40                  45

Ala Pro Glu Phe
            49
```

( 2 ) INFORMATION FOR SEQ ID NO:9:

( i ) SEQUENCE CHARACTERISTICS:
  ( A ) LENGTH: 149 bases
  ( B ) TYPE: nucleic acid
  ( C ) STRANDEDNESS: single
  ( D ) TOPOLOGY: linear ( x i ) SEQUENCE DESCRIPTION: SEQ ID NO:9:

```
GTTGGAATTC CTTCCGGCGC CATCCATTTC ACCGGCAGCT TTATTTCGTG  50

TCTAGATTCA TAGATGTCTT CATTATCTAC CTTAAAAACT CTGGCAAGTC 100

CAAAATCTGC TACTTTGTAG ATATTATGTT CACCAACGAG GACATTCCT  149
```

( 2 ) INFORMATION FOR SEQ ID NO:10:

( i ) SEQUENCE CHARACTERISTICS:

( A ) LENGTH: 47 amino acids
( B ) TYPE: amino acid
( D ) TOPOLOGY: linear ( x i ) SEQUENCE DESCRIPTION: SEQ ID NO:10:

```
Val Gly Ile Pro Ser Gly Ala Ile His Phe Thr Gly Ser Phe Ile
 1               5                  10                  15

Ser Cys Leu Asp Ser Met Ser Ser Leu Ser Thr Leu Lys Thr Leu
                20                  25                  30

Ala Ser Pro Lys Ser Ala Thr Leu Ile Leu Cys Ser Pro Thr Arg
                35                  40                  45

Thr Phe
     47
```

( 2 ) INFORMATION FOR SEQ ID NO:11:

( i ) SEQUENCE CHARACTERISTICS:
  ( A ) LENGTH: 151 bases
  ( B ) TYPE: nucleic acid
  ( C ) STRANDEDNESS: single
  ( D ) TOPOLOGY: linear ( x i ) SEQUENCE DESCRIPTION: SEQ ID NO:11:

GTGCACAGGG ATCTCGCGGC TCGGAACATC CTCGTCGGGG AAAACACCCT 50

CTCGAAAGTT GGGGACTTCG GGTTAGCCAG GCTTATCAAG GAGGACGTCT 100

ACCTCTCCCA TGACCACAAT ATCCCCTACA AATGGATGGC CCCTGAGGGA 150

A 151

( 2 ) INFORMATION FOR SEQ ID NO:12:

( i ) SEQUENCE CHARACTERISTICS:
  ( A ) LENGTH: 50 amino acids
  ( B ) TYPE: amino acid
  ( D ) TOPOLOGY: linear ( x i ) SEQUENCE DESCRIPTION: SEQ ID NO:12:

```
Val His Arg Asp Leu Ala Ala Arg Asn Ile Leu Val Gly Glu Asn
 1               5                  10                  15

Thr Leu Ser Lys Val Gly Asp Phe Gly Leu Ala Arg Leu Ile Lys
                20                  25                  30

Glu Asp Val Tyr Leu Ser His Asp His Asn Ile Pro Tyr Lys Trp
                35                  40                  45

Met Ala Pro Glu Gly
                50
```

( 2 ) INFORMATION FOR SEQ ID NO:13:

( i ) SEQUENCE CHARACTERISTICS:
  ( A ) LENGTH: 137 bases
  ( B ) TYPE: nucleic acid
  ( C ) STRANDEDNESS: single
  ( D ) TOPOLOGY: linear ( x i ) SEQUENCE DESCRIPTION: SEQ ID NO:13:

GTTCACCGAG ATCTCAAGTC CAACAACATT TTGCTGCTGC AGCCCATTGA 50

GAGTGACGAC ATGGAGCACA AGACCCTGAA GATCACCGAC TTTGGCCTGG 100

CCCGAGAGTG GCACAAAACC ACACAAATGA GTGCCGC 137

( 2 ) INFORMATION FOR SEQ ID NO:14:

( i ) SEQUENCE CHARACTERISTICS:

(A) LENGTH: 45 amino acids
(B) TYPE: amino acid
(D) TOPOLOGY: linear (xi) SEQUENCE DESCRIPTION: SEQ ID NO:14:

| Val | His | Arg | Asp | Leu | Lys | Ser | Asn | Asn | Ile | Leu | Leu | Leu | Gln | Pro |
|---|---|---|---|---|---|---|---|---|---|---|---|---|---|---|
| 1 | | | | 5 | | | | | 10 | | | | | 15 |

| Ile | Glu | Ser | Asp | Asp | Met | Glu | His | Lys | Thr | Leu | Lys | Ile | Thr | Asp |
|---|---|---|---|---|---|---|---|---|---|---|---|---|---|---|
| | | | | 20 | | | | | 25 | | | | | 30 |

| Phe | Gly | Leu | Ala | Arg | Glu | Trp | His | Lys | Thr | Thr | Gln | Met | Ser | Ala |
|---|---|---|---|---|---|---|---|---|---|---|---|---|---|---|
| | | | | 35 | | | | | 40 | | | | | 45 |

(2) INFORMATION FOR SEQ ID NO:15:

(i) SEQUENCE CHARACTERISTICS:
(A) LENGTH: 211 bases
(B) TYPE: nucleic acid
(C) STRANDEDNESS: single
(D) TOPOLOGY: linear (xi) SEQUENCE DESCRIPTION: SEQ ID NO:15:

GTCAATCGTG ACCTCGCCGC CCGAAATGTG TTGCTAGTTA CCCAACATTA 50

CGCCAAGATC AGTGATTTCG GACTTTCCAA AGCACTGCGT GCTGATGAAA 100

ACTACTACAA GGCCCAGACC CATGGAAAGT GGCCTGTCAA GTGGTACGCT 150

CCGGAATGCA TCAACTACTA CAAGTTCTCC AGCAAAAGCG ATGTCTGGTC 200

CTTTGGAATT C 211

(2) INFORMATION FOR SEQ ID NO:16:

(i) SEQUENCE CHARACTERISTICS:
(A) LENGTH: 70 amino acids
(B) TYPE: amino acid
(D) TOPOLOGY: linear (xi) SEQUENCE DESCRIPTION: SEQ ID NO:16:

| Val | Asn | Arg | Asp | Leu | Ala | Ala | Arg | Asn | Val | Leu | Leu | Val | Thr | Gln |
|---|---|---|---|---|---|---|---|---|---|---|---|---|---|---|
| 1 | | | | 5 | | | | | 10 | | | | | 15 |

| His | Tyr | Ala | Lys | Ile | Ser | Asp | Phe | Gly | Leu | Ser | Lys | Ala | Leu | Arg |
|---|---|---|---|---|---|---|---|---|---|---|---|---|---|---|
| | | | | 20 | | | | | 25 | | | | | 30 |

| Ala | Asp | Glu | Asn | Tyr | Tyr | Lys | Ala | Gln | Thr | His | Gly | Lys | Trp | Pro |
|---|---|---|---|---|---|---|---|---|---|---|---|---|---|---|
| | | | | 35 | | | | | 40 | | | | | 45 |

| Val | Lys | Trp | Tyr | Ala | Pro | Glu | Cys | Ile | Asn | Tyr | Tyr | Lys | Phe | Ser |
|---|---|---|---|---|---|---|---|---|---|---|---|---|---|---|
| | | | | 50 | | | | | 55 | | | | | 60 |

| Ser | Lys | Ser | Asp | Val | Trp | Ser | Phe | Gly | Ile |
|---|---|---|---|---|---|---|---|---|---|
| | | | | 65 | | | | | 70 |

(2) INFORMATION FOR SEQ ID NO:17:

(i) SEQUENCE CHARACTERISTICS:
(A) LENGTH: 6827 bases
(B) TYPE: nucleic acid
(C) STRANDEDNESS: single
(D) TOPOLOGY: linear (xi) SEQUENCE DESCRIPTION: SEQ ID NO:17:

TTCGAGCTCG CCCGACATTG ATTATTGACT AGTTATTAAT AGTAATCAAT 50

TACGGGGTCA TTAGTTCATA GCCCATATAT GGAGTTCCGC GTTACATAAC 100

TTACGGTAAA TGGCCCGCCT GGCTGACCGC CCAACGACCC CCGCCCATTG 150

ACGTCAATAA TGACGTATGT TCCCATAGTA ACGCCAATAG GGACTTTCCA 200

```
TTGACGTCAA TGGGTGGAGT ATTTACGGTA AACTGCCCAC TTGGCAGTAC 250
ATCAAGTGTA TCATATGCCA AGTACGCCCC CTATTGACGT CAATGACGGT 300
AAATGGCCCG CCTGGCATTA TGCCCAGTAC ATGACCTTAT GGGACTTTCC 350
TACTTGGCAG TACATCTACG TATTAGTCAT CGCTATTACC ATGGTGATGC 400
GGTTTTGGCA GTACATCAAT GGGCGTGGAT AGCGGTTTGA CTCACGGGGA 450
TTTCCAAGTC TCCACCCCAT TGACGTCAAT GGGAGTTTGT TTTGGCACCA 500
AAATCAACGG GACTTTCCAA AATGTCGTAA CAACTCCGCC CCATTGACGC 550
AAATGGGCGG TAGGCGTGTA CGGTGGGAGG TCTATATAAG CAGAGCTCGT 600
TTAGTGAACC GTCAGATCGC CTGGAGACGC CATCCACGCT GTTTTGACCT 650
CCATAGAAGA CACCGGGACC GATCCAGCCT CCGCGGCCGG GAACGGTGCA 700
TTGGAACGCG GATTCCCCGT GCCAAGAGTG ACGTAAGTAC CGCCTATAGA 750
GTCTATAGGC CCACTTGGCT TCGTTAGAAC GCGGCTACAA TTAATACATA 800
ACCTTATGTA TCATACACAT ACGATTTAGG TGACACTATA GAATAACATC 850
CACTTTGCCT TTCTCTCCAC AGGTGTCCAC TCCCAGGTCC AACTGCACCT 900
CGGTTCTATC GATTGAATTC CCCGGGGATC CTCTAGAGAT CCCTCGACCT 950
CGAGATCCAT TGTGCTGGCG CGGATTCTTT ATCACTGATA AGTTGGTGGA 1000
CATATTATGT TTATCAGTGA TAAAGTGTCA AGCATGACAA AGTTGCAGCC 1050
GAATACAGTG ATCCGTGCCG CCCTAGACCT GTTGAACGAG GTCGGCGTAG 1100
ACGGTCTGAC GACACGCAAA CTGGCGGAAC GGTTGGGGGT TCAGCAGCCG 1150
GCGCTTTACT GGCACTTCAG GAACAAGCGG GCGCTGCTCG ACGCACTGGC 1200
CGAAGCCATG CTGGCGGAGA ATCATAGCAC TTCGGTGCCG AGAGCCGACG 1250
ACGACTGGCG CTCATTTCTG ACTGGGAATG CCCGCAGCTT CAGGCAGGCG 1300
CTGCTCGCCT ACCGCCAGCA CAATGGATCT CGAGGGATCT TCCATACCTA 1350
CCAGTTCTGC GCCTGCAGGT CGCGGCCGCA CTACTCTTTG ATGTATTACT 1400
CATATTACCA AGGAATAACT GGCGGGCACA GGGTCAGGTG CTGAAGGGAC 1450
ATTGTGAGAA GTGACCTAGA AGGCAAGAGG TGAGCCCTCT GTCACGCTGG 1500
CATAAGGGCC GCTTGAGGGC TCTTTGGTCA AGCAGTAACG CCAGTGTCTG 1550
GGAAGGCACC TGTTACTCAG CAGACCATGA AAGGGCGTCT CCCTTTCCTT 1600
GGAGCAGTCA GGGAACACTC TGCTCCACCA GCTTCTTGTG GGAGCCTGGA 1650
TATTATCCAG GCCTGCCCGC AGTCATCCGG AGGCCTAACC CCTCCCTGTG 1700
GTGCTTCAGT GGTCACACTC CTTGTCCACT TTCATGCTCC TCTTGGCCTC 1750
CTGGTTCCTC TTGGAAGTTT GTAGTAGATA GCAGAAGAAA TAGCGAAAGT 1800
CTTAAAGTCT TTGATCTTTC TTATAAGTGC AGAGAAGAAA TGCTGACGTA 1850
TGCTGCCTTC TCTCTCTCTG CTTCAGCTAC CTGAAGCCGC TTTCTTGTCT 1900
ATACCTGCTC TCTATCTGCT CACACTCCTC CGAGGCCAGC ACCATCCCAC 1950
TGTCTGTCTG GTTGTCCACA GAGCCTTTGT AGGTCGTTGG GGTCATGGGG 2000
AATTCCTCAA ATGTCTTCAT CCTGGAGGAA CCACGGGTCT CAGCCCCTCT 2050
GGCCAGGCAC CCGGGAAAGG ACACCCAGTT GTAATACCTG GCGGCCAGGC 2100
TGTGGCGCTG CAGGCTTGGC GGGCTGTCCT CAGCGTCAGC CTGGGCGATG 2150
TGTAGGGCCA TGGTGGACAC CTGCGAGAAG CTGCCCTCTT CTGAGCTCTG 2200
```

```
AGAGCTGCGC GGGGCCATGC AGACCTCCTC TTCCTCTTGC AGGCCCCTGC  2250
CCTGGAGCAG GTCCCCCAGG ATCTCCACCA GCTCCGAGAA TGCAGGTCTC  2300
GCCTTGGGGT CTCCGGACCA GCAGTTCAGC ATGATGCGGC GTATGGCGGG  2350
AGTGGCCAGC TCCGGGGCCC TCATCCTTGT GCCGTCTCTC AGCCGCTGGC  2400
AGAACTCCTC ATTGATCTGC ACCCCAGGGT ACGGGGAGGC CCCCAGAGAG  2450
AAGATCTCCC AGAGAAGCAC CCCAAAGGAC CACACGTCAC TCTGCGTGGT  2500
GTACACCTTG TCGAAGATGC TTTCAGGGGC CATCCACTTC AGGGGCAGCC  2550
GGGCACTGCC CTTGCGGACG TAGTCGGGGT CTTTGTAGAT GTCCCGGGCA  2600
AGGCCAAAGT CACAGATCTT CACCACGTCG CTTTCCGACA GCAGAATGTT  2650
CCGAGCAGCC AGGTCTCTGT GGATGCACTT TCGGAAGCC  AGGAACTCCA  2700
TCCCTCTGGC CACCTGGAAG CTGTAGCAGA CAAGATCTTC CATGGTCAGC  2750
GGGCTCAGCC ACAGGTCCTC AGCTTCTTGG TCTGGAGAAG CCCGCCTCGC  2800
TCCGCCCTCG GTCTTCGAGA ACCGCGCGAA GAGGACCCTG TCGCTGCTCC  2850
CCGGCCGCCT CCGATCCAGC CTGGCGAGCT CCACCATGGC GCGGAAGCGT  2900
CCGCGCTGCT CGGGAGACTT CTCCTGCGGA TGCACGAAGC TGGCTCGAGG  2950
GCGCCCAGTC GTCCGCCGCA GAGGCGCCTC CATTCCCCCG CCGCCCGCGG  3000
CGCCCCGCAG GCCGCCCGCT CACCGNGCAG GGGCTGCGGC CGCGACTCTA  3050
GAGTCGACCT GCAGAAGCTT GGCCGCCATG GCCAACTTTG TTATTGCAG  3100
CTTATAATGG TTACAAATAA AGCAATAGCA TCACAAATTT CACAAATAAA  3150
GCATTTTTTT CACTGCATTC TAGTTGTGGT TTGTCCAAAC TCATCAATGT  3200
ATCTTATCAT GTCTGGATCG ATCGGGAATT AATTCGGCGC AGCACCATGG  3250
CCTGAAATAA CCTCTGAAAG AGGAACTTGG TTAGGTACCT TCTGAGGCGG  3300
AAAGAACCAG CTGTGGAATG TGTGTCAGTT AGGGTGTGGA AAGTCCCCAG  3350
GCTCCCCAGC AGGCAGAAGT ATGCAAAGCA TGCATCTCAA TTAGTCAGCA  3400
ACCAGGTGTG GAAAGTCCCC AGGCTCCCCA GCAGGCAGAA GTATGCAAAG  3450
CATGCATCTC AATTAGTCAG CAACCATAGT CCCGCCCCTA ACTCCGCCCA  3500
TCCCGCCCCT AACTCCGCCC AGTTCCGCCC ATTCTCCGCC CCATGGCTGA  3550
CTAATTTTTT TTATTTATGC AGAGGCCGAG GCCGCCTCGG CCTCTGAGCT  3600
ATTCCAGAAG TAGTGAGGAG GCTTTTTTGG AGGCCTAGGC TTTTGCAAAA  3650
AGCTGTTAAC AGCTTGGCAC TGGCCGTCGT TTTACAACGT CGTGACTGGG  3700
AAAACCCTGG CGTTACCCAA CTTAATCGCC TTGCAGCACA TCCCCCCTTC  3750
GCCAGCTGGC GTAATAGCGA AGAGGCCCGC ACCGATCGCC CTTCCCAACA  3800
GTTGCGTAGC CTGAATGGCG AATGGCGCCT GATGCGGTAT TTTCTCCTTA  3850
CGCATCTGTG CGGTATTTCA CACCGCATAC GTCAAAGCAA CCATAGTACG  3900
CGCCCTGTAG CGGCGCATTA AGCGCGGCGG GTGTGGTGGT TACGCGCAGC  3950
GTGACCGCTA CACTTGCCAG CGCCCTAGCG CCCGCTCCTT TCGCTTTCTT  4000
CCCTTCCTTT CTCGCCACGT TCGCCGGCTT TCCCCGTCAA GCTCTAAATC  4050
GGGGGCTCCC TTTAGGGTTC CGATTTAGTG CTTTACGGCA CCTCGACCCC  4100
AAAAAACTTG ATTTGGGTGA TGGTTCACGT AGTGGGCCAT CGCCCTGATA  4150
GACGGTTTTT CGCCCTTTGA CGTTGGAGTC CACGTTCTTT AATAGTGGAC  4200
```

```
TCTTGTTCCA AACTGGAACA ACACTCAACC CTATCTCGGG CTATTCTTTT   4250
GATTTATAAG GGATTTTGCC GATTTCGGCC TATTGGTTAA AAAATGAGCT   4300
GATTAACAA  AAATTTAACG CGAATTTTAA CAAAATATTA ACGTTACAA    4350
TTTTATGGTG CACTCTCAGT ACAATCTGCT CTGATGCCGC ATAGTTAAGC   4400
CAACTCCGCT ATCGCTACGT GACTGGGTCA TGGCTGCGCC CCGACACCCG   4450
CCAACACCCG CTGACGCGCC CTGACGGGCT TGTCTGCTCC CGGCATCCGC   4500
TTACAGACAA GCTGTGACCG TCTCCGGGAG CTGCATGTGT CAGAGGTTTT   4550
CACCGTCATC ACCGAAACGC GCGAGGCAGT ATTCTTGAAG ACGAAAGGGC   4600
CTCGTGATAC GCCTATTTTT ATAGGTTAAT GTCATGATAA TAATGGTTTC   4650
TTAGACGTCA GGTGGCACTT TTCGGGGAAA TGTGCGCGGA ACCCCTATTT   4700
GTTTATTTTT CTAAATACAT TCAAATATGT ATCCGCTCAT GAGACAATAA   4750
CCCTGATAAA TCTTCAATAA TATTGAAAAA GGAAGAGTAT GAGTATTCAA   4800
ACATTTCCGT GTCGCCCTTA TTCCCTTTTT GGCGGCATTT GCCTTCCTG    4850
TTTTTGCTCA CCCAGAAACG CTGGTGAAAG TAAAAGATGC TGAAGATCAG   4900
TTGGGTGCAC GAGTGGGTTA CATCGAACTG GATCTCAACA GCGGTAAGAT   4950
CCTTGAGAGT TTTCGCCCCG AAGAACGTTT TCCAATGATG AGCACTTTTA   5000
AAGTTCTGCT ATGTGGCGCG GTATTATCCC GTGATGACGC CGGGCAAGAG   5050
CAACTCGGTC GCCGCATACA CTATTCTCAG AATGACTTGG TTGAGTACTC   5100
ACCAGTCACA GAAAAGCATC TTACGGATGG CATGACAGTA AGAGAATTAT   5150
GCAGTGCTGC CATAACCATG AGTGATAACA CTGCGGCCAA CTTACTTCTG   5200
ACAACGATCG GAGGACCGAA GGAGCTAACC GCTTTTTTGC ACAACATGGG   5250
GGATCATGTA ACTCGCCTTG ATCGTTGGGA ACCGGAGCTG AATGAAGCCA   5300
TACCAAACGA CGAGCGTGAC ACCACGATGC CAGCAGCAAT GGCAACAACG   5350
TTGCGCAAAC TATTAACTGG CGAACTACTT ACTCTAGCTT CCCGGCAACA   5400
ATTAATAGAC TGGATGGAGG CGGATAAAGT TGCAGGACCA CTTCTGCGCT   5450
CGGCCCTTCC GGCTGGCTGG TTTATTGCTG ATAAATCTGG AGCCGGTGAG   5500
CGTGGGTCTC GCGGTATCAT TGCAGCACTG GGGCCAGATG GTAAGCCCTC   5550
CCGTATCGTA GTTATCTACA CGACGGGGAG TCAGGCAACT ATGGATGAAC   5600
GAAATAGACA GATCGCTGAG ATAGGTGCCT CACTGATTAA GCATTGGTAA   5650
CTGTCAGACC AAGTTACTC  ATATATACTT TAGATTGATT TAAAACTTCA   5700
TTTTTAATTT AAAAGGATCT AGGTGAAGAT CCTTTTTGAT AATCTCATGA   5750
CCAAAATCCC TTAACGTGAG TTTTCGTTCC ACTGAGCGTC AGACCCCGTA   5800
GAAAAGATCA AAGGATCTTC TTGAGATCCT TTTTTTCTGC GCGTAATCTG   5850
CTGCTTGCAA ACAAAAAAAC CACCGCTACC AGCGGTGGTT TGTTTGCCGG   5900
ATCAAGAGCT ACCAACTCTT TTTCCGAAGG TAACTGGCTT CAGCAGAGCG   5950
CAGATACCAA ATACTGTCCT TCTAGTGTAG CCGTAGTTAG GCCACCACTT   6000
CAAGAACTCT GTAGCACCGC CTACATACCT CGCTCTGCTA ATCCTGTTAC   6050
CAGTGGCTGC TGCCAGTGGC GATAAGTCGT GTCTTACCGG GTTGGACTCA   6100
AGACGATAGT TACCGGATAA GGCGCAGCGG TCGGGCTGAA CCGGGGGTTC   6150
GTGCACACAG CCCAGCTTGG AGCGAACGAC CTACACCGAA CTGAGATACC   6200
```

-continued

```
TACAGCGTGA GCATTGAGAA AGCGCCACGC TTCCCGAAGG GAGAAAGGCG 6250
GACAGGTATC CGGTAAGCGG CAGGGTCGGA ACAGGAGAGC GCACGAGGGA 6300
GCTTCCAGGG GGAAACGCCT GGTATCTTTA TAGTCCTGTC GGGTTTCGCC 6350
ACCTCTGACT TGAGCGTCGA TTTTTGTGAT GCTCGTCAGG GGGGCGGAGC 6400
CTATGGAAAA ACGCCAGCAA CGCGGCCTTT TTACGGTTCC TGGCCTTTTG 6450
CTGGCCTTTT GCTCACATGT TCTTTCCTGC GTTATCCCCT GATTCTGTGG 6500
ATAACCGTAT TACCGCCTTT GAGTGAGCTG ATACCGCTCG CCGCAGCCGA 6550
ACGACCGAGC GCAGCGAGTC AGTGAGCGAG GAAGCGGAAG AGCGCCCAAT 6600
ACGCAAACCG CCTCTCCCCG CGCGTTGGCC GATTCATTAA TCCAGCTGGC 6650
ACGACAGGTT TCCCGACTGG AAAGCGGGCA GTGAGCGCAA CGCAATTAAT 6700
GTGAGTTACC TCACTCATTA GGCACCCCAG GCTTTACACT TTATGCTTCC 6750
GGCTCGTATG TTGTGTGGAA TTGTGAGCGG ATAACAATTT CACACAGGAA 6800
ACAGCTATGA CCATGATTAC GAATTAA     6827
```

( 2 ) INFORMATION FOR SEQ ID NO:18:

( i ) SEQUENCE CHARACTERISTICS:
    ( A ) LENGTH: 348 amino acids
    ( B ) TYPE: amino acid
    ( D ) TOPOLOGY: linear ( x i ) SEQUENCE DESCRIPTION: SEQ ID NO:18:

```
Glu Lys Ser Pro Glu Gln Arg Gly Arg Phe Arg Ala Met Val Glu
 1               5                  10                  15

Leu Ala Arg Leu Asp Arg Arg Pro Gly Ser Ser Asp Arg Val
                20                  25                  30

Leu Phe Ala Arg Phe Ser Lys Thr Glu Gly Gly Ala Arg Arg Ala
                35                  40                  45

Ser Pro Asp Gln Glu Ala Glu Asp Leu Trp Leu Ser Pro Leu Thr
                50                  55                  60

Met Glu Asp Leu Val Cys Tyr Ser Phe Gln Val Ala Arg Gly Met
                65                  70                  75

Glu Phe Leu Ala Ser Arg Lys Cys Ile His Arg Asp Leu Ala Ala
                80                  85                  90

Arg Asn Ile Leu Leu Ser Glu Ser Asp Val Val Lys Ile Cys Asp
                95                  100                 105

Phe Gly Leu Ala Arg Asp Ile Tyr Lys Asp Pro Asp Tyr Val Arg
                110                 115                 120

Lys Gly Ser Ala Arg Leu Pro Leu Lys Trp Met Ala Pro Glu Ser
                125                 130                 135

Ile Phe Asp Lys Val Tyr Thr Thr Gln Ser Asp Val Trp Ser Phe
                140                 145                 150

Gly Val Leu Leu Trp Glu Ile Phe Ser Leu Gly Ala Ser Pro Tyr
                155                 160                 165

Pro Gly Val Gln Ile Asn Glu Glu Phe Cys Gln Arg Leu Arg Asp
                170                 175                 180

Gly Thr Arg Met Arg Ala Pro Glu Leu Ala Thr Pro Ala Ile Arg
                185                 190                 195

Arg Ile Met Leu Asn Cys Trp Ser Gly Asp Pro Lys Ala Arg Pro
                200                 205                 210

Ala Phe Ser Glu Leu Val Glu Ile Leu Gly Asp Leu Leu Gln Gly
                215                 220                 225
```

|  |  |  |  |  |  |  |  |  |  |  |  |  |  |
|---|---|---|---|---|---|---|---|---|---|---|---|---|---|
| Arg | Gly | Leu | Gln | Glu | Glu | Glu | Val | Cys | Met | Ala | Pro | Arg | Ser |
|  |  |  |  | 230 |  |  |  | 235 |  |  |  |  | 240 |
| Ser | Gln | Ser | Ser | Glu | Glu | Gly | Ser | Phe | Ser | Gln | Val | Ser | Thr | Met |
|  |  |  |  | 245 |  |  |  | 250 |  |  |  |  | 255 |
| Ala | Leu | His | Ile | Ala | Gln | Ala | Asp | Ala | Glu | Asp | Ser | Pro | Pro | Ser |
|  |  |  |  | 260 |  |  |  | 265 |  |  |  |  | 270 |
| Leu | Gln | Arg | His | Ser | Leu | Ala | Ala | Arg | Tyr | Tyr | Asn | Trp | Val | Ser |
|  |  |  |  | 275 |  |  |  | 280 |  |  |  |  | 285 |
| Phe | Pro | Gly | Cys | Leu | Ala | Arg | Gly | Ala | Glu | Thr | Arg | Gly | Ser | Ser |
|  |  |  |  | 290 |  |  |  | 295 |  |  |  |  | 300 |
| Arg | Met | Lys | Thr | Phe | Glu | Glu | Phe | Pro | Met | Thr | Pro | Thr | Thr | Tyr |
|  |  |  |  | 305 |  |  |  | 310 |  |  |  |  | 315 |
| Lys | Gly | Ser | Val | Asp | Asn | Gln | Thr | Asp | Ser | Gly | Met | Val | Leu | Ala |
|  |  |  |  | 320 |  |  |  | 325 |  |  |  |  | 330 |
| Ser | Glu | Glu | Cys | Glu | Gln | Ile | Glu | Ser | Arg | Tyr | Arg | Gln | Glu | Ser |
|  |  |  |  | 335 |  |  |  | 340 |  |  |  |  | 345 |
| Gly | Phe | Arg |
|  |  | 348 |

( 2 ) INFORMATION FOR SEQ ID NO:19:

( i ) SEQUENCE CHARACTERISTICS:
        ( A ) LENGTH: 7607 bases
        ( B ) TYPE: nucleic acid
        ( C ) STRANDEDNESS: single
        ( D ) TOPOLOGY: linear ( x i ) SEQUENCE DESCRIPTION: SEQ ID NO:19:

```
TTCGAGCTCG CCCGACATTG ATTATTGACT AGTTATTAAT AGTAATCAAT   50
TACGGGGTCA TTAGTTCATA GCCCATATAT GGAGTTCCGC GTTACATAAC  100
TTACGGTAAA TGGCCCGCCT GGCTGACCGC CCAACGACCC CCGCCCATTG  150
ACGTCAATAA TGACGTATGT TCCCATAGTA ACGCCAATAG GGACTTTCCA  200
TTGACGTCAA TGGGTGGAGT ATTTACGGTA AACTGCCCAC TTGCAGTAC   250
ATCAAGTGTA TCATATGCCA AGTACGCCCC CTATTGACGT CAATGACGGT  300
AAATGGCCCG CCTGGCATTA TGCCCAGTAC ATGACCTTAT GGGACTTTCC  350
TACTTGGCAG TACATCTACG TATTAGTCAT CGCTATTACC ATGGTGATGC  400
GGTTTTGGCA GTACATCAAT GGGCGTGGAT AGCGGTTTGA CTCACGGGGA  450
TTTCCAAGTC TCCACCCCAT TGACGTCAAT GGGAGTTTGT TTTGGCACCA  500
AAATCAACGG GACTTTCCAA AATGTCGTAA CAACTCCGCC CCATTGACGC  550
AAATGGGCGG TAGGCGTGTA CGGTGGGAGG TCTATATAAG CAGAGCTCGT  600
TTAGTGAACC GTCAGATCGC CTGGAGACGC CATCCACGCT GTTTTGACCT  650
CCATAGAAGA CACCGGGACC GATCCAGCCT CCGCGGCCGG GAACGGTGCA  700
TTGGAACGCG GATTCCCCGT GCCAAGAGTG ACGTAAGTAC CGCCTATAGA  750
GTCTATAGGC CCACTTGGCT TCGTTAGAAC GCGGCTACAA TTAATACATA  800
ACCTTATGTA TCATACACAT ACGATTTAGG TGACACTATA GAATAACATC  850
CACTTTGCCT TTCTCTCCAC AGGTGTCCAC TCCCAGGTCC AACTGCACCT  900
CGGTTCTATC GATTGAATTC CCCGGGGATC CTCTAGAGAT CCCTCGACCT  950
CGAGTCGACT TTTTTTTTT TTTTGTAGG CCAAAGGGTA CTTCTTTTTC   1000
TTTATTAATT ACTCAGAAGT CTAGGCCACA GCAATCTACT GTTCTCCTCT  1050
```

```
CATTTTCCTA AACTATTTTG ATACCTATTT CTCAGACTTT ATGGGCTATT 1100
AGACATTTCT CACATTTCCA TAGATAATAA CTCATCCGTT TTGCAACCTG 1150
ATTCTCAATA TTAAGAGATT AAAACTAATG TATATGACTC TCAGTTGACA 1200
CATACTGAAG TACAGAAAAA TTCCATCATT TCCTTCTGCA AAATGAAAAA 1250
GACTTCGTTT TCTCAACAGC TGCATCATTT TTTTATGCAT AGAAAAAAAT 1300
GTGCAATTAC TCCAAGTACA ATCAAGTCAT TTAACATGGC TTTACCATCA 1350
TTGTAGTTAC AGGATATTTT AAAAGAGAAA AAAAAATCTC AAAGCACAGG 1400
TCCTGCTGTG CAGCAAAGCA ATCAAATTCC TTCATAATAA CAGCCTGATG 1450
GGATTCAGCA ATCTGAGGAA TAATGAATAA CCACTCTAAT CAGTAAACAG 1500
GAAAATGCTA CAACAGTCAC TGAGTAAAAA TTGGACTATC ATCTGTTGAT 1550
TCTCTTGATC GACATTTCAA ACAATAAATG GAATGTAAG TATCTCTTAA 1600
AAAGAAAAAT AACTTGGTTT AGTGTGCTTA ATTTACCAG GCAGTGAGGA 1650
AATTATATAT CACCTTGACT GTCCTGCAGT GTTGCCCAGT CAATAAAATG 1700
CACAAATAAT CTTTTCATA ATACATGGCC AACTTTATCC TATCACTTGA 1750
ATATGTCAGG ATAAACTGAT TGTGCAGTTG GTTGATAACA TTGTATTTTG 1800
GAATGGATTA TTTGAATTTG TTTTGCTACT TTATTATTTG ATATTCTTCT 1850
CCAGTGTTCA TCTTATGAAG TTATTTGCAT CTGAATATGA AGAGTCTGTT 1900
TCAAAATAGT CTTCAAGTTT CCAACGCAGT GTCTCAAATG TAGGTCGTTC 1950
CTTAGGCTCT GCATTCCAGC ACTCCAACAT GATGTTGTAA AATTGCTGTG 2000
GACAGTTGGA TGGTTGCGGA AGTCTATAGT TTTGAGCCAA CATCTGGATT 2050
ACCTGGGCAC CTGTCATACC ACTGTAAGGC ATTTTGCCAT AAGTAATGAT 2100
TTCATAAAGA AGGATTCCAA ATGACCATAC ATCGGACTTA ATGCTGAATT 2150
TATTACTACG AATGGCTTCG GGCGCAGTCC ACTTCACCGG CAGCTTTATT 2200
TCGTGTCTAG ATTCATAGAT GTCTTCATTA TCTACCTTAA AAACTCTGGC 2250
AAGTCCAAAA TCTGCTACTT TGTAGATATT ATGTTCACCA ACGAGGACAT 2300
TTCTGGCAGC CAGATCTCTG TGAATGTAGT TCCGAGACTC CAGATAGGCC 2350
ATTCCAGAGG CAACCTGTGC CGCCATGTCT ACCTGTTGAG TCAGATGGAT 2400
TTTTGATCCA GTGTCATTTT GGAGATATTC TTGCAGACTT CCATGTCTCA 2450
TCAACTCTGT AATAATATAA ATTGGATCTT CTAAAGTGCA AACAGCATAA 2500
AGCTGGATAA GCTTTGGATG TCTTAGGTTC TTCATTATCT GTGCCTCCCT 2550
CAGGAAGTCA TTTGGATCCA TTGAACCTGG TTTTAATGTT TTCACTGCTA 2600
CTGGAGTGGT ATTGTTCCAC AGACCTTCCC ATACTTCGCC AAACTGACCA 2650
GATCCCAATC GCTTCAGAAG CTGTATGGAG TTGCGGTCTA TCTCCCATTG 2700
GTCCACGGTT TTATACGACA AATCAAATGG AGCTGGGACC TGGATCTTTA 2750
AGCATGGTTT CCCCAGCTTG ACACACAGGC CGTCACTTGT CTTGGTGTAG 2800
TGGCTCACAA ATTCGTTCAG TGTTGAAAAG ATTCTTCTTC GCGTGAGAAA 2850
AAATCCCCCT TCATCCAGTC TTTTAATTCT GTAGTGTTTT ACAACTGCTC 2900
CATCTAAAAC TGAAAGAGAG AATTCTCCTT TTTGGCTTTC ACTTTCTCTG 2950
ATTAGAAAGG AACCGGTCTT GTTTTCTGAA TATAATAGTT GTTTCTCTGC 3000
ATCTGATCTT CCGATTGCTC CAAAGAACCA CGGCTCTGCC TGTAGGCTTC 3050
```

```
TGTCCTCAGC CACGTAGTTA GAAGGAATAT AGCCTTGTAG TTGCTGACTG 3100
GAGCCATCTC GTCTTTCTC  CAAGTGTCTG GCAAACCACC AGCCCTCATG 3150
CAAAGTGTCC AGAACTTGAA GTTTGTCACC TGCTCGGAAG CTCAAGTCCT 3200
CAGCAGTCCG AGCCTGGTAA TCAAACAAAG CCACAAGTA  GTGGCCATGC 3250
CTCTGTGACT GGGGAGAGCA AAGGGCCCT  GGATTTTCAA TCACGGTTGA 3300
CTTGTCTGCC TCCGTGGACA AACAGGGGAG ATAGGGTTCT AGGTACTCCC 3350
AGAGCCTCTG ACAGATGTTG CTCATTGTGC CTGGTGGGG  AGAAGAGGAG 3400
CAGGGCTTCT CCCTCTCCCC TTAGTCTCTG CGATCCACCT TATCTTCCTT 3450
CACCAGGCAA CTTTGAAGTC AGCACCAACT CACCATACTT CGGAGAGTAT 3500
GCAAAGTCCC GTTTCAGATC AGTCCAGCAG CTGGGTTGCA GCAAGTCCTA 3550
CCTGGAGAGA CTTACCGGCT TGCTTTCTGT GGCTGGAGGT GCTACCCCGA 3600
GGCAAAACTG AGCAGGAGCT GGGCAGCTGC TCACTAGGAA GGTGTCTTTT 3650
CTTCTTATCT GCTTAAGAAT CCCACAACAA AAATAAAATA AAATTAAAAG 3700
GGCTTTATTT AGACAAATAT CTGAGAACAG AATGGTGCCA TCTTGCCTTT 3750
TGTCCCAATA AAAGTTAGC  AAGAGGAAGC TACTAACCCC TGGTAAAACC 3800
TCCACGTCTT GCTTTCGCCA GGGTCGACTC GAGGGATCTT CCATACCTAC 3850
CAGTTCTGCG CCTGCAGGTC GCGGCCGCGA CTCTAGAGTC GACCTGCAGA 3900
AGCTTGGCCG CCATGGCCCA ACTTGTTTAT TGCAGCTTAT AATGGTTACA 3950
AATAAAGCAA TAGCATCACA AATTTCACAA ATAAAGCATT TTTTCACTG  4000
CATTCTAGTT GTGGTTTGTC CAAACTCATC AATGTATCTT ATCATGTCTG 4050
GATCGGGAAT TAATTCGGCG CAGCACCATG GCCTGAAATA ACCTCTGAAA 4100
GAGGAACTTG GTTAGGTACC TTCTGAGGCG GAAAGAACCA GCTGTGGAAT 4150
GTGTGTCAGT TAGGGTGTGG AAAGTCCCCA GGCTCCCAG  CAGGCAGAAG 4200
TATGCAAAGC ATGCATCTCA ATTAGTCAGC AACCAGGTGT GGAAAGTCCC 4250
CAGGCTCCCC AGCAGGCAGA AGTATGCAAA GCATGCATCT CAATTAGTCA 4300
GCAACCATAG TCCCGCCCCT AACTCCGCCC ATCCCGCCCC TAACTCCGCC 4350
CAGTTCCGCC CATTCTCCGC CCCATGGCTG ACTAATTTTT TTATTTATG  4400
CAGAGGCCGA GGCCGCCTCG GCCTCTGAGC TATTCCAGAA GTAGTGAGGA 4450
GGCTTTTTTG GAGGCCTAGG CTTTTGCAAA AAGCTGTTAA CAGCTTGGCA 4500
CTGGCCGTCG TTTTACAACG TCGTGACTGG GAAAACCCTG GCGTTACCCA 4550
ACTTAATCGC CTTGCAGCAC ATCCCCCTTT CGCCAGCTGG CGTAATAGCG 4600
AAGAGGCCCG CACCGATCGC CCTTCCCAAC AGTTGCGCAG CCTGAATGGC 4650
GAATGGCGCC TGATGCGGTA TTTTCTCCTT ACGCATCTGT GCGGTATTTC 4700
ACACCGCATA CGTCAAAGCA ACCATAGTAC GCGCCCTGTA GCGGCGCATT 4750
AAGCGCGGCG GGTGTGGTGG TTACGCGCAG CGTGACCGCT ACACTTGCCA 4800
GCGCCCTAGC GCCCGCTCCT TTCGCTTTCT TCCCTTCCTT TCTCGCCACG 4850
TTCGCCGGCT TTCCCCGTCA AGCTCTAAAT CGGGGCTCC  CTTTAGGGTT 4900
CCGATTTAGT GCTTTACGGC ACCTCGACCC CAAAAAACTT GATTTGGGTG 4950
ATGGTTCACG TAGTGGGCCA TCGCCCTGAT AGACGGTTTT TCGCCCTTTG 5000
ACGTTGGAGT CCACGTTCTT TAATAGTGGA CTCTTGTTCC AAACTGGAAC 5050
```

```
AACACTCAAC  CCTATCTCGG  GCTATTCTTT  TGATTTATAA  GGGATTTTGC  5100
CGATTTCGGC  CTATTGGTTA  AAAAATGAGC  TGATTTAACA  AAAATTTAAC  5150
GCGAATTTTA  ACAAATATT   AACGTTTACA  ATTTTATGGT  GCACTCTCAG  5200
TACAATCTGC  TCTGATGCCG  CATAGTTAAG  CCAGCCCCGA  CACCCGCCAA  5250
CACCCGCTGA  CGCGCCCTGA  CGGGCTTGTC  TGCTCCCGGC  ATCCGCTTAC  5300
AGACAAGCTG  TGACCGTCTC  CGGGAGCTGC  ATGTGTCAGA  GGTTTTCACC  5350
GTCATCACCG  AAACGCGCGA  GACGAAAGGG  CCTCGTGATA  CGCCTATTTT  5400
TATAGGTTAA  TGTCATGATA  ATAATGGTTT  CTTAGACGTC  AGGTGGCACT  5450
TTTCGGGGAA  ATGTGCGCGG  AACCCCTATT  TGTTTATTTT  CTAAATACA   5500
TTCAAATATG  TATCCGCTCA  TGAGACAATA  ACCCTGATAA  ATGCTTCAAT  5550
AATATTGAAA  AAGGAAGAGT  ATGAGTATTC  AACATTTCCG  TGTCGCCCTT  5600
ATTCCCTTTT  TTGCGGCATT  TTGCCTTCCT  GTTTTTGCTC  ACCCAGAAAC  5650
GCTGGTGAAA  GTAAAAGATG  CTGAAGATCA  GTTGGGTGCA  CGAGTGGGTT  5700
ACATCGAACT  GGATCTCAAC  AGCGGTAAGA  TCCTTGAGAG  TTTTCGCCCC  5750
GAAGAACGTT  TTCCAATGAT  GAGCACTTTT  AAAGTTCTGC  TATGTGGCGC  5800
GGTATTATCC  CGTATTGACG  CCGGGCAAGA  GCAACTCGGT  CGCCGCATAC  5850
ACTATTCTCA  GAATGACTTG  GTTGAGTACT  CACCAGTCAC  AGAAAAGCAT  5900
CTTACGGATG  GCATGACAGT  AAGAGAATTA  TGCAGTGCTG  CCATAACCAT  5950
GAGTGATAAC  ACTGCGGCCA  ACTTACTTCT  GACAACGATC  GGAGGACCGA  6000
AGGAGCTAAC  CGCTTTTTTG  CACAACATGG  GGGATCATGT  AACTCGCCTT  6050
GATCGTTGGG  AACCGGAGCT  GAATGAAGCC  ATACCAAACG  ACGAGCGTGA  6100
CACCACGATG  CCTGTAGCAA  TGGCAACAAC  GTTGCGCAAA  CTATTAACTG  6150
GCGAACTACT  TACTCTAGCT  TCCCGGCAAC  AATTAATAGA  CTGGATGGAG  6200
GCGGATAAAG  TTGCAGGACC  ACTTCTGCGC  TCGGCCCTTC  CGGCTGGCTG  6250
GTTTATTGCT  GATAAATCTG  GAGCCGGTGA  GCGTGGGTCT  CGCGGTATCA  6300
TTGCAGCACT  GGGGCCAGAT  GGTAAGCCCT  CCCGTATCGT  AGTTATCTAC  6350
ACGACGGGGA  GTCAGGCAAC  TATGGATGAA  CGAAATAGAC  AGATCGCTGA  6400
GATAGGTGCC  TCACTGATTA  AGCATTGGTA  ACTGTCAGAC  CAAGTTTACT  6450
CATATATACT  TTAGATTGAT  TTAAAACTTC  ATTTTTAATT  TAAAAGGATC  6500
TAGGTGAAGA  TCCTTTTTGA  TAATCTCATG  ACCAAAATCC  CTTAACGTGA  6550
GTTTTCGTTC  CACTGAGCGT  CAGACCCCGT  AGAAAAGATC  AAAGGATCTT  6600
CTTGAGATCC  TTTTTTTCTG  CGCGTAATCT  GCTGCTTGCA  ACAAAAAAA   6650
CCACCGCTAC  CAGCGGTGGT  TTGTTTGCCG  GATCAAGAGC  TACCAACTCT  6700
TTTTCCGAAG  GTAACTGGCT  TCAGCAGAGC  GCAGATACCA  AATACTGTTC  6750
TTCTAGTGTA  GCCGTAGTTA  GGCCACCACT  TCAAGAACTC  TGTAGCACCG  6800
CCTACATACC  TCGCTCTGCT  AATCCTGTTA  CCAGTGGCTG  CTGCCAGTGG  6850
CGATAAGTCG  TGTCTTACCG  GGTTGGACTC  AAGACGATAG  TTACCGGATA  6900
AGGCGCAGCG  GTCGGGCTGA  ACGGGGGGTT  CGTGCACACA  GCCCAGCTTG  6950
GAGCGAACGA  CCTACACCGA  ACTGAGATAC  CTACAGCGTG  AGCTATGAGA  7000
AAGCGCCACG  CTTCCCGAAG  GGAGAAAGGC  GGACAGGTAT  CCGGTAAGCG  7050
```

```
GCAGGGTCGG AACAGGAGAG CGCACGAGGG AGCTTCCAGG GGGAAACGCC    7100
TGGTATCTTT ATAGTCCTGT CGGGTTTCGC CACCTCTGAC TTGAGCGTCG    7150
ATTTTTGTGA TGCTCGTCAG GGGGCGGAG CCTATGGAAA AACGCCAGCA     7200
ACGCGGCCTT TTTACGGTTC CTGGCCTTTT GCTGGCCTTT TGCTCACATG    7250
TTCTTTCCTG CGTTATCCCC TGATTCTGTG GATAACCGTA TTACCGCCTT    7300
TGAGTGAGCT GATACCGCTC GCCGCAGCCG AACGACCGAG CGCAGCGAGT    7350
CAGTGAGCGA GGAAGCGGAA GAGCGCCCAA TACGCAAACC GCCTCTCCCC    7400
GCGCGTTGGC CGATTCATTA ATGCAGCTGG CACGACAGGT TTCCCGACTG    7450
GAAAGCGGGC AGTGAGCGCA ACGCAATTAA TGTGAGTTAG CTCACTCATT    7500
AGGCACCCCA GGCTTTACAC TTTATGCTTC CGGCTCGTAT GTTGTGTGGA    7550
ATTGTGAGCG GATAACAATT TCACACAGGA AACAGCTATG ACATGATTAC    7600
GAATTAA    7607
```

( 2 ) INFORMATION FOR SEQ ID NO:20:

( i ) SEQUENCE CHARACTERISTICS:
        ( A ) LENGTH: 505 amino acids
        ( B ) TYPE: amino acid
        ( D ) TOPOLOGY: linear ( x i ) SEQUENCE DESCRIPTION: SEQ ID NO:20:

```
Met Ser Asn Ile Cys Gln Arg Leu Trp Glu Tyr Leu Glu Pro Tyr
 1               5                  10                  15

Leu Pro Cys Leu Ser Thr Glu Ala Asp Lys Ser Thr Val Ile Glu
                20                  25                  30

Asn Pro Gly Ala Leu Cys Ser Pro Gln Ser Gln Arg His Gly His
                35                  40                  45

Tyr Phe Val Ala Leu Phe Asp Tyr Gln Ala Arg Thr Ala Glu Asp
                50                  55                  60

Leu Ser Phe Arg Ala Gly Asp Lys Leu Gln Val Leu Asp Thr Leu
                65                  70                  75

His Glu Gly Trp Trp Phe Ala Arg His Leu Glu Lys Arg Arg Asp
                80                  85                  90

Gly Ser Ser Gln Gln Leu Gln Gly Tyr Ile Pro Ser Asn Tyr Val
                95                  100                 105

Ala Glu Asp Arg Ser Leu Gln Ala Glu Pro Trp Phe Phe Gly Ala
                110                 115                 120

Ile Gly Arg Ser Asp Ala Glu Lys Gln Leu Leu Tyr Ser Glu Asn
                125                 130                 135

Lys Thr Gly Ser Phe Leu Ile Arg Glu Ser Glu Ser Gln Lys Gly
                140                 145                 150

Glu Phe Ser Leu Ser Val Leu Asp Gly Ala Val Val Lys His Tyr
                155                 160                 165

Arg Ile Lys Arg Leu Asp Glu Gly Gly Phe Phe Leu Thr Arg Arg
                170                 175                 180

Arg Ile Phe Ser Thr Leu Asn Glu Phe Val Ser His Tyr Thr Lys
                185                 190                 195

Thr Ser Asp Gly Leu Cys Val Lys Leu Gly Lys Pro Cys Leu Lys
                200                 205                 210

Ile Gln Val Pro Ala Pro Phe Asp Leu Ser Tyr Lys Thr Val Asp
                215                 220                 225
```

| | | | | | | | | | | | | | |
|---|---|---|---|---|---|---|---|---|---|---|---|---|---|
|Gln|Trp|Glu|Ile|Asp<br>230|Arg|Asn|Ser|Ile|Gln<br>235|Leu|Leu|Lys|Arg|Leu<br>240|
|Gly|Ser|Gly|Gln|Phe<br>245|Gly|Glu|Val|Trp|Glu<br>250|Gly|Leu|Trp|Asn|Asn<br>255|
|Thr|Thr|Pro|Val|Ala<br>260|Val|Lys|Thr|Leu|Lys<br>265|Pro|Gly|Ser|Met|Asp<br>270|
|Pro|Asn|Asp|Phe|Leu<br>275|Arg|Glu|Ala|Gln|Ile<br>280|Met|Lys|Asn|Leu|Arg<br>285|
|His|Pro|Lys|Leu|Ile<br>290|Gln|Leu|Tyr|Ala|Val<br>295|Cys|Thr|Leu|Glu|Asp<br>300|
|Pro|Ile|Tyr|Ile|Ile<br>305|Thr|Glu|Leu|Met|Arg<br>310|His|Gly|Ser|Leu|Gln<br>315|
|Glu|Tyr|Leu|Gln|Asn<br>320|Asp|Thr|Gly|Ser|Lys<br>325|Ile|His|Leu|Thr|Gln<br>330|
|Gln|Val|Asp|Met|Ala<br>335|Ala|Gln|Val|Ala|Ser<br>340|Gly|Met|Ala|Tyr|Leu<br>345|
|Glu|Ser|Arg|Asn|Tyr<br>350|Ile|His|Arg|Asp|Leu<br>355|Ala|Ala|Arg|Asn|Val<br>360|
|Leu|Val|Gly|Glu|His<br>365|Asn|Ile|Tyr|Lys|Val<br>370|Ala|Asp|Phe|Gly|Leu<br>375|
|Ala|Arg|Val|Phe|Lys<br>380|Val|Asp|Asn|Glu|Asp<br>385|Ile|Tyr|Glu|Ser|Arg<br>390|
|His|Glu|Ile|Lys|Leu<br>395|Pro|Val|Lys|Trp|Thr<br>400|Ala|Pro|Glu|Ala|Ile<br>405|
|Arg|Ser|Asn|Lys|Phe<br>410|Ser|Ile|Lys|Ser|Asp<br>415|Val|Trp|Ser|Phe|Gly<br>420|
|Ile|Leu|Leu|Tyr|Glu<br>425|Ile|Ile|Thr|Tyr|Gly<br>430|Lys|Met|Pro|Tyr|Ser<br>435|
|Gly|Met|Thr|Gly|Ala<br>440|Gln|Val|Ile|Gln|Met<br>445|Leu|Ala|Gln|Asn|Tyr<br>450|
|Arg|Leu|Pro|Gln|Pro<br>455|Ser|Asn|Cys|Pro|Gln<br>460|Gln|Phe|Tyr|Asn|Ile<br>465|
|Met|Leu|Glu|Cys|Trp<br>470|Asn|Ala|Glu|Pro|Lys<br>475|Glu|Arg|Pro|Thr|Phe<br>480|
|Glu|Thr|Leu|Arg|Trp<br>485|Lys|Leu|Glu|Asp|Tyr<br>490|Phe|Glu|Thr|Asp|Ser<br>495|
|Ser|Tyr|Ser|Asp|Ala<br>500|Asn|Asn|Phe|Ile|Arg<br>505|

( 2 ) INFORMATION FOR SEQ ID NO:21:

( i ) SEQUENCE CHARACTERISTICS:
        ( A ) LENGTH: 404 bases
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
GCGGCCGCAG AGAAAGCAGA GGATGGGGCT TAGCAGCTGG CAGAGCCAGG    50

AGCGGGGAGG TAGCAGAAAG ACCACAAGTA CAAAGAAGTC CTGAAACTTT   100

GGTTTTGCTG CTGCAGCCCA TTGAGAGTGA CGACATGGAG CACAAGACCC   150

TGAAGATCAC CGACTTTGGC CTGGCCCGAG AGTGGCACAA AACCACACAA   200

ATGAGTGCCG CNGGCACCTA CNCCTGGATG GCTCCTGAGG TTATCAAGGC   250

CTCCACCTTC TCTAAGGGCA GTGACGTCTG GAGTTTTGGG GTGCTGCTGT   300
```

```
GGGAACTGCT GACCGGGGAG NTGCCATACC GTGGCATTGA CTGCCTTGCT    350

GTGGCCTATG GCGTAGCTGT TAACAAGCTC ACACTGCCAT CCATCCACCT    400

GGCC    404
```

( 2 ) INFORMATION FOR SEQ ID NO:22:

( i ) SEQUENCE CHARACTERISTICS:
( A ) LENGTH: 3120 bases
( B ) TYPE: nucleic acid
( C ) STRANDEDNESS: single
( D ) TOPOLOGY: linear ( x i ) SEQUENCE DESCRIPTION: SEQ ID NO:22:

```
ATGAGAGCGT TGGCGCGCGA CGGCGGCCAG CTGCCGCTGC TCGTTGTTTT    50

TTCTGCAATG ATATTTGGGA CTATTACAAA TCAAGATCTG CCTGTGATCA    100

AGTGTGTTTT AATCAATCAT AAGAACAATG ATTCATCAGT GGGGAAGTCA    150

TCATCATATC CCATGGTATC AGAATCCCCG GAAGACCTCG GGTGTGCGTT    200

GAGACCCCAG AGCTCAGGGA CAGTGTACGA AGCTGCCGCT GTGGAAGTGG    250

ATGTATCTGC TTCCATCACA CTGCAAGTGC TGGTCGATGC CCCAGGGAAC    300

ATTTCCTGTC TCTGGGTCTT TAAGCACAGC TCCCTGAATT GCCAGCCACA    350

TTTTGATTTA CAAAACAGAG GAGTTGTTTC CATGGTCATT TTGAAAATGA    400

CAGAAACCCA AGCTGGAGAA TACCTACTTT TTATTCAGAG TGAAGCTACC    450

AATTACACAA TATTGTTTAC AGTGAGTATA AGAAATACCC TGCTTTACAC    500

ATTAAGAAGA CCTTACTTTA GAAAAATGGA AAACCAGGAC GCCCTGGTCT    550

GCATATCTGA GAGCGTTCCA GAGCGGATCC TGGAATGGGT GCTTTGCGAT    600

TCACAGGGGG AAAGCTGTAA AGAAGAAAGT CCAGCTGTTG TTAAAAAGGA    650

GGAAAAAGTG CTTCATGAAT TATTTGGGAC GGACATAAGG TGCTGTGCCA    700

GAAATGAACT GGGCAGGGAA TGCACCAGGC TGTTCACAAT AGATCTAAAT    750

CAAACTCCTC AGACCACATT GCCACAATTA TTTCTTAAAG TAGGGGAACC    800

CTTATGGATA AGGTGCAAAG CTGTTCATGT GAACCATGGA TTCGGGCTCA    850

CCTGGGAATT AGAAAACAAA GCACTCGAGG AGGGCAACTA CTTTGAGATG    900

AGTACCTATT CAACAAACAG AACTATGATA CGGATTCTGT TTGCTTTTGT    950

ATCATCAGTG GCAAGAAACG ACACCGGATA CTACACTTGT TCCTCTTCAA    1000

AGCATCCCAG TCAATCAGCT TTGGTTACCA TCGTAGAAAA GGGATTTATA    1050

AATGCTACCA ATTCAAGTGA AGATTATGAA ATTGACCAAT ATGAAGAGTT    1100

TTGTTTTTCT GTCAGGTTTA AAGCCTACCC ACAAATCAGA TGTACGTGGA    1150

CCTTCTCTCG AAAATCATTT CCTTGTGAGC AAAAGGGTCT TGATAACGGA    1200

TACAGCATAT CCAAGTTTTG CAATCATAAG CACCAGCCAG AGAATATAT    1250

ATTCCATGCA GAAAATGATG ATGCCCAATT TACCAAAATG TTCACGCTGT    1300

ATATAAGAAG GAAACCTCAA GTCCTCGCAG AAGCTTCGGC AAGTCAGGCG    1350

TCCTGTTTCT CGGATGGATA CCCATTACCA TCTTGGACCT GGAAGAAGTG    1400

TTCAGACAAG TCTCCCAACT GCACAGAAGA GATCACAGAA GGAGTCTGGA    1450

ATAGAAAGGC TAACAGAAAA GTGTTTGGAC AGTGGGTGTC GAGCAGTACT    1500

CTAAACATGA GTGAAGCCAT AAAAGGGTTC CTGGTCAAGT GCTGTGCATA    1550

CAATTCCCTT GGCACATCTT GTGAGACGAT CCTTTTAAAC TCTCCAGGCC    1600
```

```
CCTTCCCTTT  CATCCAAGAC  AACATCTCAT  TCTATGCAAC  AATTGGTGTT  1650
TGTCTCCTCT  TCATTGTCGT  TTTAACCCTG  CTAATTTGTC  ACAAGTACAA  1700
AAAGCAATTT  AGGTATGAAA  GCCAGCTACA  GATGGTACAG  GTGACCGGAT  1750
CCTCAGATTA  TGAGTACTTC  TACGTTGATT  TCAGAGAATA  TGAATATGAT  1800
GTCAAATGGG  AGTTTCCAAG  AGAAAATTTA  GAGTTTGGGA  AGGTACTAGG  1850
ATCAGGTGCT  TTTGGAAAAG  TGATGAACGC  AACAGCTTAT  GGAATTAGCA  1900
AAACAGGAGT  CTCAATCCAG  GTTACCGTCA  AAATGCTGAA  AGAAAAAGCA  1950
GACAGCTCTG  AAAGAGAGGC  ACTCATGTCA  GAACTCAAGA  TGATGACCCA  2000
GCTGGGAAGC  CACGAGAATA  TTGTGAACCT  GCTGGGGGCG  TGCACACTGT  2050
CAGGACCAAT  TTACTTGATT  TTTGAATACT  GTTGCTATGG  TGATCTTCTC  2100
AACTATCTAA  GAAGTAAAAG  AGAAAAATTT  CACAGGACTT  GGACAGAGAT  2150
TTTCAAGGAA  CACAATTTCA  GTTTTTACCC  CACTTTCCAA  TCACATCCAA  2200
ATTCCAGCAT  GCCTGGTTCA  AGAGAAGTTC  AGATACACCC  GGACTCGGAT  2250
CAAATCTCAG  GGCTTCATGG  GAATTCATTT  CACTCTGAAG  ATGAAATTGA  2300
ATATGAAAAC  CAAAAAGGC   TGGAAGAAGA  GGAGGACTTG  AATGTGCTTA  2350
CATTTGAAGA  TCTTCTTTGC  TTTGCATATC  AAGTTGCCAA  AGGAATGGAA  2400
TTTCTGGAAT  TTAAGTCGTG  TGTTCACAGA  GACCTGGCCG  CCAGGAACGT  2450
GCTTGTCACC  CACGGGAAAG  TGGTGAAGAT  ATGTGACTTT  GGATTGGCTC  2500
GAGATATCAT  GAGTGATTCC  AACTATGTTG  TCAGGGGCAA  TGCCCGTCTG  2550
CCTGTAAAAT  GGATGGCCCC  CGAAAGCCTG  TTTGAAGGCA  TCTACACCAT  2600
TAAGAGTGAT  GTCTGGTCAT  ATGGAATATT  ACTGTGGGAA  ATCTTCTCAC  2650
TTGGTGTGAA  TCCTTACCCT  GGCATTCCGG  TTGATGCTAA  CTTCTACAAA  2700
CTGATTCAAA  ATGGATTTAA  AATGGATCAG  CCATTTTATG  CTACAGAAGA  2750
AATATACATT  ATAATGCAAT  CCTGCTGGGC  TTTTGACTCA  AGGAAACGGC  2800
CATCCTTCCC  TAATTTGACT  TCGTTTTTAG  GATGTCAGCT  GGCAGATGCA  2850
GAAGAAGCGA  TGTATCAGAA  TGTGGATGGC  CGTGTTTCGG  AATGTCCTCA  2900
CACCTACCAA  AACAGGCGAC  CTTTCAGCAG  AGAGATGGAT  TTGGGGCTAC  2950
TCTCTCCGCA  GGCTCAGGTC  GAAGATTCGT  AGAGGAACAA  TTTAGTTTTA  3000
AGGACTTCAT  CCCTCCACCT  ATCCCTAACA  GGCTGTAGAT  TACCAAAACA  3050
AGGTTAATTT  CATCACTAAA  AGAAAATCTA  TTATCAACTG  CTGCTTCACC  3100
AGACTTTTCT  CTAGAGAGCG  3120
```

( 2 ) INFORMATION FOR SEQ ID NO:23:

( i ) SEQUENCE CHARACTERISTICS:
        ( A ) LENGTH: 3969 bases
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
TCGGCGTCCA  CCCGCCCAGG  GAGAGTCAGA  CCTGGGGGGG  CGAGGGCCCC  50
CCAAACTCAG  TTCGGATCCT  ACCCGAGTGA  GGCGGCGCCA  TGGAGCTCCG  100
GGTGCTGCTC  TGCTGGGCTT  CGTTGGCCGC  AGCTTTGGAA  GAGACCCTGC  150
```

```
TGAACACAAA ATTGGAAACT GCTGATCTGA AGTGGGTGAC ATTCCCTCAG  200
GTGGACGGGC AGTGGGAGGA ACTGAGCGGC CTGGATGAGG AACAGCACAG  250
CGTGCGCACC TACGAAGTGT GTGACGTGCA GCGTGCCCCG GGCCAGGCCC  300
ACTGGCTTCG CACAGGTTGG GTCCCACGGC GGGGCGCCGT CCACGTGTAC  350
GCCACGCTGC GCTTCACCAT GCTCGAGTGC CTGTCCCTGC CTCGGGCTGG  400
GCGCTCCTGC AAGGAGACCT TCACCGTCTT CTACTATGAG AGCGATGCGG  450
ACACGGCCAC GGCCCTCACG CCAGCCTGGA TGGAGAACCC CTACATCAAG  500
GTGGACACGG TGGCCGCGGA GCATCTCACC CGGAAGCGCC TGGGGCCGA   550
GGCCACCGGG AAGGTGAATG TCAAGACGCT GCGTCTGGGA CCGCTCAGCA  600
AGGCTGGCTT CTACCTGGCC TTCCAGGACC AGGGTGCCTG CATGGCCCTG  650
CTATCCCTGC ACCTCTTCTA CAAAAAGTGC GCCCAGCTGA CTGTGAACCT  700
GACTCGATTC CCGGAGACTG TGCCTCGGGA GCTGGTTGTG CCCGTGGCCG  750
GTAGCTGCGT GGTGGATGCC GTCCCCGCCC CTGGCCCCAG CCCCAGCCTC  800
TACTGCCGTG AGGATGGCCA GTGGGCCGAA CAGCCGGTCA CGGGCTGCAG  850
CTGTGCTCCG GGGTTCGAGG CAGCTGAGGG GAACACCAAG TGCCGAGCCT  900
GTGCCCAGGG CACCTTCAAG CCCCTGTCAG GAGAAGGGTC CTGCCAGCCA  950
TGCCCAGCCA ATAGCCACTC TAACACCATT GGATCAGCCG TCTGCCAGTG  1000
CCGCGTCGGG TACTTCCGGG CACGCACAGA CCCCCGGGGT GCACCCTGCA  1050
CCACCCCTCC TTCGGCTCCG CGGAGCGTGG TTTCCCGCCT GAACGGCTCC  1100
TCCCTGCACC TGGAATGGAG TGCCCCCCTG GAGTCTGGTG GCCGAGAGGA  1150
CCTCACCTAC GCCCTCCGCT GCCGGGAGTG CCGACCCGGA GGCTCCTGTG  1200
CGCCCTGCGG GGAGACCTG ACTTTGACCC CGGCCCCCG GACCTGGTG     1250
GAGCCCTGGG TGGTGGTTCG AGGGCTACGT CCTGACTTCA CCTATACCTT  1300
TGAGGTCACT GCATTGAACG GGTATCCTC CTTAGCCACG GGGCCCGTCC   1350
CATTTGAGCC TGTCAATGTC ACCACTGACC GAGAGGTACC TCCTGCAGTG  1400
TCTGACATCC GGGTGACGCG GTCCTCACCC AGCAGCTTGA GCCTGGCCTG  1450
GGCTGTTCCC CGGGCACCCA GTGGGGCTGT GCTGGACTAC GAGGTCAAAT  1500
ACCATGAGAA GGGCGCCGAG GGTCCCAGCA GCGTGCGGTT CCTGAAGACG  1550
TCAGAAAACC GGGCAGAGCT GCGGGGGCTG AAGCGGGGAG CCAGCTACCT  1600
GGTGCAGGTA CGGGCGCGCT CTGAGGCCGG CTACGGGCCC TTCGGCCAGG  1650
AACATCACAG CCAGACCCAA CTGGATGAGA GCGAGGGCTG GCGGGAGCAG  1700
CTGGCCCTGA TTGCGGGCAC GGCAGTCGTG GGTGTGGTCC TGGTCCTGGT  1750
GGTCATTGTG GTCGCAGTTC TCTGCCTCAG GAAGCAGAGC AATGGGAGAG  1800
AAGCAGAATA TTCGGACAAA CACGGACAGT ATCTCATCGG ACATGGTACT  1850
AAGGTCTACA TCGACCCCTT CACTTATGAA GACCCTAATG AGGCTGTGAG  1900
GGAATTTGCA AAAGAGATCG ATGTCTCCTA CGTCAAGATT GAAGAGGTGA  1950
TTGGTGCAGG TGAGTTTGGC GAGGTGTGCC GGGGCGGCT CAAGGCCCCA   2000
GGGAAGAAGG AGAGCTGTGT GGCAATCAAG ACCCTGAAGG GTGGCTACAC  2050
GGAGCGGCAG CGGCGTGAGT TTCTGAGCGA GGCCTCCATC ATGGGCCAGT  2100
TCGAGCACCC CAATATCATC CGCCTGGAGG GCGTGGTCAC CAACAGCATG  2150
```

| | | | | |
|---|---|---|---|---|
| CCCGTCATGA | TTCTCACAGA | GTTCATGGAG | AACGGCGCCC | TGGACTCCTT 2200 |
| CCTGCGGCTA | AACGACGGAC | AGTTCACAGT | CATCCAGCTC | GTGGGCATGC 2250 |
| TGCGGGGCAT | CGCCTCGGGC | ATGCGGTACC | TTGCCGAGAT | GAGCTACGTC 2300 |
| CACCGAGACC | TGGCTGCTCG | CAACATCCTA | GTCAACAGCA | ACCTCGTCTG 2350 |
| CAAAGTGTCT | GACTTTGGCC | TTTCCCGATT | CCTGGAGGAG | AACTCTTCCG 2400 |
| ATCCCACCTA | CACGAGCTCC | CTGGGAGGAA | AGATTCCCAT | CCGATGGACT 2450 |
| GCCCCGGAGG | CCATTGCCTT | CCGGAAGTTC | ACTTCCGCCA | GTGATGCCTG 2500 |
| GAGTTACGGG | ATTGTGATGT | GGGAGGTGAT | GTCATTTGGG | GAGAGGCCGT 2550 |
| ACTGGGACAT | GAGCAATCAG | GACGTGATCA | ATGCCATTGA | ACAGGACTAC 2600 |
| CGGCTGCCCC | CGCCCCCAGA | CTGTCCCACC | TCCTCCACC | AGCTCATGCT 2650 |
| GGACTGTTGG | CAGAAAGACC | GGAATGCCCG | GCCCCGCTTC | CCCCAGGTGG 2700 |
| TCAGCGCCCT | GGACAAGATG | ATCCGGAACC | CCGCCAGCCT | CAAAATCGTG 2750 |
| GCCCGGGAGA | ATGGCGGGGC | CTCACACCCT | CTCCTGGACC | AGCGGCAGCC 2800 |
| TCACTACTCA | GCTTTTGGCT | CTGTGGGCGA | GTGGCTTCGG | GCCATCAAAA 2850 |
| TGGGAAGATA | CGAAGAAAGT | TTCGCAGCCG | CTGGCTTTGG | CTCCTTCGAG 2900 |
| CTGGTCAGCC | AGATCTCTGC | TGAGGACCTG | CTCCGAATCG | GAGTCACTCT 2950 |
| GGCGGGACAC | CAGAAGAAAA | TCTTGGCCAG | TGTCCAGCAC | ATGAAGTCCC 3000 |
| AGGCCAAGCC | GGGAACCCCG | GGTGGGACAG | GAGGACCGGC | CCCGCAGTAC 3050 |
| TGACCTGCAG | GAACTCCCCA | CCCCAGGGAC | ACCGCCTCCC | CATTTTCCGG 3100 |
| GGCAGAGTGG | GGACTCACAG | AGGCCCCCAG | CCCTGTGCCC | CGCTGGATTG 3150 |
| CACTTTGAGC | CCGTGGGGTG | AGGAGTTGGC | AATTTGGAGA | GACAGGATTT 3200 |
| GGGGGTTCTG | CCATAATAGG | AGGGGAAAAT | CACCCCCCAG | CCACCTCGGG 3250 |
| GAACTCCAGA | CCAAGGGTGA | GGGCGCCTTT | CCCTCAGGAC | TGGGTGTGAC 3300 |
| CAGAGGAAAA | GGAAGTGCCC | AACATCTCCC | AGCCTCCCCA | GGTGCCCCC 3350 |
| TCACCTTGAT | GGGTGCGTTC | CCGCAGACCA | AAGAGAGTGT | GACTCCCTTG 3400 |
| CCAGCTCCAG | AGTGGGGGGG | CTGTCCCAGG | GGGCAAGAAG | GGGTGTCAGG 3450 |
| GCCCAGTGAC | AAAATCATTG | GGGTTTGTAG | TCCCAACTTG | CTGCTGTCAC 3500 |
| CACCAAACTC | AATCATTTTT | TTCCCTTGTA | AATGCCCCTC | CCCCAGCTGC 3550 |
| TGCCTTCATA | TTGAAGGTTT | TTGAGTTTTG | TTTTGGTCT | TAATTTTTCT 3600 |
| CCCCGTTCCC | TTTTTGTTTC | TTCGTTTTGT | TTTCTACCG | TCCTTGTCAT 3650 |
| AACTTTGTGT | TGGAGGGAAC | CTGTTTCACT | ATGGCCTCCT | TTGCCCAAGT 3700 |
| TGAAACAGGG | GCCCATCATC | ATGTCTGTTT | CCAGAACAGT | GCCTTGGTCA 3750 |
| TCCCACATCC | CCGGACCCCG | CCTGGGACCC | CCAAGCTGTG | TCCTATGAAG 3800 |
| GGGTGTGGGG | TGAGGTAGTG | AAAAGGGCGG | TAGTTGGTGG | TGGAACCCAG 3850 |
| AAACGGACGC | CGGTGCTTGG | AGGGGTTCTT | AAATTATATT | TAAAAAAGTA 3900 |
| ACTTTTTGTA | TAAATAAAAG | AAAATGGGAC | GTGTCCCAGC | TCCAGGGGTA 3950 |
| AAAAAAAAAA | AAAAAAAA 3969 | | | |

( 2 ) INFORMATION FOR SEQ ID NO:24:

( i ) SEQUENCE CHARACTERISTICS:
        ( A ) LENGTH: 1276 amino acids
        ( B ) TYPE: amino acid (D) TOPOLOGY: linear (xi) SEQUENCE DESCRIPTION: SEQ ID NO:24:

```
Met Glu Leu Arg Val Leu Leu Cys Trp Ala Ser Leu Ala Ala Ala
 1               5                  10                  15
Leu Glu Glu Thr Leu Leu Asn Thr Lys Leu Glu Thr Ala Asp Leu
                20                  25                  30
Lys Trp Val Thr Phe Pro Gln Val Asp Gly Gln Trp Glu Glu Leu
                35                  40                  45
Ser Gly Leu Asp Glu Gln His Ser Val Arg Thr Tyr Glu Val
                50                  55                  60
Cys Asp Val Gln Arg Ala Pro Gly Gln Ala His Trp Leu Arg Thr
                65                  70                  75
Gly Trp Val Pro Arg Arg Gly Ala Val His Val Tyr Ala Thr Leu
                80                  85                  90
Arg Phe Thr Met Leu Glu Cys Leu Ser Leu Pro Arg Ala Gly Arg
                95                  100                 105
Ser Cys Lys Glu Thr Phe Thr Val Phe Tyr Tyr Glu Ser Asp Ala
                110                 115                 120
Asp Thr Ala Thr Ala Leu Thr Pro Ala Trp Met Glu Asn Pro Tyr
                125                 130                 135
Ile Lys Val Asp Thr Val Ala Ala Glu His Leu Thr Arg Lys Arg
                140                 145                 150
Pro Gly Ala Glu Ala Thr Gly Lys Val Asn Val Lys Thr Leu Arg
                155                 160                 165
Leu Gly Pro Leu Ser Lys Ala Gly Phe Tyr Leu Ala Phe Gln Asp
                170                 175                 180
Gln Gly Ala Cys Met Ala Leu Leu Ser Leu His Leu Phe Tyr Lys
                185                 190                 195
Lys Cys Ala Gln Leu Thr Val Asn Leu Thr Arg Phe Pro Glu Thr
                200                 205                 210
Val Pro Arg Glu Leu Val Val Pro Val Ala Gly Ser Cys Val Val
                215                 220                 225
Asp Ala Val Pro Ala Pro Gly Pro Ser Pro Ser Leu Tyr Cys Arg
                230                 235                 240
Glu Asp Gly Gln Trp Ala Glu Gln Pro Val Thr Gly Cys Ser Cys
                245                 250                 255
Ala Pro Gly Phe Glu Ala Ala Glu Gly Asn Thr Lys Cys Arg Ala
                260                 265                 270
Cys Ala Gln Gly Thr Phe Lys Pro Leu Ser Gly Glu Gly Ser Cys
                275                 280                 285
Gln Pro Cys Pro Ala Asn Ser His Ser Asn Thr Ile Gly Ser Ala
                290                 295                 300
Val Cys Gln Cys Arg Val Gly Tyr Phe Arg Ala Arg Thr Asp Pro
                305                 310                 315
Arg Gly Ala Pro Cys Thr Thr Pro Pro Ser Ala Pro Arg Ser Val
                320                 325                 330
Val Ser Arg Leu Asn Gly Ser Ser Leu His Leu Glu Trp Ser Ala
                335                 340                 345
Pro Leu Glu Ser Gly Gly Arg Glu Asp Leu Thr Tyr Ala Leu Arg
                350                 355                 360
Cys Arg Glu Cys Arg Pro Gly Gly Ser Cys Ala Pro Cys Gly Gly
                365                 370                 375
Asp Leu Thr Phe Asp Pro Gly Pro Arg Asp Leu Val Glu Pro Trp
```

|     |     |     |     | 380 |     |     |     | 385 |     |     |     | 390 |
|-----|-----|-----|-----|-----|-----|-----|-----|-----|-----|-----|-----|-----|
| Val | Val | Val | Arg | Gly | Leu | Arg | Pro | Asp | Phe | Thr | Tyr | Thr | Phe | Glu |
| Val | Thr | Ala | Leu | Asn 395 | Gly | Val | Ser | Ser 400 | Leu | Ala | Thr | Gly | Pro | Val 405 |
| Pro | Phe | Glu | Pro | Val 410 | Asn | Val | Thr | Thr 415 | Asp | Arg | Glu | Val | Pro 420 |
| Ala | Val | Ser | Asp | Ile 425 | Arg | Val | Thr | Arg 430 | Ser | Ser | Pro | Ser | Ser 435 | Leu |
| Ser | Leu | Ala | Trp | Ala 440 | Val | Pro | Arg | Ala 445 | Pro | Ser | Gly | Ala | Val 450 | Leu |
| Asp | Tyr | Glu | Val | Lys 455 | Tyr | His | Glu | Lys 460 | Gly | Ala | Glu | Gly | Pro 465 | Ser |
| Ser | Val | Arg | Phe | Leu 470 | Lys | Thr | Ser | Glu 475 | Asn | Arg | Ala | Glu | Leu 480 | Arg |
| Gly | Leu | Lys | Arg | Gly 485 | Ala | Ser | Tyr | Leu 490 | Val | Gln | Val | Arg | Ala 495 | Arg |
| Ser | Glu | Ala | Gly | Tyr 500 | Gly | Pro | Phe | Gly 505 | Gln | Glu | His | His | Ser 510 | Gln |
| Thr | Gln | Leu | Asp | Glu 515 | Ser | Glu | Gly | Trp 520 | Arg | Glu | Gln | Leu | Ala 525 | Leu |
| Ile | Ala | Gly | Thr | Ala 530 | Val | Val | Gly | Val 535 | Val | Leu | Val | Leu | Val 540 | Val |
| Ile | Val | Val | Ala | Val 545 | Leu | Cys | Leu | Arg 550 | Lys | Gln | Ser | Asn | Gly 555 | Arg |
| Glu | Ala | Glu | Tyr | Ser 560 | Asp | Lys | His | Gly 565 | Gln | Tyr | Leu | Ile | Gly 570 | His |
| Gly | Thr | Lys | Val | Tyr 575 | Ile | Asp | Pro | Phe 580 | Thr | Tyr | Glu | Asp | Pro 585 | Asn |
| Glu | Ala | Val | Arg | Glu 590 | Phe | Ala | Lys | Glu 595 | Ile | Asp | Val | Ser | Tyr 600 | Val |
| Lys | Ile | Glu | Glu | Val 605 | Ile | Gly | Ala | Gly 610 | Glu | Phe | Gly | Glu | Val 615 | Cys |
| Arg | Gly | Arg | Leu | Lys 620 | Ala | Pro | Gly | Lys 625 | Lys | Glu | Ser | Cys | Val 630 | Ala |
| Ile | Lys | Thr | Leu | Lys 635 | Gly | Gly | Tyr | Thr 640 | Glu | Arg | Gln | Arg | Arg 645 | Glu |
| Phe | Leu | Ser | Glu | Ala 650 | Ser | Ile | Met | Gly 655 | Gln | Phe | Glu | His | Pro 660 | Asn |
| Ile | Ile | Arg | Leu | Glu 665 | Gly | Val | Val | Thr 670 | Asn | Ser | Met | Pro | Val 675 | Met |
| Ile | Leu | Thr | Glu | Phe 680 | Met | Glu | Asn | Gly 685 | Ala | Leu | Asp | Ser | Phe 690 | Leu |
| Arg | Leu | Asn | Asp | Gly 695 | Gln | Phe | Thr | Val 700 | Ile | Gln | Leu | Val | Gly 705 | Met |
| Leu | Arg | Gly | Ile | Ala 710 | Ser | Gly | Met | Arg 715 | Tyr | Leu | Ala | Glu | Met 720 | Ser |
| Tyr | Val | His | Arg | Asp 725 | Leu | Ala | Ala | Arg 730 | Asn | Ile | Leu | Val | Asn 735 | Ser |
| Asn | Leu | Val | Cys | Lys 740 | Val | Ser | Asp | Phe 745 | Gly | Leu | Ser | Arg | Phe 750 | Leu |
| Glu | Glu | Asn | Ser | Ser 755 | Asp | Pro | Thr | Tyr 760 | Thr | Ser | Ser | Leu | Gly 765 | Gly |
|     |     |     |     | 770 |     |     |     | 775 |     |     |     |     | 780 |     |

-continued

| | | | | | | | | | | | | | |
|---|---|---|---|---|---|---|---|---|---|---|---|---|---|
| Lys | Ile | Pro | Ile | Arg 785 | Trp | Thr | Ala | Pro 790 | Glu | Ala | Ile | Ala | Phe Arg 795 |
| Lys | Phe | Thr | Ser | Ala 800 | Ser | Asp | Ala | Trp 805 | Ser | Tyr | Gly | Ile | Val Met 810 |
| Trp | Glu | Val | Met | Ser 815 | Phe | Gly | Glu | Arg 820 | Pro | Tyr | Trp | Asp | Met Ser 825 |
| Asn | Gln | Asp | Val | Ile 830 | Asn | Ala | Ile | Glu 835 | Gln | Asp | Tyr | Arg | Leu Pro 840 |
| Pro | Pro | Pro | Asp | Cys 845 | Pro | Thr | Ser | Leu 850 | His | Gln | Leu | Met | Leu Asp 855 |
| Cys | Trp | Gln | Lys | Asp 860 | Arg | Asn | Ala | Arg 865 | Pro | Arg | Phe | Pro | Gln Val 870 |
| Val | Ser | Ala | Leu | Asp 875 | Lys | Met | Ile | Arg 880 | Asn | Pro | Ala | Ser | Leu Lys 885 |
| Ile | Val | Ala | Arg | Glu 890 | Asn | Gly | Gly | Ala 895 | Ser | His | Pro | Leu | Leu Asp 900 |
| Gln | Arg | Gln | Pro | His 905 | Tyr | Ser | Ala | Phe 910 | Gly | Ser | Val | Gly | Glu Trp 915 |
| Leu | Arg | Ala | Ile | Lys 920 | Met | Gly | Arg | Tyr 925 | Glu | Glu | Ser | Phe | Ala Ala 930 |
| Ala | Gly | Phe | Gly | Ser 935 | Phe | Glu | Leu | Val 940 | Ser | Gln | Ile | Ser | Ala Glu 945 |
| Asp | Leu | Leu | Arg | Ile 950 | Gly | Val | Thr | Leu 955 | Ala | Gly | His | Gln | Lys Lys 960 |
| Ile | Leu | Ala | Ser | Val 965 | Gln | His | Met | Lys 970 | Ser | Gln | Ala | Lys | Pro Gly 975 |
| Thr | Pro | Gly | Gly | Thr 980 | Gly | Gly | Pro | Ala 985 | Pro | Gln | Tyr | Pro | Ala Gly 990 |
| Thr | Pro | His | Pro | Arg 995 | Asp | Thr | Ala | Ser 1000 | Pro | Phe | Ser | Gly | Ala Glu 1005 |
| Trp | Gly | Leu | Thr | Glu 1010 | Ala | Pro | Ser | Pro 1015 | Val | Pro | Arg | Trp | Ile Ala 1020 |
| Leu | Ala | Arg | Gly | Val 1025 | Arg | Ser | Trp | Gln 1030 | Phe | Gly | Glu | Thr | Gly Phe 1035 |
| Gly | Gly | Ser | Ala | Ile 1040 | Ile | Gly | Gly | Glu 1045 | Asn | His | Pro | Pro | Ala Thr 1050 |
| Ser | Gly | Asn | Ser | Arg 1055 | Pro | Arg | Val | Arg 1060 | Ala | Pro | Phe | Pro | Gln Asp 1065 |
| Trp | Val | Pro | Glu | Glu 1070 | Lys | Glu | Val | Pro 1075 | Asn | Ile | Ser | Gln | Pro Pro 1080 |
| Gln | Val | Pro | Pro | Ser 1085 | Pro | Trp | Val | Arg 1090 | Ser | Arg | Arg | Pro | Lys Arg 1095 |
| Val | Leu | Pro | Cys | Gln 1100 | Leu | Gln | Ser | Gly 1105 | Gly | Ala | Val | Pro | Gly Gly 1110 |
| Lys | Lys | Gly | Cys | Gln 1115 | Gly | Pro | Val | Thr 1120 | Lys | Ser | Leu | Gly | Phe Val 1125 |
| Val | Pro | Thr | Cys | Cys 1130 | Cys | His | His | Gln 1135 | Thr | Gln | Ser | Phe | Phe Ser 1140 |
| Leu | Val | Asn | Ala | Pro 1145 | Pro | Pro | Ala | Ala 1150 | Ala | Phe | Ile | Leu | Lys Val 1155 |
| Phe | Glu | Phe | Cys | Phe 1160 | Trp | Ser | Phe | Phe 1165 | Ser | Pro | Phe | Pro | Phe Cys 1170 |
| Phe | Phe | Val | Leu | Phe 1175 | Phe | Tyr | Arg | Pro 1180 | Cys | His | Asn | Phe | Val Leu 1185 |

```
Glu  Gly  Thr  Cys  Phe  Thr  Met  Ala  Ser  Phe  Ala  Gln  Val  Glu  Thr
               1190                1195                          1200

Gly  Ala  His  His  His  Val  Cys  Phe  Gln  Asn  Ser  Ala  Leu  Val  Ile
               1205                1210                          1215

Pro  His  Pro  Arg  Thr  Pro  Pro  Gly  Thr  Pro  Lys  Leu  Cys  Pro  Met
               1220                1225                          1230

Lys  Gly  Cys  Gly  Val  Arg  Lys  Gly  Arg  Leu  Val  Val  Glu  Pro  Arg
               1235                1240                          1245

Asn  Gly  Arg  Arg  Cys  Leu  Glu  Gly  Phe  Leu  Asn  Tyr  Ile  Lys  Ser
               1250                1255                          1260

Asn  Phe  Leu  Tyr  Lys  Lys  Lys  Met  Gly  Arg  Val  Pro  Ala  Pro  Gly
               1265                1270                          1275

Val
1276
```

( 2 ) INFORMATION FOR SEQ ID NO:25:

( i ) SEQUENCE CHARACTERISTICS:
        ( A ) LENGTH: 59 amino acids
        ( B ) TYPE: amino acid
        ( D ) TOPOLOGY: linear ( x i ) SEQUENCE DESCRIPTION: SEQ ID NO:25:

```
Ala  Arg  Asn  Ile  Leu  Val  Asn  Ser  Asn  Leu  Val  Cys  Lys  Val  Ser
 1                   5                        10                         15

Asp  Phe  Gly  Leu  Ser  Arg  Phe  Leu  Glu  Asp  Thr  Ser  Asp  Pro
                    20                        25                         30

Thr  Tyr  Thr  Ser  Ala  Leu  Gly  Gly  Lys  Ile  Pro  Met  Arg  Trp  Thr
                    35                        40                         45

Ala  Pro  Glu  Ala  Ile  Gln  Tyr  Arg  Lys  Phe  Ala  Ser  Ala  Ser
                    50                        55                         59
```

( 2 ) INFORMATION FOR SEQ ID NO:26:

( i ) SEQUENCE CHARACTERISTICS:
        ( A ) LENGTH: 54 amino acids
        ( B ) TYPE: amino acid
        ( D ) TOPOLOGY: linear ( x i ) SEQUENCE DESCRIPTION: SEQ ID NO:26:

```
Asn  Val  Leu  Val  Lys  Ser  Pro  Asn  His  Val  Lys  Ile  Thr  Asp  Phe
 1                   5                        10                         15

Gly  Leu  Ala  Arg  Leu  Leu  Glu  Gly  Asp  Glu  Lys  Glu  Tyr  Asn  Ala
                    20                        25                         30

Asp  Gly  Gly  Lys  Met  Pro  Ile  Lys  Trp  Met  Ala  Leu  Glu  Cys  Ile
                    35                        40                         45

His  Tyr  Arg  Lys  Phe  Thr  His  Gln  Ser
                    50                   54
```

( 2 ) INFORMATION FOR SEQ ID NO:27:

( i ) SEQUENCE CHARACTERISTICS:
        ( A ) LENGTH: 54 amino acids
        ( B ) TYPE: amino acid
        ( D ) TOPOLOGY: linear ( x i ) SEQUENCE DESCRIPTION: SEQ ID NO:27:

```
Asn  Cys  Met  Leu  Ala  Gly  Asp  Met  Thr  Val  Cys  Val  Ala  Asp  Phe
 1                   5                        10                         15

Gly  Leu  Ser  Trp  Lys  Ile  Tyr  Ser  Gly  Ala  Thr  Ile  Val  Arg  Gly
```

20                          25                          30
Cys  Ala  Ser  Lys  Leu  Pro  Val  Lys  Trp  Leu  Ala  Leu  Gly  Ser  Leu
                       35                          40                          45

Ala  Asp  Asn  Leu  Tyr  Thr  Val  His  Ser
                       50                      54

( 2 ) INFORMATION FOR SEQ ID NO:28:

( i ) SEQUENCE CHARACTERISTICS:
        ( A ) LENGTH: 27 amino acids
        ( B ) TYPE: amino acid
        ( D ) TOPOLOGY: linear ( x i ) SEQUENCE DESCRIPTION: SEQ ID NO:28:

Asn  Cys  Leu  Val  Gly  Lys  Asn  Tyr  Thr  Ile  Lys  Ile  Ala  Asp  Phe
 1                      5                          10                         15

Gly  Met  Ser  Arg  Asn  Leu  Tyr  Ser  Gly  Asp  Tyr  Tyr
                       20                          25        27

( 2 ) INFORMATION FOR SEQ ID NO:29:

( i ) SEQUENCE CHARACTERISTICS:
        ( A ) LENGTH: 58 amino acids
        ( B ) TYPE: amino acid
        ( D ) TOPOLOGY: linear ( x i ) SEQUENCE DESCRIPTION: SEQ ID NO:29:

Thr  Arg  Asn  Ile  Leu  Val  Glu  Asn  Glu  Asn  Arg  Val  Lys  Ile  Gly
 1                      5                          10                         15

Asp  Phe  Gly  Leu  Thr  Lys  Val  Leu  Pro  Gln  Asp  Lys  Glu  Tyr  Tyr
                       20                          25                         30

Lys  Val  Lys  Glu  Pro  Gly  Glu  Ser  Pro  Ile  Phe  Trp  Tyr  Ala  Pro
                       35                          40                         45

Glu  Ser  Leu  Thr  Glu  Ser  Leu  Phe  Ser  Val  Ala  Ser  Asp
                       50                          55              58

( 2 ) INFORMATION FOR SEQ ID NO:30:

( i ) SEQUENCE CHARACTERISTICS:
        ( A ) LENGTH: 58 amino acids
        ( B ) TYPE: amino acid
        ( D ) TOPOLOGY: linear ( x i ) SEQUENCE DESCRIPTION: SEQ ID NO:30:

Ala  Arg  Asn  Ile  Leu  Val  Asn  Ser  Asn  Leu  Val  Cys  Lys  Val  Ser
 1                      5                          10                         15

Asp  Phe  Gly  Met  Ser  Arg  Val  Leu  Glu  Asp  Asp  Pro  Glu  Ala  Ala
                       20                          25                         30

Tyr  Thr  Thr  Arg  Gly  Gly  Lys  Ile  Pro  Ile  Arg  Trp  Thr  Ala  Pro
                       35                          40                         45

Glu  Ala  Ile  Ala  Tyr  Arg  Lys  Phe  Thr  Ser  Ala  Ser  Asp
                       50                          55              58

( 2 ) INFORMATION FOR SEQ ID NO:31:

( i ) SEQUENCE CHARACTERISTICS:
        ( A ) LENGTH: 4425 bases
        ( B ) TYPE: nucleic acid
        ( C ) STRANDEDNESS: single
        ( D ) TOPOLOGY: linear ( x i ) SEQUENCE DESCRIPTION: SEQ ID NO:31:

TCGGGTCGGA  CCCACGCGCA  GCGGCCGGAG  ATGCAGCGGG  GCGCCGCGCT    50

```
GTGCCTGCGA CTGTGGCTCT GCCTGGGACT CCTGGACGGC CTGGTGAGTG    100
GCTACTCCAT GACCCCCCCG ACCTTGAACA TCACGGAGGA GTCACACGTC    150
ATCGACACCG GTGACAGCCT GTCCATCTCC TGCAGGGGAC AGCACCCCCT    200
CGAGTGGGCT TGGCCAGGAG CTCAGGAGGC GCCAGCCACC GGAGACAAGG    250
ACAGCGAGGA CACGGGGGTG GTGCGAGACT GCGAGGGCAC AGACGCCAGG    300
CCCTACTGCA AGGTGTTGCT GCTGCACGAG GTACATGCCA ACGACACAGG    350
CAGCTACGTC TGCTACTACA AGTACATCAA GGCACGCATC GAGGGCACCA    400
CGGCCGCCAG CTCCTACGTG TTCGTGAGAG ACTTTGAGCA GCCATTCATC    450
AACAAGCCTG ACACGCTCTT GGTCAACAGG AAGGACGCCA TGTGGGTGCC    500
CTGTCTGGTG TCCATCCCCG GCCTCAATGT CACGCTGCGC TCGCAAAGCT    550
CGGTGCTGTG GCCAGACGGG CAGGAGGTGG TGTGGGATGA CCGGCGGGGC    600
ATGCTCGTGT CCACGCCACT GCTGCACGAT GCCCTGTACC TGCAGTGCGA    650
GACCACCTGG GGAGACCAGG ACTTCCTTTC CAACCCCTTC CTGGTGCACA    700
TCACAGGCAA CGAGCTCTAT GACATCCAGC TGTTGCCCAG GAAGTCGCTG    750
GAGCTGCTGG TAGGGGAGAA GCTGGTCCTG AACTGCACCG TGTGGGCTGA    800
GTTTAACTCA GGTGTCACCT TTGACTGGGA CTACCCAGGG AAGCAGGCAG    850
AGCGGGGTAA GTGGGTGCCC GAGCGACGCT CCCAGCAGAC CCACACAGAA    900
CTCTCCAGCA TCCTGACCAT CCACAACGTC AGCCAGCACG ACCTGGGCTC    950
GTATGTGTGC AAGGCCAACA ACGGCATCCA GCGATTTCGG GAGAGCACCG   1000
AGGTCATTGT GCATGAAAAT CCCTTCATCA GCGTCGAGTG GCTCAAAGGA   1050
CCCATCCTGG AGGCCACGGC AGGAGACGAG CTGGTGAAGC TGCCCGTGAA   1100
GCTGGCAGCG TACCCCCCGC CCGAGTTCCA GTGGTACAAG GATGGAAAGG   1150
CACTGTCCGG GCGCCACAGT CCACATGCCC TGGTGCTCAA GGAGGTGACA   1200
GAGGCCAGCA CAGGCACCTA CACCCTCGCC CTGTGGAACT CCGCTGCTGG   1250
CCTGAGGCGC AACATCAGCC TGGAGCTGGT GGTGAATGTG CCCCCCAGA    1300
TACATGAGAA GGAGGCCTCC TCCCCCAGCA TCTACTCGCG TCACAGCCGC   1350
CAGGCCCTCA CCTGCACGGC CTACGGGGTG CCCCTGCCTC TCAGCATCCA   1400
GTGGCACTGG CGGCCCTGGA CACCCTGCAA GATGTTTGCC CAGCGTAGTC   1450
TCCGGCGGCG GCAGCAGCAA GACCTCATGC CACAGTGCCG TGACTGGAGG   1500
GCGGTGACCA CGCAGGATGC CGTGAACCCC ATCGAGAGCC TGGACACCTG   1550
GACCGAGTTT GTGGAGGGAA AGAATAAGAC TGTGAGCAAG CTGGTGATCC   1600
AGAATGCCAA CGTGTCTGCC ATGTACAAGT GTGTGGTCTC CAACAAGGTG   1650
GGCCAGGATG AGCGGCTCAT CTACTTCTAT GTGACCACCA TCCCCGACGG   1700
CTTCACCATC GAATCCAAGC CATCCGAGGA GCTACTAGAG GCCAGCCGG    1750
TGCTCCTGAG CTGCCAAGCC GACAGCTACA AGTACGAGCA TCTGCGCTGG   1800
TACCGCCTCA ACCTGTCCAC GCTGCACGAT GCGCACGGGA ACCCGCTTCT   1850
GCTCGACTGC AAGAACGTGC ATCTGTTCGC CACCCCTCTG GCCGCCAGCC   1900
TGGAGGAGGT GGCACCTGGG GCGCGCCACG CCACGCTCAG CCTGAGTATC   1950
CCCCGCGTCG CGCCCGAGCA CGAGGGCCAC TATGTGTGCG AAGTGCAAGA   2000
CCGGCGCAGC CATGACAAGC ACTGCCACAA GAAGTACCTG TCGGTGCAGG   2050
```

```
CCCTGGAAGC CCCTCGGCTC ACGCAGAACT TGACCGACCT CCTGGTGAAC 2100
GTGAGCGACT CGCTGGAGAT GCAGTGCTTG GTGGCCGGAG CGCACGCGCC 2150
CAGCATCGTG TGGTACAAAG ACGAGAGGCT GCTGGAGGAA AAGTCTGGAG 2200
TCGACTTGGC GGACTCCAAC CAGAAGCTGA GCATCCAGCG CGTGCGCGAG 2250
GAGGATGCGG GACGCTATCT GTGCAGCGTG TGCAACGCCA AGGGCTGCGT 2300
CAACTCCTCC GCCAGCGTGG CCGTGGAAGG CTCCGAGGAT AAGGGCAGCA 2350
TGGAGATCGT GATCCTTGTC GGTACCGGCG TCATCGCTGT CTTCTTCTGG 2400
GTCCTCCTCC TCCTCATCTT CTGTAACATG AGGAGGCCGG CCCACGCAGA 2450
CATCAAGACG GGCTACCTGT CCATCATCAT GGACCCCGGG GAGGTGCCTC 2500
TGGAGGAGCA ATGCGAATAC CTGTCCTACG ATGCCAGCCA GTGGGAATTC 2550
CCCCGAGAGC GGCTGCACCT GGGGAGAGTG CTCGGCTACG GCGCCTTCGG 2600
GAAGGTGGTG GAAGCCTCCG CTTTCGGCAT CCACAAGGGC AGCAGCTGTG 2650
ACACCGTGGC CGTGAAAATG CTGAAAGAGG GCGCCACGGC CAGCGAGCAC 2700
CGCGCGCTGA TGTCGGAGCT CAAGATCCTC ATTCACATCG GCAACCACCT 2750
CAACGTGGTC AACCTCCTCG GGGCGTGCAC CAAGCCGCAG GGCCCCCTCA 2800
TGGTGATCGT GGAGTTCTGC AAGTACGGCA ACCTCTCCAA CTTCCTGCGC 2850
GCCAAGCGGG ACGCCTTCAG CCCCTGCGCG GAGAAGTCTC CCGAGCAGCG 2900
CGGACGCTTC CGCGCCATGG TGGAGCTCGC CAGGCTGGAT CGGAGGCGGC 2950
CGGGGAGCAG CGACAGGGTC CTCTTCGCGC GGTTCTCGAA GACCGAGGGC 3000
GGAGCGAGGC GGGCTTCTCC AGACCAAGAA GCTGAGGACC TGTGGCTGAG 3050
CCCGCTGACC ATGGAAGATC TTGTCTGCTA CAGCTTCCAG GTGGCCAGAG 3100
GGATGGAGTT CCTGGCTTCC CGAAAGTGCA TCCACAGAGA CCTGGCTGCT 3150
CGGAACATTC TGCTGTCGGA AAGCGACGTG GTGAAGATCT GTGACTTTGG 3200
CCTTGCCCGG GACATCTACA AAGACCCTGA CTACGTCCGC AAGGGCAGTG 3250
CCCGGCTGCC CCTGAAGTGG ATGGCCCCTG AAAGCATCTT CGACAAGGTG 3300
TACACCACGC AGAGTGACGT GTGGTCCTTT GGGGTGCTTC TCTGGGAGAT 3350
CTTCTCTCTG GGGGCCTCCC CGTACCCTGG GGTGCAGATC AATGAGGAGT 3400
TCTGCCAGCG GCTGAGAGAC GGCACAAGGA TGAGGGCCCC GGAGCTGGCC 3450
ACTCCCGCCA TACGCCGCAT CATGCTGAAC TGCTGGTCCG GAGACCCCAA 3500
GGCGAGACCT GCATTCTCGG AGCTGGTGGA GATCCTGGGG GACCTGCTCC 3550
AGGGCAGGGG CCTGCAAGAG GAAGAGGAGG TCTGCATGGC CCCGCGCAGC 3600
TCTCAGAGCT CAGAAGAGGG CAGCTTCTCG CAGGTGTCCA CCATGGCCCT 3650
ACACATCGCC CAGGCTGACG CTGAGGACAG CCCGCCAAGC CTGCAGCGCC 3700
ACAGCCTGGC CGCCAGGTAT TACAACTGGG TGTCCTTTCC CGGGTGCCTG 3750
GCCAGAGGGG CTGAGACCCG TGGTTCCTCC AGGATGAAGA CATTTGAGGA 3800
ATTCCCCATG ACCCCAACGA CCTACAAAGG CTCTGTGGAC AACCAGACAG 3850
ACAGTGGGAT GGTGCTGGCC TCGGAGGAGT TTGAGCAGAT AGAGAGCAGG 3900
CATAGACAAG AAAGCGGCTT CAGGTAGCTG AAGCAGAGAG AGAAGGCA 3950
GCATACGTCA GCATTTTCTT CTCTGCACTT ATAAGAAAGA TCAAAGACTT 4000
TAAGACTTTC GCTATTTCTT CTGCTATCTA CTACAAACTT CAAAGAGGAA 4050
```

```
CCAGGAGGCC  AAGAGGAGCA  TGAAAGTGGA  CAAGGAGTGT  GACCACTGAA     4100

GCACCACAGG  GAGGGGTTAG  GCCTCCGGAT  GACTGCGGGC  AGGCCTGGAT     4150

AATATCCAGC  CTCCCACAAG  AAGCTGGTGG  AGCAGAGTGT  TCCCTGACTC     4200

CTCCAAGGAA  AGGGAGACGC  CCTTTCATGG  TCTGCTGAGT  AACAGGTGCC     4250

TTCCCAGACA  CTGGCGTTAC  TGCTTGACCA  AAGAGCCCTC  AAGCGGCCCT     4300

TATGCCAGCG  TGACAGAGGG  CTCACCTCTT  GCCTTCTAGG  TCACTTCTCA     4350

CAATGTCCCT  TCAGCACCTG  ACCCTGTGCC  CGCCAGTTAT  TCCTTGGTAA     4400

TATGAGTAAT  ACATCAAAGA  GTAGT                                  4425
```

( 2 ) INFORMATION FOR SEQ ID NO:32:

( i ) SEQUENCE CHARACTERISTICS:
    ( A ) LENGTH: 4425 bases
    ( B ) TYPE: nucleic acid
    ( C ) STRANDEDNESS: single
    ( D ) TOPOLOGY: linear ( x i ) SEQUENCE DESCRIPTION: SEQ ID NO:32:

```
AGCCCAGCCT  GGGTGCGCGT  CGCCGGCCTC  TACGTCGCCC  CGCGGCGCGA     50

CACGGACGCT  GACACCGAGA  CGGACCCTGA  GGACCTGCCG  GACCACTCAC    100

CGATGAGGTA  CTGGGGGGGC  TGGAACTTGT  AGTGCCTCCT  CAGTGTGCAG    150

TAGCTGTGGC  CACTGTCGGA  CAGGTAGAGG  ACGTCCCCTG  TCGTGGGGA     200

GCTCACCCGA  ACCGGTCCTC  GAGTCCTCCG  CGGTCGGTGG  CCTCTGTTCC    250

TGTCGCTCCT  GTGCCCCCAC  CACGCTCTGA  CGCTCCCGTG  TCTGCGGTCC    300

GGGATGACGT  TCCACAACGA  CGACGTGCTC  CATGTACGGT  TGCTGTGTCC    350

GTCGATGCAG  ACGATGATGT  TCATGTAGTT  CCGTGCGTAG  CTCCCGTGGT    400

GCCGGCGGTC  GAGGATGCAC  AAGCACTCTC  TGAAACTCGT  CGGTAAGTAG    450

TTGTTCGGAC  TGTGCGAGAA  CCAGTTGTCC  TTCCTGCGGT  ACACCCACGG    500

GACAGACCAC  AGGTAGGGGC  CGGAGTTACA  GTGCGACGCG  AGCGTTTCGA    550

GCCACGACAC  CGGTCTGCCC  GTCCTCCACC  ACACCCTACT  GGCCGCCCG     600

TACGAGCACA  GGTGCGGTGA  CGACGTGCTA  CGGGACATGG  ACGTCACGCT    650

CTGGTGGACC  CCTCTGGTCC  TGAAGGAAAG  GTTGGGGAAG  GACCACGTGT    700

AGTGTCCGTT  GCTCGAGATA  CTGTAGGTCG  ACAACGGGTC  CTTCAGCGAC    750

CTCGACGACC  ATCCCCTCTT  CGACCAGGAC  TTGACGTGGC  ACACCCGACT    800

CAAATTGAGT  CCACAGTGGA  AACTGACCCT  GATGGGTCCC  TTCGTCCGTC    850

TCGCCCCATT  CACCCACGGG  CTCGCTGCGA  GGGTCGTCTG  GGTGTGTCTT    900

GAGAGGTCGT  AGGACTGGTA  GGTGTTGCAG  TCGGTCGTGC  TGGACCCGAG    950

CATACACACG  TTCCGGTTGT  TGCCGTAGGT  CGCTAAAGCC  CTCTCGTGGC   1000

TCCAGTAACA  CGTACTTTTA  GGGAAGTAGT  CGCAGCTCAC  CGAGTTTCCT   1050

GGGTAGGACC  TCCGGTGCCG  TCCTCTGCTC  GACCACTTCG  ACGGGCACTT   1100

CGACCGTCGC  ATGGGGGGCG  GGCTCAAGGT  CACCATGTTC  CTACCTTTCC   1150

GTGACAGGCC  CGCGGTGTCA  GGTGTACGGG  ACCACGAGTT  CCTCCACTGT   1200

CTCCGGTCGT  GTCCGTGGAT  GTGGGAGCGG  GACACCTTGA  GGCGACGACC   1250

GGACTCCGCG  TTGTAGTCGG  ACCTCGACCA  CCACTTACAC  GGGGGGGTCT   1300
```

```
ATGTACTCTT CCTCCGGAGG AGGGGGTCGT AGATGAGCGC AGTGTCGGCG   1350
GTCCGGGAGT GGACGTGCCG GATGCCCCAC GGGGACGGAG AGTCGTAGGT   1400
CACCGTGACC GCCGGGACCT GTGGGACGTT CTACAAACGG GTCGCATCAG   1450
AGGCCGCCGC CGTCGTCGTT CTGGAGTACG GTGTCACGGC ACTGACCTCC   1500
CGCCACTGGT GCGTCCTACG GCACTTGGGG TAGCTCTCGG ACCTGTGGAC   1550
CTGGCTCAAA CACCTCCCTT TCTTATTCTG ACACTCGTTC GACCACTAGG   1600
TCTTACGGTT GCACAGACGG TACATGTTCA CACACCAGAG GTTGTTCCAC   1650
CCGGTCCTAC TCGCCGAGTA GATGAAGATA CACTGGTGGT AGGGGCTGCC   1700
GAAGTGGTAG CTTAGGTTCG GTAGGCTCCT CGATGATCTC CCGGTCGGCC   1750
ACGAGGACTC GACGGTTCGG CTGTCGATGT TCATGCTCGT AGACGCGACC   1800
ATGGCGGAGT TGGACAGGTG CGACGTGCTA CGCGTGCCCT TGGGCGAAGA   1850
CGAGCTGACG TTCTTGCACG TAGACAAGCG GTGGGAGAC CGGCGGTCGG    1900
ACCTCCTCCA CCGTGGACCC CGCGCGGTGC GGTGCGAGTC GGACTCATAG   1950
GGGGCGCAGC GCGGGCTCGT GCTCCCGGTG ATACACACGC TTCACGTTCT   2000
GGCCGCGTCG GTACTGTTCG TGACGGTGTT CTTCATGGAC AGCCACGTCC   2050
GGGACCTTCG GGGAGCCGAG TGCGTCTTGA ACTGGCTGGA GGACCACTTG   2100
CACTCGCTGA GCGACCTCTA CGTCACGAAC CACCGGCCTC GCGTGCGCGG   2150
GTCGTAGCAC ACCATGTTTC TGCTCTCCGA CGACCTCCTT TTCAGACCTC   2200
AGCTGAACCG CCTGAGGTTG GTCTTCGACT CGTAGGTCGC GCACGCGCTC   2250
CTCCTACGCC CTGCGATAGA CACGTCGCAC ACGTTGCGGT TCCCGACGCA   2300
GTTGAGGAGG CGGTCGCACC GGCACCTTCC GAGGCTCCTA TTCCCGTCGT   2350
ACCTCTAGCA CTAGGAACAG CCATGGCCGC AGTAGCGACA GAAGAAGACC   2400
CAGGAGGAGG AGGAGTAGAA GACATTGTAC TCCTCCGGCC GGGTGCGTCT   2450
GTAGTTCTGC CCGATGGACA GGTAGTAGTA CCTGGGGCCC CTCCACGGAG   2500
ACCTCCTCGT TACGCTTATG GACAGGATGC TACGGTCGGT CACCCTTAAG   2550
GGGCTCTCG CCGACGTGGA CCCCTCTCAC GAGCCGATGC CGCGGAAGCC    2600
CTTCCACCAC CTTCGGAGGC GAAAGCCGTA GGTGTTCCCG TCGTCGACAC   2650
TGTGGCACCG GCACTTTTAC GACTTTCTCC CGCGGTGCCG GTCGCTCGTG   2700
GCGCGCGACT ACAGCCTCGA GTTCTAGGAG TAAGTGTAGC CGTTGGTGGA   2750
GTTGCACCAG TTGGAGGAGC CCCGCACGTG GTTCGGCGTC CGGGGGAGT    2800
ACCACTAGCA CCTCAAGACG TTCATGCCGT TGGAGAGGTT GAAGGACGCG   2850
CGGTTCGCCC TGCGGAAGTC GGGGACGCGC CTCTTCAGAG GGCTCGTCGC   2900
GCCTGCGAAG GCGCGGTACC ACCTCGAGCG GTCCGACCTA GCCTCCGCCG   2950
GCCCCTCGTC GCTGTCCCAG GAGAAGCGCG CCAAGAGCTT CTGGCTCCCG   3000
CCTCGCTCCG CCCGAAGAGG TCTGGTTCTT CGACTCCTGG ACACCGACTC   3050
GGGCGACTGG TACCTTCTAG AACAGACGAT GTCGAAGGTC CACCGGTCTC   3100
CCTACCTCAA GGACCGAAGG GCTTTCACGT AGGTGTCTCT GGACCGACGA   3150
GCCTTGTAAG ACGACAGCCT TTCGCTGCAC CACTTCTAGA CACTGAAACC   3200
GGAACGGGCC CTGTAGATGT TTCTGGGACT GATGCAGGCG TTCCCGTCAC   3250
GGGCCGACGG GGACTTCACC TACCGGGGAC TTTCGTAGAA GCTGTTCCAC   3300
```

```
ATGTGGTGCG TCTCACTGCA CACCAGGAAA CCCCACGAAG AGACCCTCTA   3350
GAAGAGAGAC CCCCGGAGGG GCATGGGACC CCACGTCTAG TTACTCCTCA   3400
AGACGGTCGC CGACTCTCTG CCGTGTTCCT ACTCCCGGGG CCTCGACCGG   3450
TGAGGGCGGT ATGCGGCGTA GTACGACTTG ACGACCAGGC CTCTGGGGTT   3500
CCGCTCTGGA CGTAAGAGCC TCGACCACCT CTAGGACCCC CTGGACGAGG   3550
TCCCGTCCCC GGACGTTCTC CTTCTCCTCC AGACGTACCG GGGCGCGTCG   3600
AGAGTCTCGA GTCTTCTCCC GTCGAAGAGC GTCCACAGGT GGTACCGGGA   3650
TGTGTAGCGG GTCCGACTGC GACTCCTGTC GGGCGGTTCG GACGTCGCGG   3700
TGTCGGACCG GCGGTCCATA ATGTTGACCC ACAGGAAAGG GCCCACGGAC   3750
CGGTCTCCCC GACTCTGGGC ACCAAGGAGG TCCTACTTCT GTAAACTCCT   3800
TAAGGGGTAC TGGGGTTGCT GGATGTTTCC GAGACACCTG TTGGTCTGTC   3850
TGTCACCCTA CCACGACCGG AGCCTCCTCA AACTCGTCTA TCTCTCGTCC   3900
GTATCTGTTC TTTCGCCGAA GTCCATCGAC TTCGTCTCTC TCTCTTCCGT   3950
CGTATGCAGT CGTAAAAGAA GAGACGTGAA TATTCTTTCT AGTTTCTGAA   4000
ATTCTGAAAG CGATAAAGAA GACGATAGAT GATGTTTGAA GTTTCTCCTT   4050
GGTCCTCCGG TTCTCCTCGT ACTTTCACCT GTTCCTCACA CTGGTGACTT   4100
CGTGGTGTCC CTCCCCAATC CGGAGGCCTA CTGACGCCCG TCCGGACCTA   4150
TTATAGGTCG GAGGGTGTTC TTCGACCACC TCGTCTCACA AGGGACTGAG   4200
GAGGTTCCTT TCCCTCTGCG GGAAAGTACC AGACGACTCA TTGTCCACGG   4250
AAGGGTCTGT GACCGCAATG ACGAACTGGT TTCTCGGGAG TTCGCCGGGA   4300
ATACGGTCGC ACTGTCTCCC GAGTGGAGAA CGGAAGATCC AGTGAAGAGT   4350
GTTACAGGGA AGTCGTGGAC TGGGACACGG GCGGTCAATA AGGAACCATT   4400
ATACTCATTA TGTAGTTTCT CATCA                            4425
```

( 2 ) INFORMATION FOR SEQ ID NO:33:

( i ) SEQUENCE CHARACTERISTICS:
        ( A ) LENGTH: 1298 amino acids
        ( B ) TYPE: amino acid
        ( D ) TOPOLOGY: linear ( x i ) SEQUENCE DESCRIPTION: SEQ ID NO:33:

```
Met Gln Arg Gly Ala Ala Leu Cys Leu Arg Leu Trp Leu Cys Leu
 1               5                  10                  15

Gly Leu Leu Asp Gly Leu Val Ser Gly Tyr Ser Met Thr Pro Pro
                20                  25                  30

Thr Leu Asn Ile Thr Glu Glu Ser His Val Ile Asp Thr Gly Asp
                35                  40                  45

Ser Leu Ser Ile Ser Cys Arg Gly Gln His Pro Leu Glu Trp Ala
                50                  55                  60

Trp Pro Gly Ala Gln Glu Ala Pro Ala Thr Gly Asp Lys Asp Ser
                65                  70                  75

Glu Asp Thr Gly Val Val Arg Asp Cys Glu Gly Thr Asp Ala Arg
                80                  85                  90

Pro Tyr Cys Lys Val Leu Leu Leu His Glu Val His Ala Asn Asp
                95                 100                 105

Thr Gly Ser Tyr Val Cys Tyr Tyr Lys Tyr Ile Lys Ala Arg Ile
               110                 115                 120
```

-continued

| | | | | | | | | | | | | | |
|---|---|---|---|---|---|---|---|---|---|---|---|---|---|
|Glu|Gly|Thr|Thr|Ala|Ala|Ser|Ser|Tyr|Val|Phe|Val|Arg|Asp|Phe|
| | | | |125| | | |130| | | | |135|
|Glu|Gln|Pro|Phe|Ile|Asn|Lys|Pro|Asp|Thr|Leu|Leu|Val|Asn|Arg|
| | | | |140| | | |145| | | | |150|
|Lys|Asp|Ala|Met|Trp|Val|Pro|Cys|Leu|Val|Ser|Ile|Pro|Gly|Leu|
| | | | |155| | | |160| | | | |165|
|Asn|Val|Thr|Leu|Arg|Ser|Gln|Ser|Ser|Val|Leu|Trp|Pro|Asp|Gly|
| | | | |170| | | |175| | | | |180|
|Gln|Glu|Val|Val|Trp|Asp|Asp|Arg|Arg|Gly|Met|Leu|Val|Ser|Thr|
| | | | |185| | | |190| | | | |195|
|Pro|Leu|Leu|His|Asp|Ala|Leu|Tyr|Leu|Gln|Cys|Glu|Thr|Thr|Trp|
| | | | |200| | | |205| | | | |210|
|Gly|Asp|Gln|Asp|Phe|Leu|Ser|Asn|Pro|Phe|Leu|Val|His|Ile|Thr|
| | | | |215| | | |220| | | | |225|
|Gly|Asn|Glu|Leu|Tyr|Asp|Ile|Gln|Leu|Leu|Pro|Arg|Lys|Ser|Leu|
| | | | |230| | | |235| | | | |240|
|Glu|Leu|Leu|Val|Gly|Glu|Lys|Leu|Val|Leu|Asn|Cys|Thr|Val|Trp|
| | | | |245| | | |250| | | | |255|
|Ala|Glu|Phe|Asn|Ser|Gly|Val|Thr|Phe|Asp|Trp|Asp|Tyr|Pro|Gly|
| | | | |260| | | |265| | | | |270|
|Lys|Gln|Ala|Glu|Arg|Gly|Lys|Trp|Val|Pro|Glu|Arg|Arg|Ser|Gln|
| | | | |275| | | |280| | | | |285|
|Gln|Thr|His|Thr|Glu|Leu|Ser|Ser|Ile|Leu|Thr|Ile|His|Asn|Val|
| | | | |290| | | |295| | | | |300|
|Ser|Gln|His|Asp|Leu|Gly|Ser|Tyr|Val|Cys|Lys|Ala|Asn|Asn|Gly|
| | | | |305| | | |310| | | | |315|
|Ile|Gln|Arg|Phe|Arg|Glu|Ser|Thr|Glu|Val|Ile|Val|His|Glu|Asn|
| | | | |320| | | |325| | | | |330|
|Pro|Phe|Ile|Ser|Val|Glu|Trp|Leu|Lys|Gly|Pro|Ile|Leu|Glu|Ala|
| | | | |335| | | |340| | | | |345|
|Thr|Ala|Gly|Asp|Glu|Leu|Val|Lys|Leu|Pro|Val|Lys|Leu|Ala|Ala|
| | | | |350| | | |355| | | | |360|
|Tyr|Pro|Pro|Pro|Glu|Phe|Gln|Trp|Tyr|Lys|Asp|Gly|Lys|Ala|Leu|
| | | | |365| | | |370| | | | |375|
|Ser|Gly|Arg|His|Ser|Pro|His|Ala|Leu|Val|Leu|Lys|Glu|Val|Thr|
| | | | |380| | | |385| | | | |390|
|Glu|Ala|Ser|Thr|Gly|Thr|Tyr|Thr|Leu|Ala|Leu|Trp|Asn|Ser|Ala|
| | | | |395| | | |400| | | | |405|
|Ala|Gly|Leu|Arg|Arg|Asn|Ile|Ser|Leu|Glu|Leu|Val|Val|Asn|Val|
| | | | |410| | | |415| | | | |420|
|Pro|Pro|Gln|Ile|His|Glu|Lys|Glu|Ala|Ser|Ser|Pro|Ser|Ile|Tyr|
| | | | |425| | | |430| | | | |435|
|Ser|Arg|His|Ser|Arg|Gln|Ala|Leu|Thr|Cys|Thr|Ala|Tyr|Gly|Val|
| | | | |440| | | |445| | | | |450|
|Pro|Leu|Pro|Leu|Ser|Ile|Gln|Trp|His|Trp|Arg|Pro|Trp|Thr|Pro|
| | | | |455| | | |460| | | | |465|
|Cys|Lys|Met|Phe|Ala|Gln|Arg|Ser|Leu|Arg|Arg|Arg|Gln|Gln|Gln|
| | | | |470| | | |475| | | | |480|
|Asp|Leu|Met|Pro|Gln|Cys|Arg|Asp|Trp|Arg|Ala|Val|Thr|Thr|Gln|
| | | | |485| | | |490| | | | |495|
|Asp|Ala|Val|Asn|Pro|Ile|Glu|Ser|Leu|Asp|Thr|Trp|Thr|Glu|Phe|
| | | | |500| | | |505| | | | |510|
|Val|Glu|Gly|Lys|Asn|Lys|Thr|Val|Ser|Lys|Leu|Val|Ile|Gln|Asn|
| | | | |515| | | |520| | | | |525|

| | | | | | | | | | | | | |
|---|---|---|---|---|---|---|---|---|---|---|---|---|
| Ala | Asn | Val | Ser | Ala 530 | Met | Tyr | Lys | Cys 535 | Val | Ser | Asn | Lys Val 540 |
| Gly | Gln | Asp | Glu | Arg 545 | Leu | Ile | Tyr | Phe 550 | Val | Thr | Thr | Ile Pro 555 |
| Asp | Gly | Phe | Thr | Ile 560 | Glu | Ser | Lys | Pro 565 | Ser | Glu | Leu | Leu Glu 570 |
| Gly | Gln | Pro | Val | Leu 575 | Leu | Ser | Cys | Gln 580 | Ala | Asp | Ser | Tyr Lys Tyr 585 |
| Glu | His | Leu | Arg | Trp 590 | Tyr | Arg | Leu | Asn 595 | Leu | Ser | Thr | Leu His Asp 600 |
| Ala | His | Gly | Asn | Pro 605 | Leu | Leu | Leu | Asp 610 | Cys | Lys | Asn | Val His Leu 615 |
| Phe | Ala | Thr | Pro | Leu 620 | Ala | Ala | Ser | Leu 625 | Glu | Glu | Val | Ala Pro Gly 630 |
| Ala | Arg | His | Ala | Thr 635 | Leu | Ser | Leu | Ser 640 | Ile | Pro | Arg | Val Ala Pro 645 |
| Glu | His | Glu | Gly | His 650 | Tyr | Val | Cys | Glu 655 | Val | Gln | Asp | Arg Arg Ser 660 |
| His | Asp | Lys | His | Cys 665 | His | Lys | Lys | Tyr 670 | Leu | Ser | Val | Gln Ala Leu 675 |
| Glu | Ala | Pro | Arg | Leu 680 | Thr | Gln | Asn | Leu 685 | Thr | Asp | Leu | Leu Val Asn 690 |
| Val | Ser | Asp | Ser | Leu 695 | Glu | Met | Gln | Cys 700 | Leu | Val | Ala | Gly Ala His 705 |
| Ala | Pro | Ser | Ile | Val 710 | Trp | Tyr | Lys | Asp 715 | Glu | Arg | Leu | Leu Glu Glu 720 |
| Lys | Ser | Gly | Val | Asp 725 | Leu | Ala | Asp | Ser 730 | Asn | Gln | Lys | Leu Ser Ile 735 |
| Gln | Arg | Val | Arg | Glu 740 | Glu | Asp | Ala | Gly 745 | Arg | Tyr | Leu | Cys Ser Val 750 |
| Cys | Asn | Ala | Lys | Gly 755 | Cys | Val | Asn | Ser 760 | Ser | Ala | Ser | Val Ala Val 765 |
| Glu | Gly | Ser | Glu | Asp 770 | Lys | Gly | Ser | Met 775 | Glu | Ile | Val | Ile Leu Val 780 |
| Gly | Thr | Gly | Val | Ile 785 | Ala | Val | Phe | Phe 790 | Trp | Val | Leu | Leu Leu Leu 795 |
| Ile | Phe | Cys | Asn | Met 800 | Arg | Arg | Pro | Ala 805 | His | Ala | Asp | Ile Lys Thr 810 |
| Gly | Tyr | Leu | Ser | Ile 815 | Ile | Met | Asp | Pro 820 | Gly | Glu | Val | Pro Leu Glu 825 |
| Glu | Gln | Cys | Glu | Tyr 830 | Leu | Ser | Tyr | Asp 835 | Ala | Ser | Gln | Trp Glu Phe 840 |
| Pro | Arg | Glu | Arg | Leu 845 | His | Leu | Gly | Arg 850 | Val | Leu | Gly | Tyr Gly Ala 855 |
| Phe | Gly | Lys | Val | Val 860 | Glu | Ala | Ser | Ala 865 | Phe | Gly | Ile | His Lys Gly 870 |
| Ser | Ser | Cys | Asp | Thr 875 | Val | Ala | Val | Lys 880 | Met | Leu | Lys | Glu Gly Ala 885 |
| Thr | Ala | Ser | Glu | His 890 | Arg | Ala | Leu | Met 895 | Ser | Glu | Leu | Lys Ile Leu 900 |
| Ile | His | Ile | Gly | Asn 905 | His | Leu | Asn | Val 910 | Val | Asn | Leu | Leu Gly Ala 915 |
| Cys | Thr | Lys | Pro | Gln | Gly | Pro | Leu | Met | Val | Ile | Val | Glu Phe Cys |

|     |     |     |     |     | 920 |     |     |     |     | 925 |     |     |     |     | 930 |
| --- | --- | --- | --- | --- | --- | --- | --- | --- | --- | --- | --- | --- | --- | --- | --- |
| Lys | Tyr | Gly | Asn | Leu | Ser | Asn | Phe | Leu | Arg | Ala | Lys | Arg | Asp | Ala |
|     |     |     |     |     | 935 |     |     |     |     | 940 |     |     |     |     | 945 |
| Phe | Ser | Pro | Cys | Ala | Glu | Lys | Ser | Pro | Glu | Gln | Arg | Gly | Arg | Phe |
|     |     |     |     |     | 950 |     |     |     |     | 955 |     |     |     |     | 960 |
| Arg | Ala | Met | Val | Glu | Leu | Ala | Arg | Leu | Asp | Arg | Arg | Arg | Pro | Gly |
|     |     |     |     |     | 965 |     |     |     |     | 970 |     |     |     |     | 975 |
| Ser | Ser | Asp | Arg | Val | Leu | Phe | Ala | Arg | Phe | Ser | Lys | Thr | Glu | Gly |
|     |     |     |     |     | 980 |     |     |     |     | 985 |     |     |     |     | 990 |
| Gly | Ala | Arg | Arg | Ala | Ser | Pro | Asp | Gln | Glu | Ala | Glu | Asp | Leu | Trp |
|     |     |     |     |     | 995 |     |     |     |     | 1000 |     |     |     |     | 1005 |
| Leu | Ser | Pro | Leu | Thr | Met | Glu | Asp | Leu | Val | Cys | Tyr | Ser | Phe | Gln |
|     |     |     |     |     | 1010 |     |     |     |     | 1015 |     |     |     |     | 1020 |
| Val | Ala | Arg | Gly | Met | Glu | Phe | Leu | Ala | Ser | Arg | Lys | Cys | Ile | His |
|     |     |     |     |     | 1025 |     |     |     |     | 1030 |     |     |     |     | 1035 |
| Arg | Asp | Leu | Ala | Ala | Arg | Asn | Ile | Leu | Leu | Ser | Glu | Ser | Asp | Val |
|     |     |     |     |     | 1040 |     |     |     |     | 1045 |     |     |     |     | 1050 |
| Val | Lys | Ile | Cys | Asp | Phe | Gly | Leu | Ala | Arg | Asp | Ile | Tyr | Lys | Asp |
|     |     |     |     |     | 1055 |     |     |     |     | 1060 |     |     |     |     | 1065 |
| Pro | Asp | Tyr | Val | Arg | Lys | Gly | Ser | Ala | Arg | Leu | Pro | Leu | Lys | Trp |
|     |     |     |     |     | 1070 |     |     |     |     | 1075 |     |     |     |     | 1080 |
| Met | Ala | Pro | Glu | Ser | Ile | Phe | Asp | Lys | Val | Tyr | Thr | Thr | Gln | Ser |
|     |     |     |     |     | 1085 |     |     |     |     | 1090 |     |     |     |     | 1095 |
| Asp | Val | Trp | Ser | Phe | Gly | Val | Leu | Leu | Trp | Glu | Ile | Phe | Ser | Leu |
|     |     |     |     |     | 1100 |     |     |     |     | 1105 |     |     |     |     | 1110 |
| Gly | Ala | Ser | Pro | Tyr | Pro | Gly | Val | Gln | Ile | Asn | Glu | Glu | Phe | Cys |
|     |     |     |     |     | 1115 |     |     |     |     | 1120 |     |     |     |     | 1125 |
| Gln | Arg | Leu | Arg | Asp | Gly | Thr | Arg | Met | Arg | Ala | Pro | Glu | Leu | Ala |
|     |     |     |     |     | 1130 |     |     |     |     | 1135 |     |     |     |     | 1140 |
| Thr | Pro | Ala | Ile | Arg | Arg | Ile | Met | Leu | Asn | Cys | Trp | Ser | Gly | Asp |
|     |     |     |     |     | 1145 |     |     |     |     | 1150 |     |     |     |     | 1155 |
| Pro | Lys | Ala | Arg | Pro | Ala | Phe | Ser | Glu | Leu | Val | Glu | Ile | Leu | Gly |
|     |     |     |     |     | 1160 |     |     |     |     | 1165 |     |     |     |     | 1170 |
| Asp | Leu | Leu | Gln | Gly | Arg | Gly | Leu | Gln | Glu | Glu | Glu | Glu | Val | Cys |
|     |     |     |     |     | 1175 |     |     |     |     | 1180 |     |     |     |     | 1185 |
| Met | Ala | Pro | Arg | Ser | Ser | Gln | Ser | Ser | Glu | Glu | Gly | Ser | Phe | Ser |
|     |     |     |     |     | 1190 |     |     |     |     | 1195 |     |     |     |     | 1200 |
| Gln | Val | Ser | Thr | Met | Ala | Leu | His | Ile | Ala | Gln | Ala | Asp | Ala | Glu |
|     |     |     |     |     | 1205 |     |     |     |     | 1210 |     |     |     |     | 1215 |
| Asp | Ser | Pro | Pro | Ser | Leu | Gln | Arg | His | Ser | Leu | Ala | Ala | Arg | Tyr |
|     |     |     |     |     | 1220 |     |     |     |     | 1225 |     |     |     |     | 1230 |
| Tyr | Asn | Trp | Val | Ser | Phe | Pro | Gly | Cys | Leu | Ala | Arg | Gly | Ala | Glu |
|     |     |     |     |     | 1235 |     |     |     |     | 1240 |     |     |     |     | 1245 |
| Thr | Arg | Gly | Ser | Ser | Arg | Met | Lys | Thr | Phe | Glu | Glu | Phe | Pro | Met |
|     |     |     |     |     | 1250 |     |     |     |     | 1255 |     |     |     |     | 1260 |
| Thr | Pro | Thr | Thr | Tyr | Lys | Gly | Ser | Val | Asp | Asn | Gln | Thr | Asp | Ser |
|     |     |     |     |     | 1265 |     |     |     |     | 1270 |     |     |     |     | 1275 |
| Gly | Met | Val | Leu | Ala | Ser | Glu | Glu | Phe | Glu | Gln | Ile | Glu | Ser | Arg |
|     |     |     |     |     | 1280 |     |     |     |     | 1285 |     |     |     |     | 1290 |
| His | Arg | Gln | Glu | Ser | Gly | Phe | Arg |
|     |     |     |     |     | 1295 |     | 1298 |

( 2 ) INFORMATION FOR SEQ ID NO:34:

( i ) SEQUENCE CHARACTERISTICS:
    ( A ) LENGTH: 3348 bases
    ( B ) TYPE: nucleic acid
    ( C ) STRANDEDNESS: single
    ( D ) TOPOLOGY: linear ( x i ) SEQUENCE DESCRIPTION: SEQ ID NO:34:

```
ATGGCTGGGA TTTTCTATTT CGCCCTATTT TCGTGTCTCT TCGGGATTTG   50
CGACGCTGTC ACAGGTTCCA GGGTATACCC CGCGAATGAA GTTACCTTAT  100
TGGATTCCAG ATCTGTTCAG GGAGAACTTG GGTGGATAGC AAGCCCTCTG  150
GAAGGAGGGT GGGAGGAAGT GAGTATCATG GATGAAAAAA ATACACCAAT  200
CCGAACCTAC CAAGTGTGCA ATGTGATGGA ACCCAGCCAG AATAACTGGC  250
TACGAACTGA TTGGATCACC CGAGAAGGGG CTCAGAGGGT GTATATTGAG  300
ATTAAATTCA CCTTGAGGGA CTGCAATAGT CTTCCGGGCG TCATGGGGAC  350
TTGCAAGGAG ACGTTTAACC TGTACTACTA TGAATCAGAC AACGACAAAG  400
AGCGTTTCAT CAGAGAGAAC CAGTTTGTCA AAATTGACAC CATTGCTGCT  450
GATGAGAGCT TCACCCAAGT GGACATTGGT GACAGAATCA TGAAGCTGAA  500
CACCGAGATC CGGGATGTAG GGCCATTAAG CAAAAGGGG TTTTACCTGG  550
CTTTTCAGGA TGTGGGGGCC TGCATCGCCC TGGTATCAGT CCGTGTGTTC  600
TATAAAAAGT GTCCACTCAC AGTCCGCAAT CTGGCCCAGT TTCCTGACAC  650
CATCACAGGG GCTGATACGT CTTCCCTGGT GGAAGTTCGA GGCTCCTGTG  700
TCAACAACTC AGAAGAGAAA GATGTGCCAA AAATGTACTG TGGGGCAGAT  750
GGTGAATGGC TGGTACCCAT TGGCAACTGC CTATGCAACG CTGGGCATGA  800
GGAGCGGAGC GGAGAATGCC AAGCTTGCAA AATTGGATAT TACAAGGCTC  850
TCTCCACGGA TGCCACCTGT GCCAAGTGCC CACCCCACAG CTACTCTGTC  900
TGGGAAGGAG CCACCTCGTG CACCTGTGAC CGAGGCTTTT TCAGAGCTGA  950
CAACGATGCT GCCTCTATGC CCTGCACCCG TCCACCATCT GCTCCCCTGA 1000
ACTTGATTTC AAATGTCAAC GAGACATCTG TGAACTTGGA ATGGAGTAGC 1050
CCTCAGAATA CAGGTGGCCG CCAGGACATT TCCTATAATG TGGTATGCAA 1100
GAAATGTGGA GCTGGTGACC CCAGCAAGTG CCGACCCTGT GGAAGTGGGG 1150
TCCACTACAC CCCACAGCAG AATGGCTTGA AGACCACCAA AGGCTCCATC 1200
ACTGACCTCC TAGCTCATAC CAATTACACC TTTGAAATCT GGGCTGTGAA 1250
TGGAGTGTCC AAATATAACC CTAACCCAGA CCAATCAGTT TCTGTCACTG 1300
TGACCACCAA CCAAGCAGCA CCATCATCCA TTGCTTTGGT CCAGGCTAAA 1350
GAAGTCACAA GATACAGTGT GGCACTGGCT TGGCTGGAAC CAGATCGGCC 1400
CAATGGGGTA ATCCTGGAAT ATGAAGTCAA GTATTATGAG AAGGATCAGA 1450
ATGAGCGAAG CTATCGTATA GTTCGGACAG CTGCCAGGAA CACAGATATC 1500
AAAGGCCTGA ACCCTCTCAC TTCCTATGTT TTCCACGTGC GAGCCAGGAC 1550
AGCAGCTGGC TATGGAGACT TCAGTGAGCC CTTGGAGGTT ACAACCAACA 1600
CAGTGCCTTC CCGGATCATT GGAGATGGGG CTAACTCCAC AGTCCTTCTG 1650
GTCTCTGTCT CGGGCAGTGT GGTGCTGGTG GTAATTCTCA TTGCAGCTTT 1700
TGTCATCAGC CGGAGACGGA GTAAATACAG TAAAGCCAAA CAAGAAGCGG 1750
ATGAAGAGAA ACATTTGAAT CAAGGTGTAA GAACATATGT GGACCCCTTT 1800
```

```
ACGTACGAAG ATCCCAACCA AGCAGTGCGA GAGTTTGCCA AAGAAATTGA  1850
CGCATCCTGC ATTAAGATTG AAAAAGTTAT AGGAGTTGGT GAATTTGGTG  1900
AGGTATGCAG TGGGCGTCTC AAAGTGCCTG GCAAGAGAGA GATCTGTGTG  1950
GCTATCAAGA CTCTGAAAGC TGGTTATACA GACAAACAGA GGAGAGACTT  2000
CCTGAGTGAG GCCAGCATCA TGGGACAGTT TGACCATCCG AACATCATTC  2050
ACTTGGAAGG CGTGGTCACT AAATGTAAAC CAGTAATGAT CATAACAGAG  2100
TACATGGAGA ATGGCTCCTT GGATGCATTC CTCAGGAAAA ATGATGGCAG  2150
ATTTACAGTC ATTCAGCTGG TGGGCATGCT TCGTGGCATT GGGTCTGGGA  2200
TGAAGTATTT ATCTGATATG AGCTATGTGC ATCGTGATCT GGCCGCACGG  2250
AACATCCTGG TGAACAGCAA CTTGGTCTGC AAAGTGTCTG ATTTTGGCAT  2300
GTCCCGAGTG CTTGAGGATG ATCCGGAAGC AGCTTACACC ACCAGGGGTG  2350
GCAAGATTCC TATCCGGTGG ACTGCGCCAG AAGCAATTGC CTATCGTAAA  2400
TTCACATCAG CAAGTGATGT ATGGAGCTAT GGAATCGTTA TGTGGGAAGT  2450
GATGTCGTAC GGGGAGAGGC CCTATTGGGA TATGTCCAAT CAAGATGTGA  2500
TTAAAGCCAT TGAGGAAGGC TATCGGTTAC CCCCTCCAAT GGACTGCCCC  2550
ATTGCGCTCC ACCAGCTGAT GCTAGACTGC TGGCAGAAGG AGAGGAGCGA  2600
CAGGCCTAAA TTTGGGCAGA TTGTCAACAT GTTGGACAAA CTCATCCGCA  2650
ACCCCAACAG CTTGAAGAGG ACAGGGACGG AGAGCTCCAG ACCTAACACT  2700
GCCTTGTTGG ATCCAAGCTC CCCTGAATTC TCTGCTGTGG TATCAGTGGG  2750
CGATTGGCTC CAGGCCATTA AAATGGACCG GTATAAGGAT AACTTCACAG  2800
CTGCTGGTTA TACCACACTA GAGGCTGTGG TGCACGTGAA CCAGGAGGAC  2850
CTGGCAAGAA TTGGTATCAC AGCCATCACA CACCAGAATA AGATTTTGAG  2900
CAGTGTCCAG GCAATGCGAA CCCAAATGCA GCAGATGCAC GGCAGAATGG  2950
TTCCCGTCTG AGCCAGTACT GAATAAACTC AAAACTCTTG AAATTAGTTT  3000
ACCTCATCCA TGCACTTTAA TTGAAGAACT GCACTTTTTT TACTTCGTCT  3050
TCGCCCTCTG AAATTAAAGA AATGAAAAAA AAAAACAAT ATCTGCAGCG   3100
TTGCTTGGTG CACAGATTGC TGAAACTGTG GGGCTTACAG AAATGACTGC  3150
CGGTCATTTG AATGAGACCT GGAACAAATC GTTTCTCAGA AGTACTTTTC  3200
TGTTCATCAC CAGTCTGTAA AATACATGTA CCTATAGAAA TAGAACACTG  3250
CCTCTGAGTT TTGATGCTGT ATTTGCTGCC AGACACTGAG CTTCTGAGAC  3300
ATCCCTGATT CTCTCTCCAT TTGGAATTAC AACGGTCGAC GAGCTCGA    3348
```

(2) INFORMATION FOR SEQ ID NO:35:

(i) SEQUENCE CHARACTERISTICS:
        (A) LENGTH: 3348 bases
        (B) TYPE: nucleic acid
        (C) STRANDEDNESS: single
        (D) TOPOLOGY: linear (xi) SEQUENCE DESCRIPTION: SEQ ID NO:35:

```
TACCGACCCT AAAAGATAAA GCGGGATAAA AGCACAGAGA AGCCCTAAAC   50
GCTGCGACAG TGTCCAAGGT CCCATATGGG GCGCTTACTT CAATGGAATA  100
ACCTAAGGTC TAGACAAGTC CCTCTTGAAC CCACCTATCG TTCGGGAGAC  150
CTTCCTCCCA CCCTCCTTCA CTCATAGTAC CTACTTTTTT TATGTGGTTA  200
```

```
GGCTTGGATG GTTCACACGT TACACTACCT TGGGTCGGTC TTATTGACCG    250
ATGCTTGACT AACCTAGTGG GCTCTTCCCC GAGTCTCCCA CATATAACTC    300
TAATTTAAGT GGAACTCCCT GACGTTATCA GAAGGCCCGC AGTACCCCTG    350
AACGTTCCTC TGCAAATTGG ACATGATGAT ACTTAGTCTG TTGCTGTTTC    400
TCGCAAAGTA GTCTCTCTTG GTCAAACAGT TTTAACTGTG GTAACGACGA    450
CTACTCTCGA AGTGGGTTCA CCTGTAACCA CTGTCTTAGT ACTTCGACTT    500
GTGGCTCTAG GCCCTACATC CCGGTAATTC GTTTTCCCC  AAAATGGACC    550
GAAAAGTCCT ACACCCCGG  ACGTAGCGGG ACCATAGTCA GGCACACAAG    600
ATATTTTTCA CAGGTGAGTG TCAGGCGTTA GACCGGGTCA AAGGACTGTG    650
GTAGTGTCCC CGACTATGCA GAAGGGACCA CCTTCAAGCT CCGAGGACAC    700
AGTTGTTGAG TCTTCTCTTT CTACACGGTT TTACATGAC  ACCCCGTCTA    750
CCACTTACCG ACCATGGGTA ACCGTTGACG GATACGTTGC GACCCGTACT    800
CCTCGCCTCG CCTCTTACGG TTCGAACGTT TTAACCTATA ATGTTCCGAG    850
AGAGGTGCCT ACGGTGGACA CGGTTCACGG GTGGGGTGTC GATGAGACAG    900
ACCCTTCCTC GGTGGAGCAC GTGGACACTG GCTCCGAAAA AGTCTCGACT    950
GTTGCTACGA CGGAGATACG GGACGTGGGC AGGTGGTAGA CGAGGGGACT   1000
TGAACTAAAG TTTACAGTTG CTCTGTAGAC ACTTGAACCT TACCTCATCG   1050
GGAGTCTTAT GTCCACCGGC GGTCCTGTAA AGGATATTAC ACCATACGTT   1100
CTTTACACCT CGACCACTGG GGTCGTTCAC GGCTGGGACA CCTTCACCCC   1150
AGGTGATGTG GGGTGTCGTC TTACCGAACT TCTGGTGGTT TCCGAGGTAG   1200
TGACTGGAGG ATCGAGTATG GTTAATGTGG AAACTTAGA  CCCGACACTT   1250
ACCTCACAGG TTTATATTGG GATTGGGTCT GGTTAGTCAA AGACAGTGAC   1300
ACTGGTGGTT GGTTCGTCGT GGTAGTAGGT AACGAAACCA GGTCCGATTT   1350
CTTCAGTGTT CTATGTCACA CCGTGACCGA ACCGACCTTG GTCTAGCCGG   1400
GTTACCCCAT TAGGACCTTA TACTTCAGTT CATAATACTC TTCCTAGTCT   1450
TACTCGCTTC GATAGCATAT CAAGCCTGTC GACGGTCCTT GTGTCTATAG   1500
TTTCCGGACT TGGGAGAGTG AAGGATACAA AAGGTGCACG CTCGGTCCTG   1550
TCGTCGACCG ATACCTCTGA AGTCACTCGG GAACCTCCAA TGTTGGTTGT   1600
GTCACGGAAG GGCCTAGTAA CCTCTACCCC GATTGAGGTG TCAGGAAGAC   1650
CAGAGACAGA GCCCGTCACA CCACGACCAC CATTAAGAGT AACGTCGAAA   1700
ACAGTAGTCG GCCTCTGCCT CATTTATGTC ATTTCGGTTT GTTCTTCGCC   1750
TACTTCTCTT TGTAAACTTA GTTCCACATT CTTGTATACA CCTGGGGAAA   1800
TGCATGCTTC TAGGGTTGGT TCGTCACGCT CTCAAACGGT TTCTTTAACT   1850
GCGTAGGACG TAATTCTAAC TTTTTCAATA TCCTCAACCA CTTAAACCAC   1900
TCCATACGTC ACCCGCAGAG TTTCACGGAC CGTTCTCTCT CTAGACACAC   1950
CGATAGTTCT GAGACTTTCG ACCAATATGT CTGTTTGTCT CCTCTCTGAA   2000
GGACTCACTC CGGTCGTAGT ACCCTGTCAA ACTGGTAGGC TTGTAGTAAG   2050
TGAACCTTCC GCACCAGTGA TTTACATTTG GTCATTACTA GTATTGTCTC   2100
ATGTACCTCT TACCGAGGAA CCTACGTAAG GAGTCCTTTT TACTACCGTC   2150
TAAATGTCAG TAAGTCGACC ACCCGTACGA AGCACCGTAA CCCAGACCCT   2200
```

```
ACTTCATAAA    TAGACTATAC    TCGATACACG    TAGCACTAGA    CCGGCGTGCC    2250
TTGTAGGACC    ACTTGTCGTT    GAACCAGACG    TTTCACAGAC    TAAAACCGTA    2300
CAGGGCTCAC    GAACTCCTAC    TAGGCCTTCG    TCGAATGTGG    TGGTCCCCAC    2350
CGTTCTAAGG    ATAGGCCACC    TGACGCGGTC    TTCGTTAACG    GATAGCATTT    2400
AAGTGTAGTC    GTTCACTACA    TACCTCGATA    CCTTAGCAAT    ACACCCTTCA    2450
CTACAGCATG    CCCCTCTCCG    GGATAACCCT    ATACAGGTTA    GTTCTACACT    2500
AATTTCGGTA    ACTCCTTCCG    ATAGCCAATG    GGGGAGGTTA    CCTGACGGGG    2550
TAACGCGAGG    TGGTCGACTA    CGATCTGACG    ACCGTCTTCC    TCTCCTCGCT    2600
GTCCGGATTT    AAACCCGTCT    AACAGTTGTA    CAACCTGTTT    GAGTAGGCGT    2650
TGGGGTTGTC    GAACTTCTCC    TGTCCCTGCC    TCTCGAGGTC    TGGATTGTGA    2700
CGGAACAACC    TAGGTTCGAG    GGGACTTAAG    AGACGACACC    ATAGTCACCC    2750
GCTAACCGAG    GTCCGGTAAT    TTTACCTGGC    CATATTCCTA    TTGAAGTGTC    2800
GACGACCAAT    ATGGTGTGAT    CTCCGACACC    ACGTGCACTT    GGTCCTCCTG    2850
GACCGTTCTT    AACCATAGTG    TCGGTAGTGT    GTGGTCTTAT    TCTAAAACTC    2900
GTCACAGGTC    CGTTACGCTT    GGGTTTACGT    CGTCTACGTG    CCGTCTTACC    2950
AAGGGCAGAC    TCGGTCATGA    CTTATTTGAG    TTTTGAGAAC    TTTAATCAAA    3000
TGGAGTAGGT    ACGTGAAATT    AACTTCTTGA    CGTGAAAAAA    ATGAAGCAGA    3050
AGCGGGAGAC    TTTAATTTCT    TTACTTTTTT    TTTTTGTTA     TAGACGTCGC    3100
AACGAACCAC    GTGTCTAACG    ACTTTGACAC    CCCGAATGTC    TTTACTGACG    3150
GCCAGTAAAC    TTACTCTGGA    CCTTGTTTAG    CAAAGAGTCT    TCATGAAAAG    3200
ACAAGTAGTG    GTCAGACATT    TTATGTACAT    GGATATCTTT    ATCTTGTGAC    3250
GGAGACTCAA    AACTACGACA    TAAACGACGG    TCTGTGACTC    GAAGACTCTG    3300
TAGGGACTAA    GAGAGAGGTA    AACCTTAATG    TTGCCAGCTG    CTCGAGCT      3348
```

( 2 ) INFORMATION FOR SEQ ID NO:36:

( i ) SEQUENCE CHARACTERISTICS:
        ( A ) LENGTH: 1104 amino acids
        ( B ) TYPE: amino acid
        ( D ) TOPOLOGY: linear ( x i ) SEQUENCE DESCRIPTION: SEQ ID NO:36:

```
Met  Ala  Gly  Ile  Phe  Tyr  Phe  Ala  Leu  Phe  Ser  Cys  Leu  Phe  Gly
 1              5                        10                       15

Ile  Cys  Asp  Ala  Val  Thr  Gly  Ser  Arg  Val  Tyr  Pro  Ala  Asn  Glu
                20                       25                       30

Val  Thr  Leu  Leu  Asp  Ser  Arg  Ser  Val  Gln  Gly  Glu  Leu  Gly  Trp
                35                       40                       45

Ile  Ala  Ser  Pro  Leu  Glu  Gly  Gly  Trp  Glu  Glu  Val  Ser  Ile  Met
                50                       55                       60

Asp  Glu  Lys  Asn  Thr  Pro  Ile  Arg  Thr  Tyr  Gln  Val  Cys  Asn  Val
                65                       70                       75

Met  Glu  Pro  Ser  Gln  Asn  Asn  Trp  Leu  Arg  Thr  Asp  Trp  Ile  Thr
                80                       85                       90

Arg  Glu  Gly  Ala  Gln  Arg  Val  Tyr  Ile  Glu  Ile  Lys  Phe  Thr  Leu
                95                      100                      105

Arg  Asp  Cys  Asn  Ser  Leu  Pro  Gly  Val  Met  Gly  Thr  Cys  Lys  Glu
                110                     115                      120
```

| | | | | | | | | | | | | |
|---|---|---|---|---|---|---|---|---|---|---|---|---|
| Thr | Phe | Asn | Leu | Tyr 125 | Tyr | Tyr | Glu | Ser | Asp 130 | Asn | Asp | Lys | Glu | Arg 135 |
| Phe | Ile | Arg | Glu | Asn 140 | Gln | Phe | Val | Lys | Ile 145 | Asp | Thr | Ile | Ala | Ala 150 |
| Asp | Glu | Ser | Phe | Thr 155 | Gln | Val | Asp | Ile | Gly 160 | Asp | Arg | Ile | Met | Lys 165 |
| Leu | Asn | Thr | Glu | Ile 170 | Arg | Asp | Val | Gly | Pro 175 | Leu | Ser | Lys | Lys | Gly 180 |
| Phe | Tyr | Leu | Ala | Phe 185 | Gln | Asp | Val | Gly | Ala 190 | Cys | Ile | Ala | Leu | Val 195 |
| Ser | Val | Arg | Val | Phe 200 | Tyr | Lys | Lys | Cys | Pro 205 | Leu | Thr | Val | Arg | Asn 210 |
| Leu | Ala | Gln | Phe | Pro 215 | Asp | Thr | Ile | Thr | Gly 220 | Ala | Asp | Thr | Ser | Ser 225 |
| Leu | Val | Glu | Val | Arg 230 | Gly | Ser | Cys | Val | Asn 235 | Asn | Ser | Glu | Glu | Lys 240 |
| Asp | Val | Pro | Lys | Met 245 | Tyr | Cys | Gly | Ala | Asp 250 | Gly | Glu | Trp | Leu | Val 255 |
| Pro | Ile | Gly | Asn | Cys 260 | Leu | Cys | Asn | Ala | Gly 265 | His | Glu | Glu | Arg | Ser 270 |
| Gly | Glu | Cys | Gln | Ala 275 | Cys | Lys | Ile | Gly | Tyr 280 | Tyr | Lys | Ala | Leu | Ser 285 |
| Thr | Asp | Ala | Thr | Cys 290 | Ala | Lys | Cys | Pro | Pro 295 | His | Ser | Tyr | Ser | Val 300 |
| Trp | Glu | Gly | Ala | Thr 305 | Ser | Cys | Thr | Cys | Asp 310 | Arg | Gly | Phe | Phe | Arg 315 |
| Ala | Asp | Asn | Asp | Ala 320 | Ala | Ser | Met | Pro | Cys 325 | Thr | Arg | Pro | Pro | Ser 330 |
| Ala | Pro | Leu | Asn | Leu 335 | Ile | Ser | Asn | Val | Asn 340 | Glu | Thr | Ser | Val | Asn 345 |
| Leu | Glu | Trp | Ser | Ser 350 | Pro | Gln | Asn | Thr | Gly 355 | Gly | Arg | Gln | Asp | Ile 360 |
| Ser | Tyr | Asn | Val | Val 365 | Cys | Lys | Lys | Cys | Gly 370 | Ala | Gly | Asp | Pro | Ser 375 |
| Lys | Cys | Arg | Pro | Cys 380 | Gly | Ser | Gly | Val | His 385 | Tyr | Thr | Pro | Gln | Gln 390 |
| Asn | Gly | Leu | Lys | Thr 395 | Thr | Lys | Gly | Ser | Ile 400 | Thr | Asp | Leu | Leu | Ala 405 |
| His | Thr | Asn | Tyr | Thr 410 | Phe | Glu | Ile | Trp | Ala 415 | Val | Asn | Gly | Val | Ser 420 |
| Lys | Tyr | Asn | Pro | Asn 425 | Pro | Asp | Gln | Ser | Val 430 | Ser | Val | Thr | Val | Thr 435 |
| Thr | Asn | Gln | Ala | Ala 440 | Pro | Ser | Ser | Ile | Ala 445 | Leu | Val | Gln | Ala | Lys 450 |
| Glu | Val | Thr | Arg | Tyr 455 | Ser | Val | Ala | Leu | Ala 460 | Trp | Leu | Glu | Pro | Asp 465 |
| Arg | Pro | Asn | Gly | Val 470 | Ile | Leu | Glu | Tyr | Glu 475 | Val | Lys | Tyr | Tyr | Glu 480 |
| Lys | Asp | Gln | Asn | Glu 485 | Arg | Ser | Tyr | Arg | Ile 490 | Val | Arg | Thr | Ala | Ala 495 |
| Arg | Asn | Thr | Asp | Ile 500 | Lys | Gly | Leu | Asn | Pro 505 | Leu | Thr | Ser | Tyr | Val 510 |
| Phe | His | Val | Arg | Ala | Arg | Thr | Ala | Ala | Gly | Tyr | Gly | Asp | Phe | Ser |

```
                          515                    520                        525
Glu  Pro  Leu  Glu  Val  Thr  Thr  Asn  Thr  Val  Pro  Ser  Arg  Ile  Ile
                    530                      535                         540
Gly  Asp  Gly  Ala  Asn  Ser  Thr  Val  Leu  Leu  Val  Ser  Val  Ser  Gly
                    545                      550                         555
Ser  Val  Val  Leu  Val  Val  Ile  Leu  Ile  Ala  Ala  Phe  Val  Ile  Ser
                    560                      565                         570
Arg  Arg  Arg  Ser  Lys  Tyr  Ser  Lys  Ala  Lys  Gln  Glu  Ala  Asp  Glu
                    575                      580                         585
Glu  Lys  His  Leu  Asn  Gln  Gly  Val  Arg  Thr  Tyr  Val  Asp  Pro  Phe
                    590                      595                         600
Thr  Tyr  Glu  Asp  Pro  Asn  Gln  Ala  Val  Arg  Glu  Phe  Ala  Lys  Glu
                    605                      610                         615
Ile  Asp  Ala  Ser  Cys  Ile  Lys  Ile  Glu  Lys  Val  Ile  Gly  Val  Gly
                    620                      625                         630
Glu  Phe  Gly  Glu  Val  Cys  Ser  Gly  Arg  Leu  Lys  Val  Pro  Gly  Lys
                    635                      640                         645
Arg  Glu  Ile  Cys  Val  Ala  Ile  Lys  Thr  Leu  Lys  Ala  Gly  Tyr  Thr
                    650                      655                         660
Asp  Lys  Gln  Arg  Arg  Asp  Phe  Leu  Ser  Glu  Ala  Ser  Ile  Met  Gly
                    665                      670                         675
Gln  Phe  Asp  His  Pro  Asn  Ile  Ile  His  Leu  Glu  Gly  Val  Val  Thr
                    680                      685                         690
Lys  Cys  Lys  Pro  Val  Met  Ile  Ile  Thr  Glu  Tyr  Met  Glu  Asn  Gly
                    695                      700                         705
Ser  Leu  Asp  Ala  Phe  Leu  Arg  Lys  Asn  Asp  Gly  Arg  Phe  Thr  Val
                    710                      715                         720
Ile  Gln  Leu  Val  Gly  Met  Leu  Arg  Gly  Ile  Gly  Ser  Gly  Met  Lys
                    725                      730                         735
Tyr  Leu  Ser  Asp  Met  Ser  Tyr  Val  His  Arg  Asp  Leu  Ala  Ala  Arg
                    740                      745                         750
Asn  Ile  Leu  Val  Asn  Ser  Asn  Leu  Val  Cys  Lys  Val  Ser  Asp  Phe
                    755                      760                         765
Gly  Met  Ser  Arg  Val  Leu  Glu  Asp  Asp  Pro  Glu  Ala  Ala  Tyr  Thr
                    770                      775                         780
Thr  Arg  Gly  Gly  Lys  Ile  Pro  Ile  Arg  Trp  Thr  Ala  Pro  Glu  Ala
                    785                      790                         795
Ile  Ala  Tyr  Arg  Lys  Phe  Thr  Ser  Ala  Ser  Asp  Val  Trp  Ser  Tyr
                    800                      805                         810
Gly  Ile  Val  Met  Trp  Glu  Val  Met  Ser  Tyr  Gly  Glu  Arg  Pro  Tyr
                    815                      820                         825
Trp  Asp  Met  Ser  Asn  Gln  Asp  Val  Ile  Lys  Ala  Ile  Glu  Glu  Gly
                    830                      835                         840
Tyr  Arg  Leu  Pro  Pro  Pro  Met  Asp  Cys  Pro  Ile  Ala  Leu  His  Gln
                    845                      850                         855
Leu  Met  Leu  Asp  Cys  Trp  Gln  Lys  Glu  Arg  Ser  Asp  Arg  Pro  Lys
                    860                      865                         870
Phe  Gly  Gln  Ile  Val  Asn  Met  Leu  Asp  Lys  Leu  Ile  Arg  Asn  Pro
                    875                      880                         885
Asn  Ser  Leu  Lys  Arg  Thr  Gly  Thr  Glu  Ser  Ser  Arg  Pro  Asn  Thr
                    890                      895                         900
Ala  Leu  Leu  Asp  Pro  Ser  Ser  Pro  Glu  Phe  Ser  Ala  Val  Val  Ser
                    905                      910                         915
```

| | | | | | | | | | | | | |
|---|---|---|---|---|---|---|---|---|---|---|---|---|
|Val|Gly|Asp|Trp|Leu|Gln|Ala|Ile|Lys|Met|Asp|Arg|Tyr|Lys|Asp|
| | | |920| | | |925| | | |930|
|Asn|Phe|Thr|Ala|Ala|Gly|Tyr|Thr|Thr|Leu|Glu|Ala|Val|Val|His|
| | | |935| | | |940| | | |945|
|Val|Asn|Gln|Glu|Asp|Leu|Ala|Arg|Ile|Gly|Ile|Thr|Ala|Ile|Thr|
| | | |950| | | |955| | | |960|
|His|Gln|Asn|Lys|Ile|Leu|Ser|Ser|Val|Gln|Ala|Met|Arg|Thr|Gln|
| | | |965| | | |970| | | |975|
|Met|Gln|Gln|Met|His|Gly|Arg|Met|Val|Pro|Val|Ala|Ser|Thr|Glu|
| | | |980| | | |985| | | |990|
|Thr|Gln|Asn|Ser|Asn|Phe|Thr|Ser|Ser|Met|His|Phe|Asn|Arg|Thr|
| | | |995| | | |1000| | | |1005|
|Ala|Leu|Phe|Leu|Leu|Arg|Leu|Arg|Pro|Leu|Lys|Leu|Lys|Lys|Lys|
| | | |1010| | | |1015| | | |1020|
|Lys|Lys|Asn|Asn|Ile|Cys|Ser|Val|Ala|Trp|Cys|Thr|Asp|Cys|Asn|
| | | |1025| | | |1030| | | |1035|
|Cys|Gly|Ala|Tyr|Arg|Asn|Asp|Cys|Arg|Ser|Phe|Glu|Asp|Leu|Glu|
| | | |1040| | | |1045| | | |1050|
|Gln|Ile|Val|Ser|Gln|Lys|Tyr|Phe|Ser|Val|His|His|Gln|Ser|Val|
| | | |1055| | | |1060| | | |1065|
|Lys|Tyr|Met|Tyr|Leu|Lys|Asn|Thr|Ala|Ser|Glu|Phe|Cys|Cys|Ile|
| | | |1070| | | |1075| | | |1080|
|Cys|Cys|Gln|Thr|Leu|Ser|Phe|Asp|Ile|Pro|Asp|Ser|Leu|Ser|Ile|
| | | |1085| | | |1090| | | |1095|
|Trp|Asn|Tyr|Asn|Gly|Arg|Arg|Ala|Arg|
| | | |1100| | | |1104|

( 2 ) INFORMATION FOR SEQ ID NO:37:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( x i ) SEQUENCE DESCRIPTION: SEQ ID NO:37:

TCGGATCCAC ACGNGACTCT TGGC   24

( 2 ) INFORMATION FOR SEQ ID NO:38:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( x i ) SEQUENCE DESCRIPTION: SEQ ID NO:38:

TCGGATCCAC TCAGNGACTC TTNGCNGC   28

( 2 ) INFORMATION FOR SEQ ID NO:39:

( i ) SEQUENCE CHARACTERISTICS:
        ( A ) LENGTH: 32 bases
        ( B ) TYPE: nucleic acid
        ( C ) STRANDEDNESS: single
        ( D ) TOPOLOGY: linear ( x i ) SEQUENCE DESCRIPTION: SEQ ID NO:39:

CTCGAATTCC AGATAAGCGT ACCAGCACAG TC   32

( 2 ) INFORMATION FOR SEQ ID NO:40:

( i ) SEQUENCE CHARACTERISTICS:
    ( A ) LENGTH: 32 bases
    ( B ) TYPE: nucleic acid
    ( C ) STRANDEDNESS: single
    ( D ) TOPOLOGY: linear ( x i ) SEQUENCE DESCRIPTION: SEQ ID NO:40:

CTCGAATTCC AGATATCCGT ACCATAACAG TC 32

( 2 ) INFORMATION FOR SEQ ID NO:41:

( i ) SEQUENCE CHARACTERISTICS:
        ( A ) LENGTH: 13 amino acids
        ( B ) TYPE: amino acid
        ( D ) TOPOLOGY: linear ( x i ) SEQUENCE DESCRIPTION: SEQ ID NO:41:

Met Asp Tyr Lys Asp Asp Asp Lys Lys Leu Ala Met
1           5                   10          13

( 2 ) INFORMATION FOR SEQ ID NO:42:

( i ) SEQUENCE CHARACTERISTICS:
        ( A ) LENGTH: 54 bases
        ( B ) TYPE: nucleic acid
        ( C ) STRANDEDNESS: single
        ( D ) TOPOLOGY: linear ( x i ) SEQUENCE DESCRIPTION: SEQ ID NO:42:

CCGGATATCA TGGACTACAA GGACGACGAT GACAAGAAGC TTGCCATGGA 50

GCTC 54